(12) United States Patent
Christ et al.

(10) Patent No.: US 7,939,661 B2
(45) Date of Patent: *May 10, 2011

(54) PYRIDINE, QUINOLINE AND PYRIMIDINE DERIVATIVES

(75) Inventors: Andreas D. Christ, Arlesheim (CH); Rainer E. Martin, Basel (CH); Peter Mohr, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 819 days.

This patent is subject to a terminal disclaimer.

(21) Appl. No.: 11/847,467

(22) Filed: Aug. 30, 2007

(65) Prior Publication Data

US 2008/0064697 A1    Mar. 13, 2008

(30) Foreign Application Priority Data

Sep. 11, 2006   (EP) ..................................... 06120457

(51) Int. Cl.
C07D 215/38   (2006.01)
A61K 31/04   (2006.01)

(52) U.S. Cl. ........ 544/322; 546/162; 546/193; 546/194; 514/256; 514/313; 514/318

(58) Field of Classification Search ................... 514/256, 514/313, 318; 544/322; 546/162, 193, 194
See application file for complete search history.

(56) References Cited

U.S. PATENT DOCUMENTS 7,674,804 B2 * 3/2010 Christ et al. .................. 514/326

2005/0222175 A1   10/2005 Dhanoa
2005/0222176 A1   10/2005 Dhanoa

FOREIGN PATENT DOCUMENTS

WO    WO 03/106452 A    12/2003
WO    WO 2006/063465 A   6/2006

* cited by examiner

Primary Examiner — D. Margaret Seaman
(74) Attorney, Agent, or Firm — George W. Johnston; Dennis P. Tramaloni; Samuel H. Megerditchian

(57) ABSTRACT

This invention is concerned with compounds of the formula

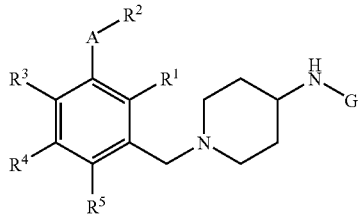

wherein A, $R^1$ to $R^5$ are as defined in the specification and G is a pyridine, quinoline or pyrimidine group as defined in the specification, and pharmaceutically acceptable salts thereof. The invention further relates to pharmaceutical compositions containing such compounds, to a process for their preparation and to their use for the treatment and/or prevention of diseases which are associated with the modulation of SST receptors subtype 5.

24 Claims, No Drawings

PYRIDINE, QUINOLINE AND PYRIMIDINE DERIVATIVES

PRIORITY TO RELATED APPLICATION(S)

This application claims the benefit of European Patent Application No. 06120457.4, filed Sep. 11, 2006, which is hereby incorporated by reference in its entirety.

FIELD OF THE INVENTION

The present invention is concerned with novel pyridine, quinoline and pyrimidine derivatives, their manufacture, pharmaceutical compositions containing them and their use as medicaments.

The active compounds of the present invention are useful in the prevention and/or treatment of diabetes mellitus and other disorders.

In particular, the present invention is concerned with compounds of the general formula I

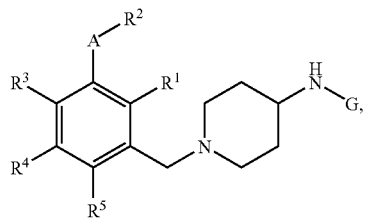

and pharmaceutically acceptable salts thereof.

All documents cited or relied upon below are expressly incorporated herein by reference.

BACKGROUND OF THE INVENTION

The compounds of formula I possess pharmaceutical activity, in particular they are modulators of somatostatin receptor activity. More particularly, the compounds are antagonists of the somatostatin receptor subtype 5 (SSTR5).

Diabetes mellitus is a systemic disease characterized by metabolic disorders involving insulin, carbohydrates, fats and proteins, and disorders in the structure and function of blood vessels. The primary symptom of acute diabetes is hyperglycemia, often accompanied by glucosuria, the presence in urine of large amounts of glucose, and polyuria, the excretion of large volumes of urine. Additional symptoms arise in chronic diabetes, including degeneration of the walls of blood vessels. Although many different human organs are affected by these vascular changes, the eyes and kidneys appear to be the most susceptible. As such, long-standing diabetes mellitus, even when treated with insulin, is a leading cause of blindness.

There are three recognized types of diabetes mellitus. Type I diabetes or insulin dependent diabetes mellitus (IDDM) is typically of juvenile onset; ketosis develops early in life with much more severe symptoms and has a near-certain prospect of later vascular involvement. Control of Type I diabetes is difficult and requires exogenous insulin administration. Type II diabetes or non-insulin dependent diabetes mellitus (NIDDM) is ketosis-resistant, generally develops later in life, is milder and has a more gradual onset. Gestational diabetes is related to type II diabetes and associated with an increased risk of later development of that disease. Type III diabetes is malnutrition-related diabetes.

NIDDM is a condition that poses a major threat to the health of the citizens of the western world. NIDDM accounts for over 85% of diabetes incidence worldwide and about 160 million people are suffering from NIDDM. The incidence is expected to increase considerably within the next decades, especially in developing countries. NIDDM is associated with morbidity and premature mortality resulting from serious complications, e.g., cardiovascular disease (G. C. Weir and J. L. Leahy, Pathogenesis of non-insulin dependent (Type II) diabetes mellitus, in *Joslin's Diabetes Mellitus* (Eds. C. R. Kahn and G. C. Weir), 13th Edition, 1994, Lea & Febiger, Malvern, Pa., pp. 240-264). NIDDM is characterized by both fasting and post-prandial hyperglycemia resulting from abnormalities in insulin secretion and insulin action (G. C. Weir et al., vide supra).

The hyperglycemia in patients suffering from NIDDM can usually be initially treated by dieting, but eventually most NIDDM patients have to take oral antidiabetic agents and/or insulin injections to normalize their blood glucose levels. The introduction of orally effective hypoglycemic agents was an important development in the treatment of hyperglycemia by lowering blood glucose levels. Currently, the most widely used oral antidiabetic agents are the sulfonylureas, which act by increasing the secretion of insulin from the pancreas (H. E. Lebovitz, Oral antidiabetic agents, in *Joslin's Diabetes Mellitus* (Eds. C. R. Kahn and G. C. Weir), 13th Edition, 1994, Lea & Febiger, Malvern, Pa., pp. 508-529), the biguanides (e.g., metformin) which act on the liver and periphery by unknown mechanisms (C. J. Bailey, M. R. C. Path and R. C. Turner *N. Engl. J. Med.* 1996, 334, 574-579) and the thiazolidinediones (e.g., rosiglitazone/Avandia®), which enhance the effects of insulin at peripheral target sites (G. L. Plosker and D. Faulds *Drugs* 1999, 57, 409-438). These existing therapies which comprise a wide variety of biguanide, sulfonylurea and thiazolidinedione derivatives have been used clinically as hypoglycemic agents. However, all three classes of compound have side effects. The biguanides, for example metformin, are unspecific and in certain cases have been associated with lactic acidosis, and need to be given over a longer period of time, i.e. they are not suitable for acute administration (C. J. Bailey et al., vide supra). The sulfonylureas, though having good hypoglycemic activity, require great care during use because they frequently cause serious hypoglycemia and are most effective over a period of circa ten years. The thiazolidinediones may cause weight gain following chronic administration (G. L. Plosker and D. Faulds, vide supra) and troglitazone has been associated with the occurrence of serious hepatic dysfunction.

Thus, there is a significant and rising need for antidiabetic drugs that have novel mechanisms of action, thereby avoiding side effects produced by known therapies. The hormone somatostatin (SST) is primarily produced in the intestinal tract and in the pancreas. In addition it acts as a neurotransmitter. The hormone is involved through its receptors in the regulation of several other hormones and in immunoregulation. In particular, SST suppresses the secretion of insulin by pancreatic β cells and the secretion of glucagon-like peptide 1 (GLP-1) by L cells. GLP-1 in turn is one of the most potent stimulators of insulin production and secretion and is a trophic factor for β cells. β and L cells express SST receptor subtype 5 (SSTR5) and agonizing this receptor suppresses insulin and GLP-1 secretion in humans and in animal models (e.g., Y. Zambre, Z. Ling, M.-C. Chen, X. Hou, C.-W. Woon, M. Culler, J. E. Taylor, D. H. Coy, C. van Schravendijk, F. Schuit, D. G. Pipeleers and D. L. Eizirik *Biochem. Pharmacol.* 1999, 57, 1159-1164; S. P. Fagan, A. Azizzadeh, S. Moldovan, M. K. Ray, T. E. Adrian, X. Ding, D. H. Coy and F. C. Brunicardi *Surgery* 1998, 124, 254-258; M. Norman, S. Moldovan, V. Seghers, X.-P. Wang, F. J. DeMayo and F. C. Brunicardi *Ann. Surg.* 2002, 235, 767-774; T. A. Tirone, M. A. Norman, S. Moldovan, F. J. DeMayo, X.-P. Wang and F. C. Brunicardi *Pancreas* 2003, 26, e67-73; M. Z. Strowski, M. Köhler, H. Y. Chen, M. E. Trumbauer, Z. Li, D. Szalkowski, S. Gopal-Truter, J. K. Fisher, J. M. Schaeffer, A. D. Blake, B. B. Zhang and H. A. Wilkinson *Mol. Endocrinol.* 2003, 17, 93-106).

Consequently, antagonizing the effect of SST would lead to higher plasma insulin concentrations. In patients suffering from impaired glucose tolerance and NIDDM, a higher plasma insulin concentration would moderate the dangerous hyperglycemia and accordingly reduce the risk of tissue damage. If such SSTR5 antagonists are sufficiently selective over the other four SST receptors, little influence is expected on secretion of other hormones. Particularly, selectivity over SST receptor subtype 2 avoids influences on glucagon secretion (K. Cejvan, D. H. Coy and S. Efendic *Diabetes* 2003, 52, 1176-1181; M. Z. Strowski, R. M. Parmar, A. D. Blake and J. M. Schaeffer *Endocrinology* 2000, 141, 111-117). Advantageous over established therapies is the dual mechanism of action to increase insulin secretion: directly on pancreatic β cells and indirectly through GLP-1 release from L cells. Additionally, SSTR5 knockout mice demonstrated higher insulin sensitivity than littermates (M. Z. Strowski, M. Köhler et al., vide supra). Therefore, SSTR5 antagonists could have the potential to beneficially influence insulin resistance in patients with NIDDM. In summary, SSTR5 antagonists are expected to beneficially influence NIDDM, the underlying impaired fasting glucose and impaired glucose tolerance, as well as complications of long-standing, insufficiently controlled diabetes mellitus.

GLP-1 is known as an endogenous regulator of gastrointestinal motility and of food intake reducing appetite as shown in laboratory animals, healthy volunteers and patients with NIDDM (E. Näslund, B. Barkeling, N. King, M. Gutniak, J. E. Blundell, J. J. Holst, S. Rössner and P. M. Hellström *Int. J. Obes.* 1999, 23, 304-311; J.-P. Gutzwiller, B. Göke, J. Drewe, P. Hildebrand, S. Ketterer, D. Handschin, R. Winterhalder, D. Conen and C. Beglinger *Gut* 1999, 44, 81-88; J.-P. Gutzwiller, J. Drewe, B. Göke, H. Schmidt, B. Rohrer, J. Lareida and C. Beglinger *Am. J. Physiol.* 1999, 276, R1541-1544; M. D. Turton, D. O'Shea, I. Gunn, S. A. Beak, C. M. Edwards, K. Meeran, S. J. Choi, G. M. Taylor, M. M. Heath, P. D. Lambert, J. P. Wilding, D. M. Smith, M. A. Ghatei, J. Herbert and S. R. Bloom *Nature* 1996, 379, 69-72; A. Flint, A. Raben, A. Astrup and J. J. Holst *J. Clin. Invest.* 1998, 101, 515-520; M. B. Toft-Nielsen, S. Madsbad and J. J. Holst *Diabetes Care* 1999, 22, 1137-1143; P. K. Cheikani, A. C. Haver and R. D. Reidelberger *Am. J. Physiol.* 2005, 288, R1695-R1706; T. Miki, K. Minami, H. Shinozaki, K. Matsumura, A. Saraya, H. Ikeda, Y. Yamada, J. J. Holst and S. Seino *Diabetes* 2005, 54, 1056-1063); thus, elevated GLP-1 will also counteract obesity, a typical condition associated with and leading to NIDDM.

GLP-1 is co-secreted with GLP-2 that is, consequently, also regulated by SST through SSTR5 (L. Hansen, B. Hartmann, T. Bisgaard, H. Mineo, P. N. Jørgensen and J. J. Holst *Am. J. Phys.* 2000, 278, E1010-1018). GLP-2 is enterotrophic and beneficial in patients with malabsorption of certain origins, such as short bowel syndrome (D. G. Burrin, B. Stoll and X. Guan *Domest. Anim. Endocrinol.* 2003, 24, 103-122; K. V. Haderslev, P. B. Jeppesen, B. Hartmann, J. Thulesen, H. A. Sorensen, J. Graff, B. S. Hansen, F. Tofteng, S. S. Poulsen, J. L. Madsen, J. J. Holst, M. Staun and P. B. Mortensen *Scand. J. Gastroenterol.* 2002, 37, 392-398; P. B. Jeppesen *J. Nutr.* 2003, 133, 3721-3724).

Moreover, there is increasing evidence for a role of SST on immune cells and expression of SSTR5 on activated T lymphocytes (T. Talme, J. Ivanoff, M. Hägglund, R. J. J. van Neerven, A. Ivanoff and K. G. Sundqvist *Clin. Exp. Immunol.* 2001, 125, 71-79; D. Ferone, P. M. van Hagen, C. Semino, V. A. Dalm, A. Barreca, A. Colao, S. W. J. Lamberts, F. Minuto and L. J. Hofland *Dig. Liver Dis.* 2004, 36, S68-77; C. E. Ghamrawy, C. Rabourdin-Combe and S. Krantic *Peptides* 1999, 20, 305-311). Consequently, SSTR5 antagonists could also prove valuable in treating diseases characterized by a disturbed immune system, such as inflammatory bowel disease.

SUMMARY OF THE INVENTION

In an embodiment of the present invention, provided is a compound of formula I:

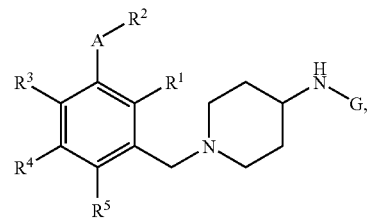

wherein

A is —O— or —NH—;

$R^1$ is selected from the group consisting of hydrogen, $C_{1-7}$-alkoxy and halogen;

$R^2$ is selected from the group consisting of $C_{2-7}$-alkyl, $C_{2-7}$-alkenyl, $C_{3-7}$-alkinyl, $C_{3-7}$-cycloalkyl, halogen-$C_{1-7}$-alkyl, $C_{1-7}$-alkoxy-$C_{1-7}$-alkyl and benzyl;

$R^3$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, $C_{1-7}$-alkoxy-$C_{1-7}$-alkoxy, —O-benzyl, —O—$C_{3-7}$-cycloalkyl, unsubstituted phenyl or phenyl substituted by one to three groups independently selected from $C_{1-7}$-alkyl, halogen and $C_{1-7}$-alkoxy, halogen, halogen-$C_{1-7}$-alkyl, halogen-$C_{1-7}$-alkoxy, amino, pyrrolyl, and —C(O)O$R^6$, wherein $R^6$ is $C_{1-7}$-alkyl;

$R^4$ is selected from the group consisting of hydrogen, hydroxy, $C_{1-7}$-alkoxy, amino, nitro, hydroxy-$C_{1-7}$-alkoxy, $C_{1-7}$-alkoxy-$C_{1-7}$-alkoxy, and —O-benzyl;

or $R^3$ and $R^4$ are bonded to each other to form a ring together with the carbon atoms they are attached to and $R^3$ and $R^4$ together are —O—C(CH$_3$)$_2$—CH=CH—;

$R^5$ is selected from the group consisting of hydrogen, halogen and $C_{1-7}$-alkoxy;

G is selected from the groups

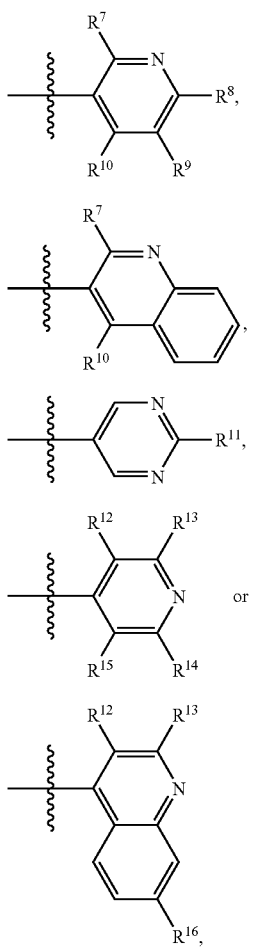

wherein
R$^7$, R$^9$ and R$^{10}$ independently from each other are hydrogen or C$_{1-7}$-alkyl;
R$^8$ is selected from the group consisting of hydrogen, amino,
  heterocyclyl selected from the group consisting of pyrrolidinyl, piperidinyl, piperazinyl and morpholinyl, and
  —NH—C(O)—R$^{15}$, wherein R$^{15}$ is C$_{1-7}$-alkyl;
R$^{11}$ is selected from the group consisting of hydrogen, C$_{1-7}$-alkyl,
  phenyl, and heterocyclyl selected from the group consisting of pyrrolidinyl, piperidinyl, piperazinyl and morpholinyl;
R$^{12}$, R$^{13}$, R$^{14}$ and R$^{15}$ independently from each other are selected from the group consisting of hydrogen, C$_{1-7}$-alkyl, halogen and halogen-C$_{1-7}$-alkyl; and
R$^{16}$ is hydrogen or halogen.

In another embodiment of the present invention, provided is a process for the manufacture of a compound according to formula I, comprising the steps of:
a) reacting a compound of the general formula

G-X    II wherein G is as defined for formula I and X is a leaving group, with a compound of the formula

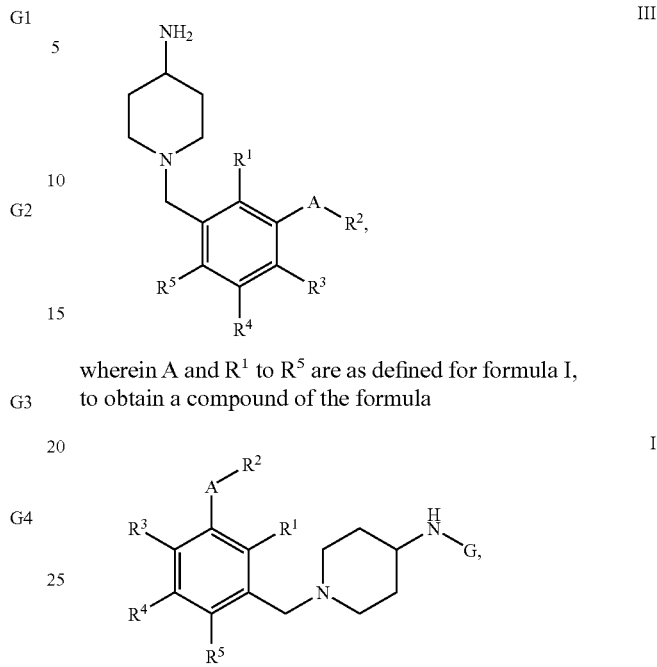

wherein A and R$^1$ to R$^5$ are as defined for formula I, to obtain a compound of the formula

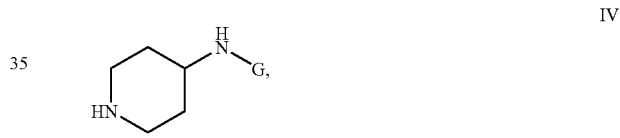

and, if desired, converting the compound of formula I into a pharmaceutically acceptable salt; or, alternatively,
b) reacting a compound of the general formula

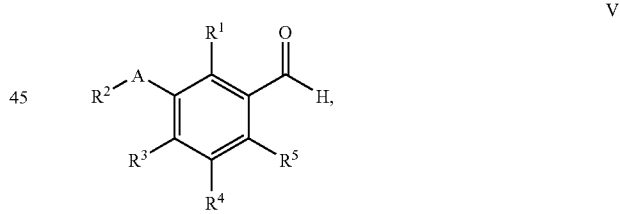

wherein G is as defined for formula I,
with an aldehyde of the formula

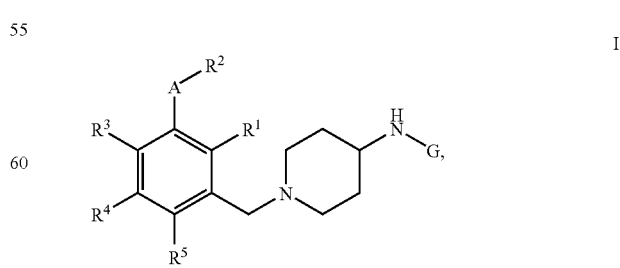

wherein A and R$^1$ to R$^5$ are as defined for formula I,
by employing a reducing agent to obtain a compound of the formula

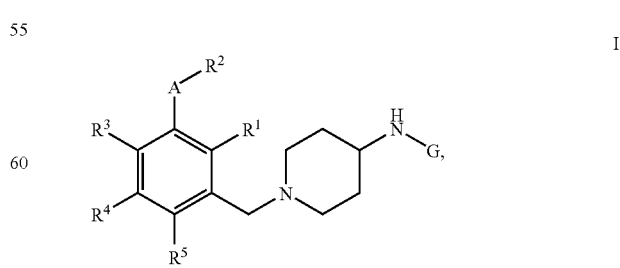

and, if desired, converting the compound of formula I into a pharmaceutically acceptable salt; or, alternatively, c) alkylating a compound of the general formula

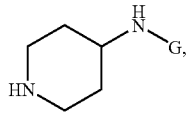
IV wherein G is as defined for formula I,
with a compound of the formula

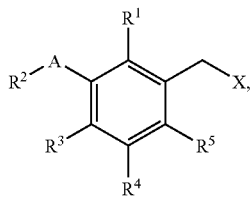
VI wherein A and $R^1$ to $R^5$ are as defined for formula I and X is a leaving group,
under basic conditions to obtain a compound or formula

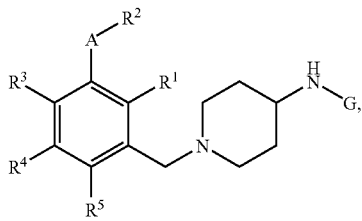
I and, if desired, converting the compound of formula I into a pharmaceutically acceptable salt; or, alternatively, d) reacting a compound of the general formula

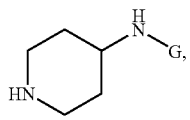
IV wherein G is as defined for formula I,
with a compound of the formula

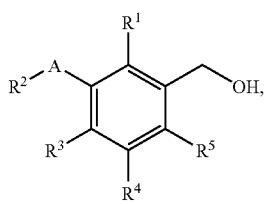
VII wherein A and $R^1$ to $R^5$ are as defined for formula I, in the presence of a trialkylphosphine and a diazo-compound to obtain a compound or formula

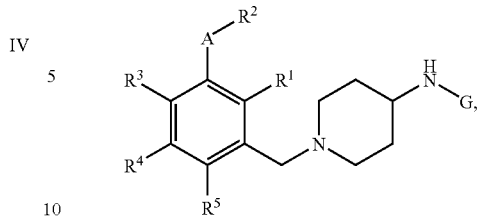
I and, if desired, converting the compound of formula I into a pharmaceutically acceptable salt.

In a further embodiment of the present invention, provided is a pharmaceutical composition, comprising a therapeutically effective amount of a compound according to formula I as well as a pharmaceutically acceptable carrier and/or adjuvant.

In a yet another embodiment of the present invention, provided is a method for the treatment of diseases which are associated with the modulation of SST receptors subtype 5, comprising the step of administering a therapeutically effective amount of a compound according to formula I to a human being or animal in need thereof.

DETAILED DESCRIPTION

The present invention provides for selective, directly acting SSTR5 antagonists. Such antagonists are useful as therapeutically active substances, particularly in the treatment and/or prevention of diseases which are associated with the modulation of SST receptors subtype 5.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination, signifies a straight-chain or branched-chain alkyl group with 1 to 7 carbon atoms, preferably a straight or branched-chain alkyl group with 1 to 4 carbon atoms. Examples of straight-chain and branched $C_1$-$C_7$ alkyl groups are methyl, ethyl, propyl, isopropyl, butyl, isobutyl, tert-butyl, the isomeric pentyls, the isomeric hexyls and the isomeric heptyls, preferably methyl, ethyl and isopropyl, and most preferred the groups specifically exemplified herein.

The term "lower alkenyl" or "$C_{2-7}$-alkenyl", alone or in combination, signifies a straight-chain or branched hydrocarbon residue comprising an olefinic bond and up to 7, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl (allyl).

The term "lower alkinyl" or "$C_{3-7}$-alkinyl" signifies a straight-chain or branched hydrocarbon residue comprising a triple bond and up to 7, preferably up to 6, particularly preferred up to 4 carbon atoms. Examples of alkinyl groups are 2-propinyl, 2-butinyl and 3-butinyl. A preferred example is 2-propinyl.

The term "cycloalkyl" or "$C_{3-7}$-cycloalkyl" refers to a monovalent carbocyclic radical of three to seven, preferably three to five carbon atoms. This term is further exemplified by radicals such as cyclopropyl, cyclobutyl, cyclopentyl, cyclohexyl and cycloheptyl, with cyclobutyl being especially preferred.

The term "alkoxy" refers to the group R'—O—, wherein R' is alkyl. The term "lower alkoxy" or "$C_{1-7}$-alkoxy" refers to the group R'—O—, wherein R' is lower alkyl and the term "lower alkyl" has the previously given significance. Examples of lower alkoxy groups are e.g., methoxy, ethoxy, n-propoxy, isopropoxy, n-butoxy, iso-butoxy, sec-butoxy and tert-butoxy, preferably methoxy and ethoxy and most preferred the groups specifically exemplified herein.

The term "lower alkoxyalkyl" or "$C_{1-7}$-alkoxy-$C_{1-7}$-alkyl" refers to lower alkyl groups as defined above wherein at least one of the hydrogen atoms of the lower alkyl group is replaced by an alkoxy group as defined above. Among the preferred lower alkoxyalkyl groups are methoxymethyl, methoxyethyl and ethoxymethyl.

The term "lower alkoxyalkoxy" or "$C_{1-7}$-alkoxy-$C_{1-7}$-alkoxy" refers to lower alkoxy groups as defined above wherein at least one of the hydrogen atoms of the lower alkoxy group is replaced by an alkoxy group as defined above. Among the preferred lower alkoxyalkoxy groups are 2-methoxy-ethoxy and 3-methoxy-propoxy.

The term "halogen" refers to fluorine, chlorine, bromine and iodine, with fluorine, chlorine and bromine being preferred.

The term "lower halogenalkyl" or "halogen-$C_{1-7}$-alkyl" refers to lower alkyl groups as defined above wherein at least one of the hydrogen atoms of the lower alkyl group is replaced by a halogen atom, preferably fluoro or chloro, most preferably fluoro. Among the preferred
halogenated lower alkyl groups are trifluoromethyl, difluoromethyl, difluoroethyl, fluoromethyl and chloromethyl, with trifluoromethyl and difluoroethyl being especially preferred.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluoromethoxy and chloromethoxy, with trifluoromethoxy being especially preferred.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl, but also groups having two hydroxy groups such as 2-hydroxy-1-hydroxymethyl-ethyl.

The term "lower hydroxyalkoxy" or "hydroxy-$C_{1-7}$-alkoxy" refers to lower alkoxy groups as defined above wherein at least one of the hydrogen atoms of the lower alkoxy group is replaced by a hydroxy group. Examples of lower hydroxyalkoxy groups are hydroxymethoxy or hydroxyethoxy.

The term "heterocyclyl" in general refers to a saturated or partly unsaturated ring which can comprise one, two or three atoms selected from nitrogen, oxygen and/or sulphur. Examples of heterocyclyl rings include aziridinyl, azetidinyl, pyrrolidinyl, piperidinyl, tetrahydropyridyl, azepinyl, piperazinyl, pyrazolidinyl, imidazolinyl, imidazolidinyl, oxazolidinyl, isoxazolidinyl, morpholinyl, thiazolidinyl, isothiazolidinyl, thiadiazolylidinyl, dihydrofuryl, tetrahydrofuryl, oxiranyl, oxetanyl, dihydropyranyl, tetrahydropyranyl and thiomorpholinyl. Preferred heterocyclyl groups are pyrrolidinyl, piperidinyl, piperazinyl and morpholinyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g., hydrated. The solvation can be effected in the course of the manufacturing process or can take place, e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers.

A carbon atom bonded to four nonidentical substituents is termed a "chiral center".

In detail, the present invention relates to compounds of the general formula I

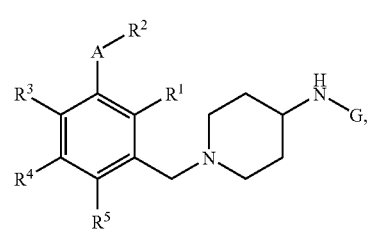

wherein
A is —O— or —NH—;
R$^1$ is selected from the group consisting of hydrogen, $C_{1-7}$-alkoxy and halogen;
R$^2$ is selected from the group consisting of $C_{2-7}$-alkyl, $C_{2-7}$-alkenyl, $C_{3-7}$-alkinyl, $C_{3-7}$-cycloalkyl, halogen-$C_{1-7}$-alkyl, $C_{1-7}$-alkoxy-$C_{1-7}$-alkyl and benzyl;
R$^3$ is selected from the group consisting of hydrogen, $C_{1-7}$-alkyl,
  hydroxy, $C_{1-7}$-alkoxy, $C_{2-7}$-alkenyloxy,
  hydroxy-$C_{1-7}$-alkoxy, $C_{1-7}$-alkoxy-$C_{1-7}$-alkoxy,
  —O-benzyl, —O—$C_{3-7}$-cycloalkyl, unsubstituted phenyl or phenyl substituted by one to three groups independently selected from $C_{1-7}$-alkyl, halogen and $C_{1-7}$-alkoxy, halogen, halogen-$C_{1-7}$-alkyl, halogen-$C_{1-7}$-alkoxy, amino, pyrrolyl, and —C(O)OR$^6$, wherein R$^6$ is $C_{1-7}$-alkyl;

R$^4$ is selected from the group consisting of hydrogen, hydroxy, $C_{1-7}$-alkoxy, amino, nitro, hydroxy-$C_{1-7}$-alkoxy, $C_{1-7}$-alkoxy-$C_{1-7}$-alkoxy and —O-benzyl;

or R$^3$ and R$^4$ are bonded to each other to form a ring together with the carbon atoms they are attached to and R$^3$ and R$^4$ together are —O—C(CH$_3$)$_2$—CH═CH—;

R$^5$ is selected from the group consisting of hydrogen, halogen and $C_{1-7}$-alkoxy;

G is selected from the groups

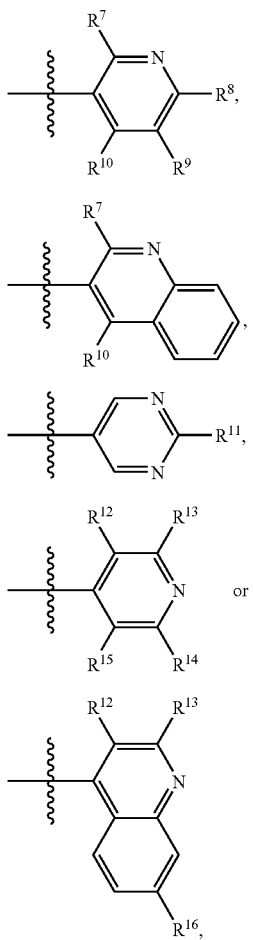

wherein

R$^7$, R$^9$ and R$^{10}$ independently from each other are hydrogen or $C_{1-7}$-alkyl;

R$^8$ is selected from the group consisting of hydrogen, amino, heterocyclyl selected from the group consisting of pyrrolidinyl, piperidinyl, piperazinyl and morpholinyl, and —NH—C(O)—R$^{15}$, wherein R$^{15}$ is $C_{1-7}$alkyl;

R$^{11}$ is selected from the group consisting of hydrogen, $C_{1-7}$-alkyl, phenyl, and heterocyclyl selected from the group consisting of pyrrolidinyl, piperidinyl, piperazinyl and morpholinyl;

R$^{12}$, R$^{13}$, R$^{14}$ and R$^{15}$ independently from each other are selected from the group consisting of hydrogen, $C_{1-7}$-alkyl, halogen and halogen-$C_{1-7}$-alkyl;

R$^{16}$ is hydrogen or halogen;

and pharmaceutically acceptable salts thereof.

Preferred compounds of formula I of the present invention are also those, wherein A is O.

A further group of compounds of formula I are those, wherein A is NH.

Furthermore, compounds of formula I according to the present invention are preferred, wherein R$^1$ is hydrogen.

Also preferred are compounds of formula I according to the invention, wherein R$^2$ is selected from the group consisting of $C_{2-7}$-alkyl, $C_{2-7}$-alkenyl, $C_{3-7}$-alkinyl, $C_{3-7}$-cycloalkyl and halogen-$C_{1-7}$-alkyl. Especially preferred are those compounds of formula I, wherein R$^2$ is selected from the group consisting of ethyl, propyl, isopropyl, allyl, 2-fluoroethyl, butyl, isobutyl, cyclopentyl and 2-propynyl, with those compounds, wherein R$^2$ is ethyl or isopropyl, being most preferred.

Further preferred compounds of formula I according to the present invention are those, wherein R$^3$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, —O-benzyl, —O—$C_{3-7}$-cycloalkyl, phenyl substituted by halogen, halogen, halogen-$C_{1-7}$-alkoxy, amino, pyrrolyl, and —C(O)OR$^6$, wherein R$^6$ is $C_{1-7}$-alkyl.

More preferred are those compounds of formula I, wherein R$^3$ is selected from the group consisting of hydrogen, $C_{1-7}$-alkoxy, halogen, halogen-$C_{1-7}$-alkoxy and pyrrolyl, with those compounds, wherein R$^3$ is halogen, being especially preferred. Most preferably, R$^3$ is chloro.

Furthermore, compounds of formula I of the present invention are preferred, wherein R$^4$ is selected from the group consisting of hydrogen, hydroxy and $C_{1-7}$-alkoxy.

Another group of preferred compounds of formula I according to the present invention are those, wherein R$^3$ and R$^4$ are bonded to each other to form a ring together with the carbon atoms they are attached to and R$^3$ and R$^4$ together are —O—C(CH$_3$)$_2$—CH═CH—. These are compounds of the formula Ix:

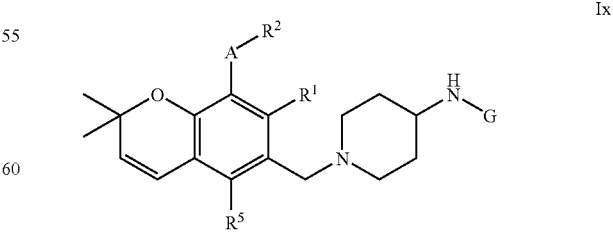

Ix

Furthermore, compounds of formula I according to the invention are preferred, wherein R$^5$ is hydrogen.

Especially preferred are compounds of formula I according to the present invention, wherein G is

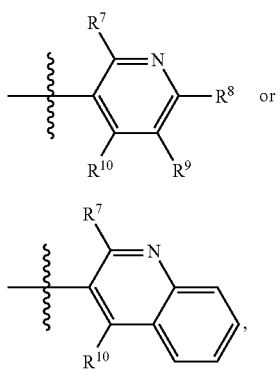
G1 or

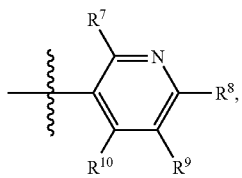
G2 and wherein
$R^7$, $R^9$ and $R^{10}$ independently from each other are hydrogen or $C_{1-7}$-alkyl; and
$R^8$ is selected from the group consisting of hydrogen, amino, heterocyclyl selected from the group consisting of pyrrolidinyl, piperidinyl, piperazinyl and morpholinyl, and —NH—C(O)—$R^{15}$, wherein $R^{15}$ is $C_{1-7}$-alkyl.

Within this group, those compounds are preferred, wherein G is

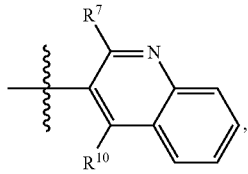
G1 and wherein
$R^7$, $R^9$ and $R^{10}$ independently from each other are hydrogen or $C_{1-7}$-alkyl; and
$R^8$ is selected from the group consisting of hydrogen, amino, heterocyclyl selected from the group consisting of pyrrolidinyl, piperidinyl, piperazinyl and morpholinyl, and —NH—C(O)—$R^{15}$, wherein $R^{15}$ is $C_{1-7}$-alkyl.

Especially preferred are those compounds of formula I, wherein $R^7$, $R^8$, $R^9$ and $R^{10}$ are hydrogen.

Another group of preferred compounds of formula I according to the invention are those, wherein G is

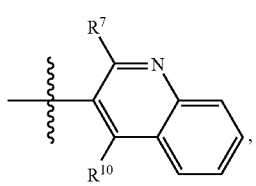
G2 and wherein $R^7$ and $R^{10}$ independently from each other are hydrogen or $C_{1-7}$-alkyl, with those compounds being more preferred, wherein $R^7$ and $R^{10}$ are hydrogen.

A further group of preferred compounds of formula I are those, wherein G is

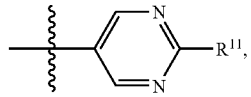
G3 and wherein $R^{11}$ is selected from the group consisting of hydrogen, $C_{1-7}$-alkyl, phenyl, and heterocyclyl selected from the group consisting of pyrrolidinyl, piperidinyl, piperazinyl and morpholinyl. Within this group, those compounds are especially preferred, wherein $R^{11}$ is phenyl.

Also preferred are compounds of formula I of the present invention, wherein G is

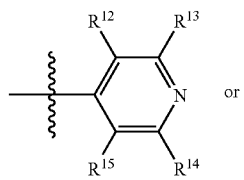
G4 or

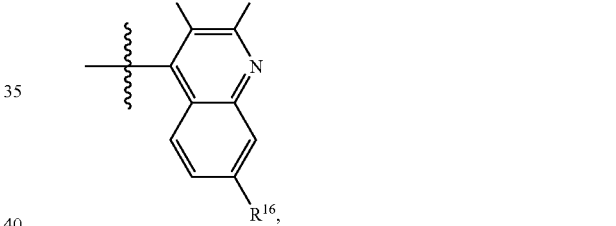
G5 and wherein
$R^{12}$, $R^{13}$, $R^{14}$ and $R^{15}$ independently from each other are selected from the group consisting of hydrogen, $C_{1-7}$-alkyl, halogen and halogen-$C_{1-7}$-alkyl; and
$R^{16}$ is hydrogen or halogen.

Within this group, those compounds of formula I are preferred, wherein G is

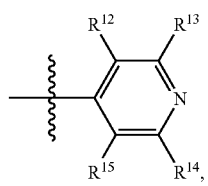
G4 and wherein $R^{12}$, $R^{13}$, $R^{14}$ and $R^{15}$ independently from each other are selected from the group consisting of hydrogen, $C_{1-7}$-alkyl, halogen and halogen-$C_{1-7}$-alkyl. More preferably, three of $R^{12}$, $R^{13}$, $R^{14}$ and $R^{15}$ are hydrogen and one of $R^{12}$, $R^{13}$, $R^{14}$ and $R^{15}$ is selected from the group consisting of hydrogen, $C_{1-7}$-alkyl, halogen and halogen-$C_{1-7}$-alkyl.

Furthermore, compounds of formula I according to the invention are preferred, wherein G is

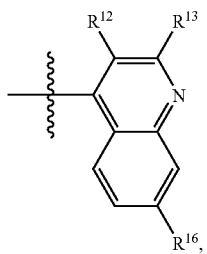

and wherein $R^{12}$ and $R^{13}$ independently from each other are selected from the group consisting of hydrogen, $C_{1-7}$-alkyl, halogen and halogen-$C_{1-7}$-alkyl, and $R^{16}$ is hydrogen or halogen. More preferably, $R^{12}$ and $R^{13}$ are hydrogen.

Examples of preferred compounds of formula I are the following:

[1-(3-ethoxy-4-methyl-benzyl)-piperidin-4-yl]-pyridin-3-yl-amine,
[1-(3-ethoxy-4-fluoro-benzyl)-piperidin-4-yl]-pyridin-3-yl-amine,
[1-(4-chloro-3-ethoxy-benzyl)-piperidin-4-yl]-pyridin-3-yl-amine,
[1-(3-ethoxy-4-methoxy-benzyl)-piperidin-4-yl]-pyridin-3-yl-amine,
[1-(4-allyloxy-3-ethoxy-benzyl)-piperidin-4-yl]-pyridin-3-yl-amine,
[1-(3-ethoxy-4-isobutoxy-benzyl)-piperidin-4-yl]-pyridin-3-yl-amine,
{1-[3-ethoxy-4-(1-ethyl-propoxy)-benzyl]-piperidin-4-yl}-pyridin-3-yl-amine,
[1-(4-cyclopentyloxy-3-ethoxy-benzyl)-piperidin-4-yl]-pyridin-3-yl-amine,
[1-(4-benzyloxy-3-ethoxy-benzyl)-piperidin-4-yl]-pyridin-3-yl-amine,
[1-(4-difluoromethoxy-3-ethoxy-benzyl)-piperidin-4-yl]-pyridin-3-yl-amine,
[1-(4-methoxy-3-propoxy-benzyl)-piperidin-4-yl]-pyridin-3-yl-amine,
[1-(3-allyloxy-4-methoxy-benzyl)-piperidin-4-yl]-pyridin-3-yl-amine,
[1-(3-butoxy-4-methoxy-benzyl)-piperidin-4-yl]-pyridin-3-yl-amine,
[1-(3-isobutoxy-4-methoxy-benzyl)-piperidin-4-yl]-pyridin-3-yl-amine,
[1-(3-cyclopentyloxy-4-methoxy-benzyl)-piperidin-4-yl]-pyridin-3-yl-amine,
[1-(8-ethoxy-2,2-dimethyl-2H-chromen-6-ylmethyl)-piperidin-4-yl]-pyridin-3-yl-amine,
[1-(3,5-diethoxy-benzyl)-piperidin-4-yl]-pyridin-3-yl-amine,
[1-(3,5-diisopropoxy-benzyl)-piperidin-4-yl]-pyridin-3-yl-amine,
2,6-diethoxy-4-[4-(pyridin-3-ylamino)-piperidin-1-ylmethyl]-benzoic acid ethyl ester,
[1-(3,5-diethoxy-4-fluoro-benzyl)-piperidin-4-yl]-pyridin-3-yl-amine,
[1-(4-chloro-3,5-diethoxy-benzyl)-piperidin-4-yl]-pyridin-3-yl-amine,
[1-(4-bromo-3,5-diethoxy-benzyl)-piperidin-4-yl]-pyridin-3-yl-amine,
[1-(3,5-diethoxy-4-pyrrol-1-yl-benzyl)-piperidin-4-yl]-pyridin-3-yl-amine,
[1-(3-ethoxy-4-fluoro-benzyl)-piperidin-4-yl]-(6-morpholin-4-yl-pyridin-3-yl)-amine,
[1-(4-chloro-3-ethoxy-benzyl)-piperidin-4-yl]-(6-morpholin-4-yl-pyridin-3-yl)-amine,
[1-(3-ethoxy-4-methoxy-benzyl)-piperidin-4-yl]-(6-morpholin-4-yl-pyridin-3-yl)-amine,
[1-(4-cyclopentyloxy-3-ethoxy-benzyl)-piperidin-4-yl]-(6-morpholin-4-yl-pyridin-3-yl)-amine,
[1-(4-benzyloxy-3-ethoxy-benzyl)-piperidin-4-yl]-(6-morpholin-4-yl-pyridin-3-yl)-amine,
[1-(4-difluoromethoxy-3-ethoxy-benzyl)-piperidin-4-yl]-(6-morpholin-4-yl-pyridin-3-yl)-amine,
[1-(4-methoxy-3-propoxy-benzyl)-piperidin-4-yl]-(6-morpholin-4-yl-pyridin-3-yl)-amine,
[1-(3-isopropoxy-4-methoxy-benzyl)-piperidin-4-yl]-(6-morpholin-4-yl-pyridin-3-yl)-amine,
{1-[3-(2-fluoro-ethoxy)-4-methoxy-benzyl]-piperidin-4-yl}-(6-morpholin-4-yl-pyridin-3-yl)-amine,
[1-(3-allyloxy-4-methoxy-benzyl)-piperidin-4-yl]-(6-morpholin-4-yl-pyridin-3-yl)-amine,
[1-(3-isobutoxy-4-methoxy-benzyl)-piperidin-4-yl]-(6-morpholin-4-yl-pyridin-3-yl)-amine,
[1-(3-cyclopentyloxy-4-methoxy-benzyl)-piperidin-4-yl]-(6-morpholin-4-yl-pyridin-3-yl)-amine,
[1-(8-ethoxy-2,2-dimethyl-2H-chromen-6-ylmethyl)-piperidin-4-yl]-(6-morpholin-4-yl-pyridin-3-yl)-amine,
[1-(3,5-diethoxy-benzyl)-piperidin-4-yl]-(6-morpholin-4-yl-pyridin-3-yl)-amine,
[1-(3,5-diisopropoxy-benzyl)-piperidin-4-yl]-(6-morpholin-4-yl-pyridin-3-yl)-amine,
[1-(3,5-diethoxy-4-fluoro-benzyl)-piperidin-4-yl]-(6-morpholin-4-yl-pyridin-3-yl)-amine,
[1-(4-chloro-3,5-diethoxy-benzyl)-piperidin-4-yl]-(6-morpholin-4-yl-pyridin-3-yl)-amine,
[1-(4-bromo-3,5-diethoxy-benzyl)-piperidin-4-yl]-(6-morpholin-4-yl-pyridin-3-yl)-amine,
[1-(4-amino-3,5-diethoxy-benzyl)-piperidin-4-yl]-(6-morpholin-4-yl-pyridin-3-yl)-amine,
[1-(3,5-diethoxy-4-pyrrol-1-yl-benzyl)-piperidin-4-yl]-(6-morpholin-4-yl-pyridin-3-yl)-amine,
[1-(2,6-diethoxy-4'-fluoro-biphenyl-4-ylmethyl)-piperidin-4-yl]-(6-morpholin-4-yl-pyridin-3-yl)-amine,
N-{5-[1-(3-ethoxy-4-fluoro-benzyl)-piperidin-4-ylamino]-pyridin-2-yl}-acetamide,
N-{5-[1-(4-chloro-3-ethoxy-benzyl)-piperidin-4-ylamino]-pyridin-2-yl}-acetamide,
N-{5-[1-(3-ethoxy-4-methoxy-benzyl)-piperidin-4-ylamino]-pyridin-2-yl}-acetamide,
N-{5-[1-(4-cyclopentyloxy-3-ethoxy-benzyl)-piperidin-4-ylamino]-pyridin-2-yl}-acetamide,
N-{5-[1-(4-benzyloxy-3-ethoxy-benzyl)-piperidin-4-ylamino]-pyridin-2-yl}-acetamide,
N-{5-[1-(4-difluoromethoxy-3-ethoxy-benzyl)-piperidin-4-ylamino]-pyridin-2-yl}-acetamide,
N-{5-[1-(4-methoxy-3-propoxy-benzyl)-piperidin-4-ylamino]-pyridin-2-yl}-acetamide,
N-{5-[1-(3-isopropoxy-4-methoxy-benzyl)-piperidin-4-ylamino]-pyridin-2-yl}-acetamide,
N-{5-[1-(3-isobutoxy-4-methoxy-benzyl)-piperidin-4-ylamino]-pyridin-2-yl}-acetamide,
N-{5-[1-(3-cyclopentyloxy-4-methoxy-benzyl)-piperidin-4-ylamino]-pyridin-2-yl}-acetamide,
N-{5-[1-(8-ethoxy-2,2-dimethyl-2H-chromen-6-ylmethyl)-piperidin-4-ylamino]-pyridin-2-yl}-acetamide, N-{5-[1-(3,5-diethoxy-benzyl)-piperidin-4-ylamino]-pyridin-2-yl}-acetamide,
N-{5-[1-(3,5-diisopropoxy-benzyl)-piperidin-4-ylamino]-pyridin-2-yl}-acetamide,
N-{5-[1-(3,5-diethoxy-4-fluoro-benzyl)-piperidin-4-ylamino]-pyridin-2-yl}-acetamide,
N-{5-[1-(4-chloro-3,5-diethoxy-benzyl)-piperidin-4-ylamino]-pyridin-2-yl}-acetamide,
N-{5-[1-(4-bromo-3,5-diethoxy-benzyl)-piperidin-4-ylamino]-pyridin-2-yl}-acetamide,
N-{5-[1-(4-amino-3,5-diethoxy-benzyl)-piperidin-4-ylamino]-pyridin-2-yl}-acetamide,
N-{5-[1-(3,5-diethoxy-4-pyrrol-1-yl-benzyl)-piperidin-4-ylamino]-pyridin-2-yl}-acetamide,
N-{5-[1-(2,6-diethoxy-4'-fluoro-biphenyl-4-ylmethyl)-piperidin-4-ylamino]-pyridin-2-yl}-acetamide,
$N^5$-[1-(3-ethoxy-4-fluoro-benzyl)-piperidin-4-yl]-3-methyl-pyridine-2,5-diamine,
$N^5$-[1-(4-chloro-3-ethoxy-benzyl)-piperidin-4-yl]-3-methyl-pyridine-2,5-diamine,
$N^5$-[1-(3-ethoxy-4-methoxy-benzyl)-piperidin-4-yl]-3-methyl-pyridine-2,5-diamine,
$N^5$-[1-(3-ethoxy-4-isopropoxy-benzyl)-piperidin-4-yl]-3-methyl-pyridine-2,5-diamine,
$N^5$-[1-(4-difluoromethoxy-3-ethoxy-benzyl)-piperidin-4-yl]-3-methyl-pyridine-2,5-diamine,
$N^5$-[1-(4-methoxy-3-propoxy-benzyl)-piperidin-4-yl]-3-methyl-pyridine-2,5-diamine,
$N^5$-[1-(3-isopropoxy-4-methoxy-benzyl)-piperidin-4-yl]-3-methyl-pyridine-2,5-diamine,
$N^5$-[1-(3-allyloxy-4-methoxy-benzyl)-piperidin-4-yl]-3-methyl-pyridine-2,5-diamine,
$N^5$-[1-(3-isobutoxy-4-methoxy-benzyl)-piperidin-4-yl]-3-methyl-pyridine-2,5-diamine,
$N^5$-[1-(3-cyclopentyloxy-4-methoxy-benzyl)-piperidin-4-yl]-3-methyl-pyridine-2,5-diamine,
$N^5$-[1-(3,5-diethoxy-benzyl)-piperidin-4-yl]-3-methyl-pyridine-2,5-diamine,
$N^5$-[1-(3,5-diisopropoxy-benzyl)-piperidin-4-yl]-3-methyl-pyridine-2,5-diamine,
4-[4-(6-amino-5-methyl-pyridin-3-ylamino)-piperidin-1-ylmethyl]-2,6-diethoxy-benzoic acid ethyl ester,
$N^5$-[1-(3,5-diethoxy-4-fluoro-benzyl)-piperidin-4-yl]-3-methyl-pyridine-2,5-diamine,
$N^5$-[1-(3,5-diethoxy-4-pyrrol-1-yl-benzyl)-piperidin-4-yl]-3-methyl-pyridine-2,5-diamine,
$N^5$-[1-(2,6-diethoxy-4'-fluoro-biphenyl-4-ylmethyl)-piperidin-4-yl]-3-methyl-pyridine-2,5-diamine,
N-{5-[1-(4-chloro-3-ethoxy-benzyl)-piperidin-4-ylamino]-6-methyl-pyridin-2-yl}-acetamide,
N-{5-[1-(3-isobutoxy-4-methoxy-benzyl)-piperidin-4-ylamino]-6-methyl-pyridin-2-yl}-acetamide,
N-{5-[1-(3,5-diisopropoxy-benzyl)-piperidin-4-ylamino]-6-methyl-pyridin-2-yl}-acetamide,
N-{5-[1-(3,5-diethoxy-4-fluoro-benzyl)-piperidin-4-ylamino]-6-methyl-pyridin-2-yl}-acetamide,
N-{5-[1-(4-chloro-3,5-diethoxy-benzyl)-piperidin-4-ylamino]-6-methyl-pyridin-2-yl}-acetamide,
N-{5-[1-(4-amino-3,5-diethoxy-benzyl)-piperidin-4-ylamino]-6-methyl-pyridin-2-yl}-acetamide,
N-{5-[1-(3,5-diethoxy-4-pyrrol-1-yl-benzyl)-piperidin-4-ylamino]-6-methyl-pyridin-2-yl}-acetamide,
N-{5-[1-(2,6-diethoxy-4'-fluoro-biphenyl-4-ylmethyl)-piperidin-4-ylamino]-6-methyl-pyridin-2-yl}-acetamide,
[1-(3-ethoxy-4-fluoro-benzyl)-piperidin-4-yl]-quinolin-3-yl-amine,
[1-(4-chloro-3-ethoxy-benzyl)-piperidin-4-yl]-quinolin-3-yl-amine,
2-ethoxy-4-[4-(quinolin-3-ylamino)-piperidin-1-ylmethyl]-phenol,
[1-(3-ethoxy-4-methoxy-benzyl)-piperidin-4-yl]-quinolin-3-yl-amine,
[1-(3,4-diethoxy-benzyl)-piperidin-4-yl]-quinolin-3-yl-amine,
[1-(4-allyloxy-3-ethoxy-benzyl)-piperidin-4-yl]-quinolin-3-yl-amine,
[1-(3-ethoxy-4-isopropoxy-benzyl)-piperidin-4-yl]-quinolin-3-yl-amine,
[1-(3-ethoxy-4-isobutoxy-benzyl)-piperidin-4-yl]-quinolin-3-yl-amine,
{1-[3-ethoxy-4-(1-ethyl-propoxy)-benzyl]-piperidin-4-yl}-quinolin-3-yl-amine,
[1-(4-cyclopentyloxy-3-ethoxy-benzyl)-piperidin-4-yl]-quinolin-3-yl-amine,
[1-(4-benzyloxy-3-ethoxy-benzyl)-piperidin-4-yl]-quinolin-3-yl-amine,
[1-(4-difluoromethoxy-3-ethoxy-benzyl)-piperidin-4-yl]-quinolin-3-yl-amine,
[1-(4-methoxy-3-propoxy-benzyl)-piperidin-4-yl]-quinolin-3-yl-amine,
[1-(3-isopropoxy-4-methoxy-benzyl)-piperidin-4-yl]-quinolin-3-yl-amine,
{1-[3-(2-fluoro-ethoxy)-4-methoxy-benzyl]-piperidin-4-yl}-quinolin-3-yl-amine,
[1-(3-allyloxy-4-methoxy-benzyl)-piperidin-4-yl]-quinolin-3-yl-amine,
[1-(4-methoxy-3-prop-2-ynyloxy-benzyl)-piperidin-4-yl]-quinolin-3-yl-amine,
[1-(3-butoxy-4-methoxy-benzyl)-piperidin-4-yl]-quinolin-3-yl-amine,
[1-(3-isobutoxy-4-methoxy-benzyl)-piperidin-4-yl]-quinolin-3-yl-amine,
[1-(3-cyclopentyloxy-4-methoxy-benzyl)-piperidin-4-yl]-quinolin-3-yl-amine,
2-{2-ethoxy-5-fluoro-4-[4-(quinolin-3-ylamino)-piperidin-1-ylmethyl]-phenoxy}-ethanol,
[1-(8-ethoxy-2,2-dimethyl-2H-chromen-6-ylmethyl)-piperidin-4-yl]-quinolin-3-yl-amine,
[1-(3,5-diethoxy-benzyl)-piperidin-4-yl]-quinolin-3-yl-amine,
[1-(3,5-diisopropoxy-benzyl)-piperidin-4-yl]-quinolin-3-yl-amine,
2,6-diethoxy-4-[4-(quinolin-3-ylamino)-piperidin-1-ylmethyl]-benzoic acid ethyl ester,
[1-(3,5-diethoxy-4-fluoro-benzyl)-piperidin-4-yl]-quinolin-3-yl-amine,
[1-(4-chloro-3,5-diethoxy-benzyl)-piperidin-4-yl]-quinolin-3-yl-amine,
[1-(4-bromo-3,5-diethoxy-benzyl)-piperidin-4-yl]-quinolin-3-yl-amine,
[1-(4-amino-3,5-diethoxy-benzyl)-piperidin-4-yl]-quinolin-3-yl-amine,
[1-(3,5-diethoxy-4-pyrrol-1-yl-benzyl)-piperidin-4-yl]-quinolin-3-yl-amine,
[1-(2,6-diethoxy-4'-fluoro-biphenyl-4-ylmethyl)-piperidin-4-yl]-quinolin-3-yl-amine,
[1-(3-ethoxy-4-fluoro-benzyl)-piperidin-4-yl]-(2-methyl-pyridin-4-yl)-amine,
[1-(4-chloro-3-ethoxy-benzyl)-piperidin-4-yl]-(2-methyl-pyridin-4-yl)-amine,
[1-(3-ethoxy-4-methoxy-benzyl)-piperidin-4-yl]-(2-methyl-pyridin-4-yl)-amine,

[1-(3-ethoxy-4-isobutoxy-benzyl)-piperidin-4-yl]-(2-methyl-pyridin-4-yl)-amine,
[1-(4-cyclopentyloxy-3-ethoxy-benzyl)-piperidin-4-yl]-(2-methyl-pyridin-4-yl)-amine,
[1-(4-benzyloxy-3-ethoxy-benzyl)-piperidin-4-yl]-(2-methyl-pyridin-4-yl)-amine,
[1-(4-difluoromethoxy-3-ethoxy-benzyl)-piperidin-4-yl]-(2-methyl-pyridin-4-yl)-amine,
[1-(4-methoxy-3-propoxy-benzyl)-piperidin-4-yl]-(2-methyl-pyridin-4-yl)-amine,
[1-(3-isobutoxy-4-methoxy-benzyl)-piperidin-4-yl]-(2-methyl-pyridin-4-yl)-amine,
[1-(3-cyclopentyloxy-4-methoxy-benzyl)-piperidin-4-yl]-(2-methyl-pyridin-4-yl)-amine,
[1-(8-ethoxy-2,2-dimethyl-2H-chromen-6-ylmethyl)-piperidin-4-yl]-(2-methyl-pyridin-4-yl)-amine,
[1-(3,5-diethoxy-benzyl)-piperidin-4-yl]-(2-methyl-pyridin-4-yl)-amine,
[1-(3,5-diisopropoxy-benzyl)-piperidin-4-yl]-(2-methyl-pyridin-4-yl)-amine,
2,6-diethoxy-4-[4-(2-methyl-pyridin-4-ylamino)-piperidin-1-ylmethyl]-benzoic acid ethyl ester,
[1-(3,5-diethoxy-4-fluoro-benzyl)-piperidin-4-yl]-(2-methyl-pyridin-4-yl)-amine,
[1-(4-chloro-3,5-diethoxy-benzyl)-piperidin-4-yl]-(2-methyl-pyridin-4-yl)-amine,
[1-(4-bromo-3,5-diethoxy-benzyl)-piperidin-4-yl]-(2-methyl-pyridin-4-yl)-amine,
[1-(4-amino-3,5-diethoxy-benzyl)-piperidin-4-yl]-(2-methyl-pyridin-4-yl)-amine,
[1-(3,5-diethoxy-4-pyrrol-1-yl-benzyl)-piperidin-4-yl]-(2-methyl-pyridin-4-yl)-amine,
[1-(2,6-diethoxy-4'-fluoro-biphenyl-4-ylmethyl)-piperidin-4-yl]-(2-methyl-pyridin-4-yl)-amine,
[1-(4-chloro-3-ethoxy-benzyl)-piperidin-4-yl]-(3-fluoro-pyridin-4-yl)-amine,
[1-(4-chloro-3,5-diethoxy-benzyl)-piperidin-4-yl]-(3-fluoro-pyridin-4-yl)-amine,
[1-(4-amino-3,5-diethoxy-benzyl)-piperidin-4-yl]-(3-fluoro-pyridin-4-yl)-amine,
[1-(2,6-diethoxy-4'-fluoro-biphenyl-4-ylmethyl)-piperidin-4-yl]-(3-fluoro-pyridin-4-yl)-amine,
[1-(3-ethoxy-4-fluoro-benzyl)-piperidin-4-yl]-quinolin-4-yl-amine,
[1-(4-chloro-3-ethoxy-benzyl)-piperidin-4-yl]-quinolin-4-yl-amine,
2-ethoxy-4-[4-(quinolin-4-ylamino)-piperidin-1-ylmethyl]-phenol,
[1-(3-ethoxy-4-methoxy-benzyl)-piperidin-4-yl]-quinolin-4-yl-amine,
[1-(3,4-diethoxy-benzyl)-piperidin-4-yl]-quinolin-4-yl-amine,
[1-(4-allyloxy-3-ethoxy-benzyl)-piperidin-4-yl]-quinolin-4-yl-amine,
[1-(3-ethoxy-4-isopropoxy-benzyl)-piperidin-4-yl]-quinolin-4-yl-amine,
[1-(3-ethoxy-4-isobutoxy-benzyl)-piperidin-4-yl]-quinolin-4-yl-amine,
{1-[3-ethoxy-4-(1-ethyl-propoxy)-benzyl]-piperidin-4-yl}-quinolin-4-yl-amine,
[1-(4-cyclopentyloxy-3-ethoxy-benzyl)-piperidin-4-yl]-quinolin-4-yl-amine,
[1-(4-benzyloxy-3-ethoxy-benzyl)-piperidin-4-yl]-quinolin-4-yl-amine,
[1-(4-difluoromethoxy-3-ethoxy-benzyl)-piperidin-4-yl]-quinolin-4-yl-amine,
[1-(4-methoxy-3-propoxy-benzyl)-piperidin-4-yl]-quinolin-4-yl-amine,
[1-(3-isopropoxy-4-methoxy-benzyl)-piperidin-4-yl]-quinolin-4-yl-amine,
{1-[3-(2-fluoro-ethoxy)-4-methoxy-benzyl]-piperidin-4-yl}-quinolin-4-yl-amine,
[1-(3-allyloxy-4-methoxy-benzyl)-piperidin-4-yl]-quinolin-4-yl-amine,
[1-(4-methoxy-3-prop-2-ynyloxy-benzyl)-piperidin-4-yl]-quinolin-4-yl-amine,
[1-(3-butoxy-4-methoxy-benzyl)-piperidin-4-yl]-quinolin-4-yl-amine,
[1-(3-isobutoxy-4-methoxy-benzyl)-piperidin-4-yl]-quinolin-4-yl-amine,
[1-(3-cyclopentyloxy-4-methoxy-benzyl)-piperidin-4-yl]-quinolin-4-yl-amine,
[1-(8-ethoxy-2,2-dimethyl-2H-chromen-6-ylmethyl)-piperidin-4-yl]-quinolin-4-yl-amine,
[1-(3,5-diethoxy-benzyl)-piperidin-4-yl]-quinolin-4-yl-amine,
[1-(3,5-diisopropoxy-benzyl)-piperidin-4-yl]-quinolin-4-yl-amine,
2,6-diethoxy-4-[4-(quinolin-4-ylamino)-piperidin-1-ylmethyl]-benzoic acid ethyl ester,
[1-(3,5-diethoxy-4-fluoro-benzyl)-piperidin-4-yl]-quinolin-4-yl-amine,
[1-(4-chloro-3,5-diethoxy-benzyl)-piperidin-4-yl]-quinolin-4-yl-amine,
[1-(4-bromo-3,5-diethoxy-benzyl)-piperidin-4-yl]-quinolin-4-yl-amine,
[1-(4-amino-3,5-diethoxy-benzyl)-piperidin-4-yl]-quinolin-4-yl-amine,
[1-(3,5-diethoxy-4-pyrrol-1-yl-benzyl)-piperidin-4-yl]-quinolin-4-yl-amine,
[1-(2,6-diethoxy-4'-fluoro-biphenyl-4-ylmethyl)-piperidin-4-yl]-quinolin-4-yl-amine,
(7-chloro-quinolin-4-yl)-[1-(3-ethoxy-4-fluoro-benzyl)-piperidin-4-yl]-amine,
[1-(4-chloro-3-ethoxy-benzyl)-piperidin-4-yl]-(7-chloro-quinolin-4-yl)-amine,
4-[4-(7-chloro-quinolin-4-ylamino)-piperidin-1-ylmethyl]-2-ethoxy-phenol,
(7-chloro-quinolin-4-yl)-[1-(3-ethoxy-4-methoxy-benzyl)-piperidin-4-yl]-amine,
[1-(4-allyloxy-3-ethoxy-benzyl)-piperidin-4-yl]-(7-chloro-quinolin-4-yl)-amine,
(7-chloro-quinolin-4-yl)-[1-(3-ethoxy-4-isopropoxy-benzyl)-piperidin-4-yl]-amine,
(7-chloro-quinolin-4-yl)-[1-(3-ethoxy-4-isobutoxy-benzyl)-piperidin-4-yl]-amine,
(7-chloro-quinolin-4-yl)-{1-[3-ethoxy-4-(1-ethyl-propoxy)-benzyl]-piperidin-4-yl}-amine,
(7-chloro-quinolin-4-yl)-[1-(4-cyclopentyloxy-3-ethoxy-benzyl)-piperidin-4-yl]-amine,
[1-(4-benzyloxy-3-ethoxy-benzyl)-piperidin-4-yl]-(7-chloro-quinolin-4-yl)-amine,
(7-chloro-quinolin-4-yl)-[1-(4-difluoromethoxy-3-ethoxy-benzyl)-piperidin-4-yl]-amine,
(7-chloro-quinolin-4-yl)-[1-(4-methoxy-3-propoxy-benzyl)-piperidin-4-yl]-amine,
(7-chloro-quinolin-4-yl)-[1-(3-isopropoxy-4-methoxy-benzyl)-piperidin-4-yl]-amine,
(7-chloro-quinolin-4-yl)-{1-[3-(2-fluoro-ethoxy)-4-methoxy-benzyl]-piperidin-4-yl}-amine,
[1-(3-allyloxy-4-methoxy-benzyl)-piperidin-4-yl]-(7-chloro-quinolin-4-yl)-amine, (7-chloro-quinolin-4-yl)-[1-(4-methoxy-3-prop-2-ynyloxy-benzyl)-piperidin-4-yl]-amine,
(7-chloro-quinolin-4-yl)-[1-(3-isobutoxy-4-methoxy-benzyl)-piperidin-4-yl]-amine,
(7-chloro-quinolin-4-yl)-[1-(3-cyclopentyloxy-4-methoxy-benzyl)-piperidin-4-yl]-amine,
2-{4-[4-(7-chloro-quinolin-4-ylamino)-piperidin-1-ylmethyl]-2-ethoxy-5-fluoro-phenoxy}-ethanol,
(7-chloro-quinolin-4-yl)-[1-(8-ethoxy-2,2-dimethyl-2H-chromen-6-ylmethyl)-piperidin-4-yl]-amine,
(7-chloro-quinolin-4-yl)-[1-(3,5-diethoxy-benzyl)-piperidin-4-yl]-amine,
(7-chloro-quinolin-4-yl)-[1-(3,5-diisopropoxy-benzyl)-piperidin-4-yl]-amine,
4-[4-(7-chloro-quinolin-4-ylamino)-piperidin-1-ylmethyl]-2,6-diethoxy-benzoic acid ethyl ester,
(7-chloro-quinolin-4-yl)-[1-(3,5-diethoxy-4-fluoro-benzyl)-piperidin-4-yl]-amine,
[1-(4-chloro-3,5-diethoxy-benzyl)-piperidin-4-yl]-(7-chloro-quinolin-4-yl)-amine,
[1-(4-bromo-3,5-diethoxy-benzyl)-piperidin-4-yl]-(7-chloro-quinolin-4-yl)-amine,
(7-chloro-quinolin-4-yl)-[1-(3,5-diethoxy-4-pyrrol-1-yl-benzyl)-piperidin-4-yl]-amine,
(7-chloro-quinolin-4-yl)-[1-(2,6-diethoxy-4'-fluoro-biphenyl-4-ylmethyl)-piperidin-4-yl]-amine,
[1-(4-chloro-3-ethoxy-benzyl)-piperidin-4-yl]-pyrimidin-5-yl-amine,
[1-(3-isobutoxy-4-methoxy-benzyl)-piperidin-4-yl]-pyrimidin-5-yl-amine,
[1-(8-ethoxy-2,2-dimethyl-2H-chromen-6-ylmethyl)-piperidin-4-yl]-pyrimidin-5-yl-amine,
[1-(3,5-diethoxy-benzyl)-piperidin-4-yl]-pyrimidin-5-yl-amine,
3-isopropoxy-5-[4-(pyrimidin-5-ylamino)-piperidin-1-ylmethyl]-phenol,
[1-(3,5-diisopropoxy-benzyl)-piperidin-4-yl]-pyrimidin-5-yl-amine,
[1-(3,5-diethoxy-4-fluoro-benzyl)-piperidin-4-yl]-pyrimidin-5-yl-amine,
[1-(4-chloro-3,5-diethoxy-benzyl)-piperidin-4-yl]-pyrimidin-5-yl-amine,
[1-(4-bromo-3,5-diethoxy-benzyl)-piperidin-4-yl]-pyrimidin-5-yl-amine,
[1-(4-amino-3,5-diethoxy-benzyl)-piperidin-4-yl]-pyrimidin-5-yl-amine,
[1-(3,5-diethoxy-4-pyrrol-1-yl-benzyl)-piperidin-4-yl]-pyrimidin-5-yl-amine,
[1-(3-ethoxy-4-methyl-benzyl)-piperidin-4-yl]-(2-phenyl-pyrimidin-5-yl)-amine,
[1-(3-ethoxy-4-fluoro-benzyl)-piperidin-4-yl]-(2-phenyl-pyrimidin-5-yl)-amine,
[1-(4-chloro-3-ethoxy-benzyl)-piperidin-4-yl]-(2-phenyl-pyrimidin-5-yl)-amine,
[1-(3-ethoxy-4-methoxy-benzyl)-piperidin-4-yl]-(2-phenyl-pyrimidin-5-yl)-amine,
[1-(4-allyloxy-3-ethoxy-benzyl)-piperidin-4-yl]-(2-phenyl-pyrimidin-5-yl)-amine,
[1-(3-ethoxy-4-isobutoxy-benzyl)-piperidin-4-yl]-(2-phenyl-pyrimidin-5-yl)-amine,
{1-[3-ethoxy-4-(1-ethyl-propoxy)-benzyl]-piperidin-4-yl}-(2-phenyl-pyrimidin-5-yl)-amine,
[1-(4-cyclopentyloxy-3-ethoxy-benzyl)-piperidin-4-yl]-(2-phenyl-pyrimidin-5-yl)-amine,
[1-(4-difluoromethoxy-3-ethoxy-benzyl)-piperidin-4-yl]-(2-phenyl-pyrimidin-5-yl)-amine,
[1-(4-methoxy-3-propoxy-benzyl)-piperidin-4-yl]-(2-phenyl-pyrimidin-5-yl)-amine,
[1-(3-isopropoxy-4-methoxy-benzyl)-piperidin-4-yl]-(2-phenyl-pyrimidin-5-yl)-amine,
[1-(3-allyloxy-4-methoxy-benzyl)-piperidin-4-yl]-(2-phenyl-pyrimidin-5-yl)-amine,
[1-(3-butoxy-4-methoxy-benzyl)-piperidin-4-yl]-(2-phenyl-pyrimidin-5-yl)-amine,
[1-(3-isobutoxy-4-methoxy-benzyl)-piperidin-4-yl]-(2-phenyl-pyrimidin-5-yl)-amine,
[1-(3-cyclopentyloxy-4-methoxy-benzyl)-piperidin-4-yl]-(2-phenyl-pyrimidin-5-yl)-amine,
[1-(8-ethoxy-2,2-dimethyl-2H-chromen-6-ylmethyl)-piperidin-4-yl]-(2-phenyl-pyrimidin-5-yl)-amine,
[1-(3,5-diethoxy-benzyl)-piperidin-4-yl]-(2-phenyl-pyrimidin-5-yl)-amine,
2,6-diethoxy-4-[4-(2-phenyl-pyrimidin-5-ylamino)-piperidin-1-ylmethyl]-benzoic acid ethyl ester,
[1-(3,5-diethoxy-4-fluoro-benzyl)-piperidin-4-yl]-(2-phenyl-pyrimidin-5-yl)-amine,
[1-(4-chloro-3,5-diethoxy-benzyl)-piperidin-4-yl]-(2-phenyl-pyrimidin-5-yl)-amine,
[1-(4-bromo-3,5-diethoxy-benzyl)-piperidin-4-yl]-(2-phenyl-pyrimidin-5-yl)-amine,
[1-(3,5-diethoxy-4-pyrrol-1-yl-benzyl)-piperidin-4-yl]-(2-phenyl-pyrimidin-5-yl)-amine,
[1-(2,6-diethoxy-4'-fluoro-biphenyl-4-ylmethyl)-piperidin-4-yl]-(2-phenyl-pyrimidin-5-yl)-amine,
[1-(4-chloro-3-ethoxy-benzyl)-piperidin-4-yl]-(2-morpholin-4-yl-pyrimidin-5-yl)-amine,
[1-(4-chloro-3,5-diethoxy-benzyl)-piperidin-4-yl]-(2-morpholin-4-yl-pyrimidin-5-yl)-amine,
[1-(2,6-diethoxy-4'-fluoro-biphenyl-4-ylmethyl)-piperidin-4-yl]-(2-morpholin-4-yl-pyrimidin-5-yl)-amine,
and pharmaceutically acceptable salts thereof.

Especially preferred are the following compounds of formula I of the present invention:
[1-(4-difluoromethoxy-3-ethoxy-benzyl)-piperidin-4-yl]-pyridin-3-yl-amine,
[1-(3,5-diisopropoxy-benzyl)-piperidin-4-yl]-pyridin-3-yl-amine,
[1-(4-chloro-3,5-diethoxy-benzyl)-piperidin-4-yl]-pyridin-3-yl-amine,
[1-(4-bromo-3,5-diethoxy-benzyl)-piperidin-4-yl]-pyridin-3-yl-amine,
[1-(3,5-diethoxy-4-pyrrol-1-yl-benzyl)-piperidin-4-yl]-pyridin-3-yl-amine,
N-{5-[1-(4-chloro-3,5-diethoxy-benzyl)-piperidin-4-ylamino]-pyridin-2-yl}-acetamide,
$N^5$-[1-(2,6-diethoxy-4'-fluoro-biphenyl-4-ylmethyl)-piperidin-4-yl]-3-methyl-pyridine-2,5-diamine,
[1-(3-isopropoxy-4-methoxy-benzyl)-piperidin-4-yl]-quinolin-3-yl-amine,
2,6-diethoxy-4-[4-(quinolin-3-ylamino)-piperidin-1-ylmethyl]-benzoic acid ethyl ester,
[1-(4-chloro-3,5-diethoxy-benzyl)-piperidin-4-yl]-quinolin-3-yl-amine,
[1-(4-chloro-3,5-diethoxy-benzyl)-piperidin-4-yl]-(2-methyl-pyridin-4-yl)-amine,
[1-(4-cyclopentyloxy-3-ethoxy-benzyl)-piperidin-4-yl]-quinolin-4-yl-amine,
[1-(4-difluoromethoxy-3-ethoxy-benzyl)-piperidin-4-yl]-quinolin-4-yl-amine,
[1-(4-benzyloxy-3-ethoxy-benzyl)-piperidin-4-yl]-(7-chloro-quinolin-4-yl)-amine,
[1-(3,5-diethoxy-4-fluoro-benzyl)-piperidin-4-yl]-pyrimidin-5-yl-amine,

[1-(4-chloro-3,5-diethoxy-benzyl)-piperidin-4-yl]-pyrimidin-5-yl-amine,
[1-(4-bromo-3,5-diethoxy-benzyl)-piperidin-4-yl]-pyrimidin-5-yl-amine,
[1-(3,5-diethoxy-4-pyrrol-1-yl-benzyl)-piperidin-4-yl]-pyrimidin-5-yl-amine,
[1-(4-chloro-3-ethoxy-benzyl)-piperidin-4-yl]-(2-phenyl-pyrimidin-5-yl)-amine,
[1-(4-allyloxy-3-ethoxy-benzyl)-piperidin-4-yl]-(2-phenyl-pyrimidin-5-yl)-amine,
[1-(4-difluoromethoxy-3-ethoxy-benzyl)-piperidin-4-yl]-(2-phenyl-pyrimidin-5-yl)-amine,
[1-(4-methoxy-3-propoxy-benzyl)-piperidin-4-yl]-(2-phenyl-pyrimidin-5-yl)-amine,
[1-(3-isopropoxy-4-methoxy-benzyl)-piperidin-4-yl]-(2-phenyl-pyrimidin-5-yl)-amine,
[1-(3-isobutoxy-4-methoxy-benzyl)-piperidin-4-yl]-(2-phenyl-pyrimidin-5-yl)-amine,
[1-(3-cyclopentyloxy-4-methoxy-benzyl)-piperidin-4-yl]-(2-phenyl-pyrimidin-5-yl)-amine,
[1-(3,5-diethoxy-benzyl)-piperidin-4-yl]-(2-phenyl-pyrimidin-5-yl)-amine,
2,6-diethoxy-4-[4-(2-phenyl-pyrimidin-5-ylamino)-piperidin-1-ylmethyl]-benzoic acid ethyl ester,
[1-(3,5-diethoxy-4-fluoro-benzyl)-piperidin-4-yl]-(2-phenyl-pyrimidin-5-yl)-amine,
[1-(4-chloro-3,5-diethoxy-benzyl)-piperidin-4-yl]-(2-phenyl-pyrimidin-5-yl)-amine,
[1-(4-bromo-3,5-diethoxy-benzyl)-piperidin-4-yl]-(2-phenyl-pyrimidin-5-yl)-amine,
[1-(3,5-diethoxy-4-pyrrol-1-yl-benzyl)-piperidin-4-yl]-(2-phenyl-pyrimidin-5-yl)-amine,
[1-(2,6-diethoxy-4'-fluoro-biphenyl-4-ylmethyl)-piperidin-4-yl]-(2-phenyl-pyrimidin-5-yl)-amine,
and pharmaceutically acceptable salts thereof.

Furthermore, the pharmaceutically acceptable salts of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises
a) reacting a compound of the general formula

G-X    II wherein G is as defined herein before and X is a leaving group, with a compound of the formula

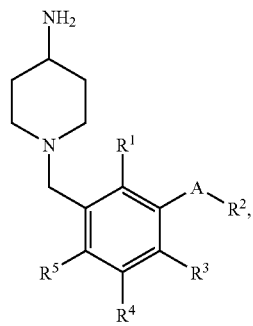

III wherein A and $R^1$ to $R^5$ are as defined herein before,
to obtain a compound of the formula

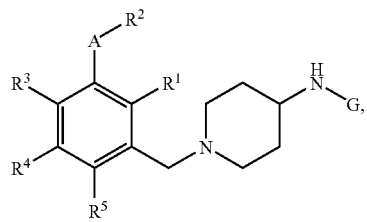

I and, if desired, converting the compound of formula I into a pharmaceutically acceptable salt; or, alternatively, b) reacting a compound of the general formula

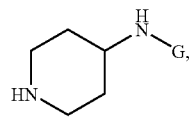

IV wherein G is as defined herein before,
with an aldehyde of the formula

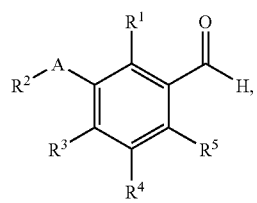

V wherein A and $R^1$ to $R^5$ are as defined herein before,
by employing a reducing agent to obtain a compound of the formula

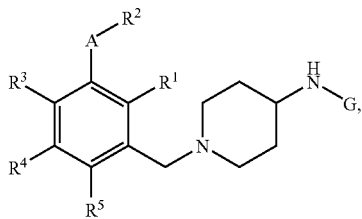

and, if desired, converting the compound of formula I into a pharmaceutically acceptable salt; or, alternatively, c) alkylating a compound of the general formula

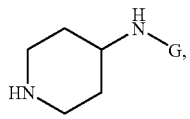

wherein G is as defined herein before, with a compound of the formula

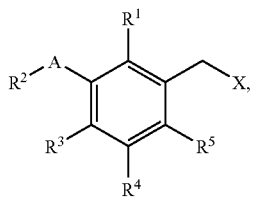

wherein A and $R^1$ to $R^5$ are as defined herein before and X is a leaving group,
under basic conditions to obtain a compound or formula

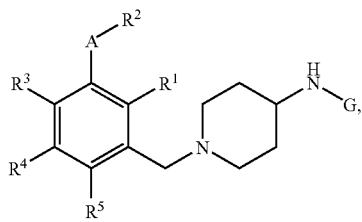

and, if desired, converting the compound of formula I into a pharmaceutically acceptable salt; or, alternatively, d) reacting a compound of the general formula

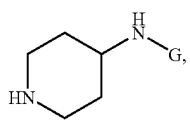

wherein G is as defined herein before, with a compound of the formula

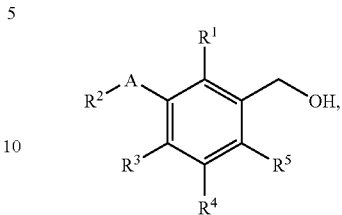

wherein A and $R^1$ to $R^5$ are as defined herein, in the presence of a trialkylphosphine and a diazo-compound to obtain a compound or formula

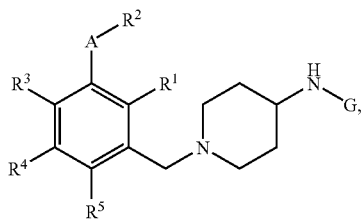

and if desired, converting the compound of formula I into a pharmaceutically acceptable salt.

The invention further relates to compounds of formula I as defined above, when manufactured according to a process as defined above.

Suitable reducing agents are preferably selected from the group consisting of pyridine-$BH_3$ complex, $NaBH(OAc)_3$ and $NaCNBH_3$. The reaction can be carried out under acidic conditions by using an acid such as acetic acid or formic acid or an Lewis acid (e.g., $Ti(iPrO)_4$, $ZnCl_2$) or under basic conditions (no additive) in a suitable solvent such as dichloromethane, dichloroethane or ethanol (or mixtures thereof) at ambient or elevated temperatures using conventional heating or heating by microwave irradiation.

Suitable leaving groups X are halides, mesylates or tosylates or alcohols containing another leaving group. Preferred leaving groups are selected from the group consisting of iodide, bromide, methanesulfonate and chloride.

As described above, the compounds of formula I of the present invention can be used as medicaments for the treatment and/or prevention of diseases which are associated with the modulation of SST receptors subtype 5.

"Diseases which are associated with the modulation of SST receptors subtype 5" are such diseases as diabetes mellitus, particularly type II diabetes mellitus, impaired fasting glucose, impaired glucose tolerance, micro- and macrovascular diabetic complications, posttransplantation diabetes mellitus in patients having type I diabetes mellitus, gestational diabetes, obesity, inflammatory bowel diseases such as Crohn's disease or ulcerative colitis, malabsorption, autoimmune diseases such as rheumatoid arthritis, osteoarthritis, psoriasis and other skin disorder, and immunodeficiencies. Microvascular diabetic complications include diabetic nephropathy and diabetic retinopathy, whereas macrovascular diabetes-associated complications lead to an increased risk for myocardial infarction, stroke and limb amputations.

The use as medicament for the treatment and/or prevention of diabetes mellitus, particularly type II diabetes mellitus, impaired fasting glucose or impaired glucose tolerance is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of SST receptors subtype 5.

In another embodiment, the invention relates to a method for the treatment and/or prevention of diseases which are which are associated with the modulation of SST receptors subtype 5, which method comprises administering a compound of formula I to a human or animal. The method for the treatment and/or prevention of diabetes mellitus, particularly type II diabetes mellitus, impaired fasting glucose or impaired glucose tolerance, is most preferred.

The invention further relates to the use of compounds as defined above for the treatment and/or prevention of diseases which are associated with the modulation of SST receptors subtype 5.

In addition, the invention relates to the use of compounds as defined above for the preparation of medicaments for the treatment and/or prevention of diseases which are associated with the modulation of SST receptors subtype 5. Preferred examples of such diseases are diabetes mellitus, particularly type II diabetes mellitus, impaired fasting glucose or impaired glucose tolerance.

The compounds of formula I can be manufactured by the methods given below, by the methods given in the examples or by analogous methods. Appropriate reaction conditions for the individual reaction steps are standard reactions and are known to a person skilled in the art.

Starting materials are either commercially available or can be prepared by methods analogous to the methods given below, by methods described in references cited in the text or in the examples, or by methods known in the art.

The synthesis of compounds with the general structure I are described in Schemes 1 to 6.

The synthesis of compounds of the general formula I can be accomplished according to Scheme 1.

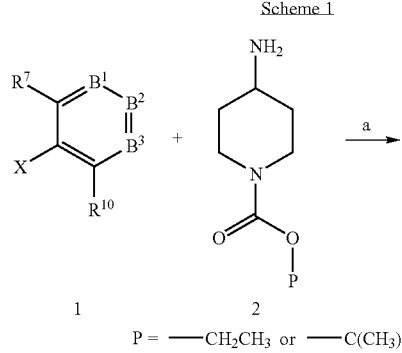

Scheme 1

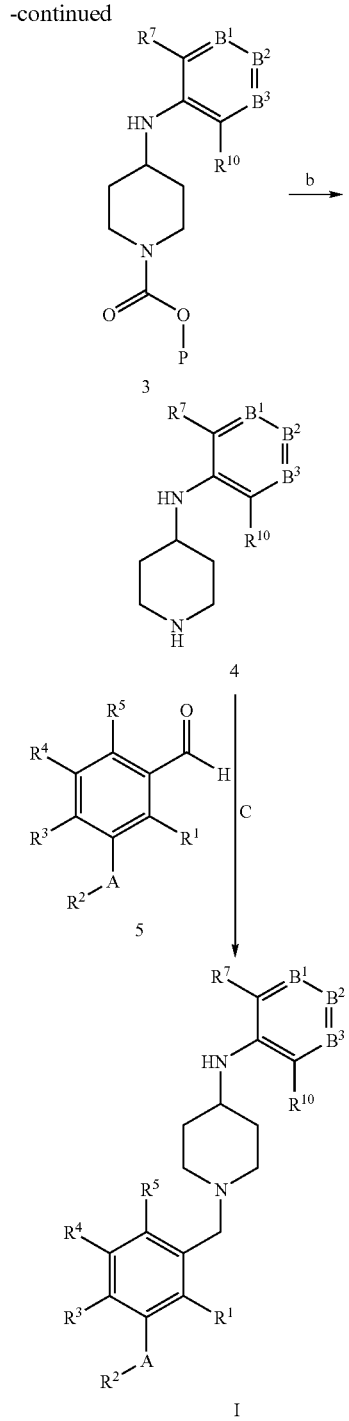

a $B^1 = N, B^2 = CR^9$ or $CR^{11}, B^3 = CR^8$ or N
b $B^1 = CR^{13}, B^2 = N, B^3 = CR^{14}, R^7 = R^{12}$ and $R^{10} = R^{15}$ Target structures I can be synthesized using Pd(0)-catalyzed amination reactions of 3-halo pyridines, 3-halo-quinolines or 5-halo-pyrimidines of general formula 1a or 4-halo-pyridines of general formula 1b with 4-amino-piperidines 2 (e.g., Buchwald-Hartwig coupling; see (a) J. P. Wolfe, S. Wagaw and S. L. Buchwald *J. Am. Chem. Soc.* 1996, 118, 7215-7216; (b) J. P. Wolfe and S. L. Buchwald *Tetrahedron Lett.* 1997, 38, 6359-6362; (c) J. P. Wolfe, S. Wagaw, J.-F. Marcoux and S. L. Buchwald *Acc. Chem. Res.* 1998, 31, 805-818; (d) B. H. Yang and S. L. Buchwald *J. Organomet.*

Chem. 1999, 576, 125-146; (e) J. F. Hartwig *Angew. Chem. Int. Ed.* 1998, 37, 2046-2067). Thereby halo-substituted heterocycles 1 are reacted with primary amines 2 under an inert atmosphere such as argon or nitrogen in the presence of a palladium catalyst such as tris(di-benzylideneacetone) dipalladium(0) ($Pd_2(dba)_3$) or palladium(II) acetate (Pd $(COOCH_3)_2$), a phosphine ligand like triphenylphosphine, rac-2,2'-bis(diphenyl-phosphino)-1,1'-binaphthalene (rac-BINAP), dicyclohexyl-(2',4',6'-triisopropyl-biphenyl-2-yl)-phosphane (X-Phos) or (R)-(−)-1-[(S)-2-(dicyclohexylphosphino)-ferrocenyl]ethyldi-tert-butylphosphine (Josiphos; see Q. Shen, S. Shekhar, J. P. Stambuli and J. F. Hartwig *Angew. Chem. Int. Ed.* 2005, 44, 1371-1375) and a base such as $Cs_2CO_3$ or KOtert-Bu in a solvent like toluene, ethanol or water or mixtures thereof, whereby X is a suitable leaving group such as chlorine, bromine, iodine, mesylate (methanesulfonate) or triflate (trifluoro-methanesulfonate) (Scheme 1, step a). Said C—N formation reaction may be conducted at room temperature or elevated temperatures, whereby heating might be achieved conventionally or by microwave irradiation (see also Palladium(0) Complexes in Organic Chemistry, in *Organometallics in Synthesis* (Ed. M. Schlosser), Chapter 4, $2^{nd}$ Edition, 2002, John Wiley & Sons, Ltd, Chichester, UK). The alkyloxycarbonyl protecting group present in compounds 3 can be removed, using e.g., 48% aqueous hydrogen bromide or 37% aqueous hydrochloric acid as reagent preferably at elevated temperatures to remove an ethyl carbamate or using trifluoroacetic acid or hydrochloric acid in a solvent like dichloromethane, dioxane or THF preferable at room temperature to remove a tert-butyloxycarbonyl (BOC)-protective group (see *Protective Groups in Organic Synthesis*, T. W. Greene and P. G. M. Wuts, $3^{rd}$ Edition, 1999, Wiley-Interscience), yielding 4-amino piperidines of formula 4 (Scheme 1, step b). Reductive N-alkylation of piperidines 4 with aldehydes 5 in the presence of a reducing agent such as pyridine-$BH_3$ complex, $NaBH(OAc)_3$ or $NaCNBH_3$ under acidic conditions (e.g., acetic acid, formic acid), by using a Lewis acid (e.g., $Ti(iPrO)_4$, $ZnCl_2$) or under buffered conditions, e.g., in the presence of acetic acid and a tertiary amine like N-ethyl-diisopropylamine or triethylamine, in a suitable solvent such as dichloromethane (DCM), dichloroethane, ethanol or isopropanol (or mixtures thereof) at ambient or elevated temperatures using conventional heating or heating by microwave irradiation provides target structures I (Scheme 1, step c). In the coupling step piperidines of formula 4 may thereby be used either as a salt, e.g., hydrochloride or hydrobromide salt, or as the corresponding free amine.

Scheme 2

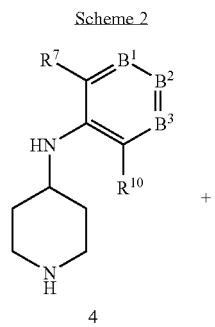

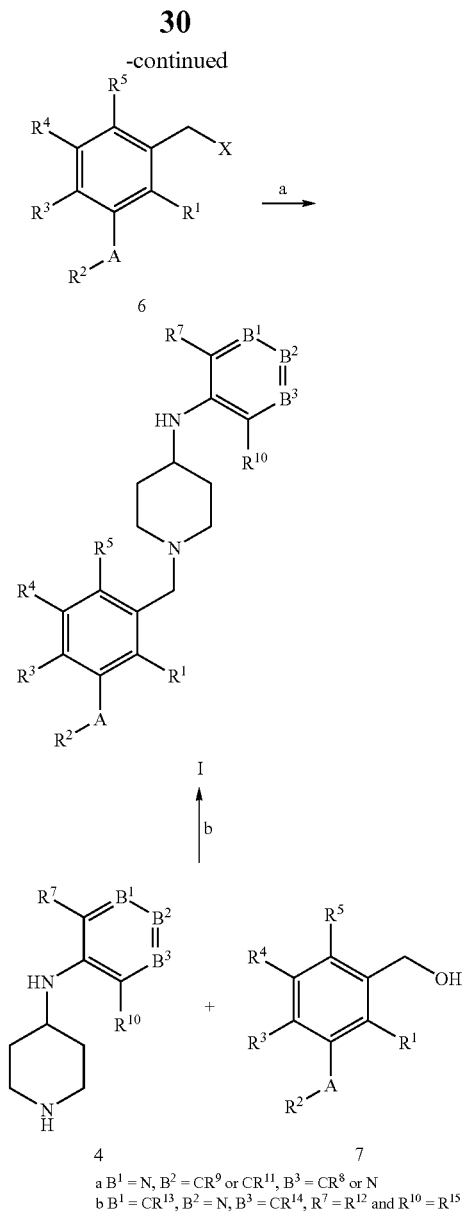

a $B^1 = N, B^2 = CR^9$ or $CR^{11}, B^3 = CR^8$ or N
b $B^1 = CR^{13}, B^2 = N, B^3 = CR^{14}, R^7 = R^{12}$ and $R^{10} = R^{15}$ Target compounds of formula I might also be manufactured by direct alkylation of piperidines 4 with suitable halides, mesylates, tosylates or alcohols containing any other suitable leaving group of general structure 6 in a solvent such as N,N-dimethylformamide, dichloromethane, dichloroethane or acetone at ambient or elevated temperatures using conventional heating or heating by microwave irradiation with the addition of a suitable tertiary amine base (e.g., triethylamine, N-ethyl diisopropylamine) or an inorganic base (e.g., $Cs_2CO_3$, $K_2CO_3$; Scheme 2, step a) or by analogous alkylation reactions. Alternatively target structures of formula I might be accessible by Mitsunobu reaction (D. L. Hughes, The Mitsunobu Reaction, in *Organic Reactions*, Volume 42, 1992, John Wiley & Sons, New York; pp. 335-656) applying alcohols 7 activated by a mixture of a phosphine like a trialkylphosphine such as tributylphosphine ($(n-Bu)_3P$), triphenylphosphine ($Ph_3P$) and the like and a diazo-compound like diethyl-azodicarboxylate (DEAD), diisopropyl-azodicarboxylate (DIAD) or di-tert-butyl-azodicarboxylate and the like in a solvent commonly used for such transformations like tetrahydrofurane (THF), toluene, dichloromethane and the like (Scheme 2, step b). There is no particular restriction on the nature of the solvent to be employed, provided that it has no adverse effect on the reaction or the reagents involved and that it can dissolve the reagents, at least to some extent. The reaction can take place over a wide range of temperatures ranging from ambient temperatures to the reflux temperature of the solvent employed.

Target structures of general formula I can also be synthesized by reductive N-alkylation of anilines 8 with suitably protected piperidinones of formula 9 (for protecting groups see *Protective Groups in Organic Synthesis*, T. W. Greene and P. G. M. Wuts, 3$^{rd}$ Edition, 1999, Wiley-Interscience) in the presence of a reducing agent such as pyridine-BH$_3$ complex, NaBH(OAc)$_3$ or NaCNBH$_3$ under acidic conditions (e.g., acetic acid, formic acid), by using a Lewis acid (e.g., Ti(iPrO)$_4$, ZnCl$_2$) or under buffered conditions, e.g., in the presence of acetic acid and a tertiary amine like N-ethyl diisopropylamine or triethylamine in a suitable solvent such as dichloromethane, dichloroethane, ethanol or isopropanol (or mixtures thereof) at ambient or elevated temperatures using conventional heating or heating by microwave irradiation providing piperidines of general formula 3 (Scheme 3, step a). The alkyloxycarbonyl protecting group present in compounds 3 can be removed, using e.g., 48% aqueous hydrogen bromide or 37% aqueous hydrochloric acid as reagent preferably at elevated temperatures to remove an ethyl carbamate or using trifluoroacetic acid or hydrochloric acid in a solvent like dichloromethane, dioxane or THF preferable at room temperature to remove a tert-butyloxycarbonyl (BOC)-protective group (see *Protective Groups in Organic Synthesis*, T. W. Greene and P. G. M. Wuts, 3$^{rd}$ Edition, 1999, Wiley-Interscience), yielding phenyl-piperidin-4-yl-amines of formula 4 (Scheme 3, step b). Reductive N-alkylation of piperidines 4 with aldehydes 5 provides then access to target structures I (Scheme 3, step c).

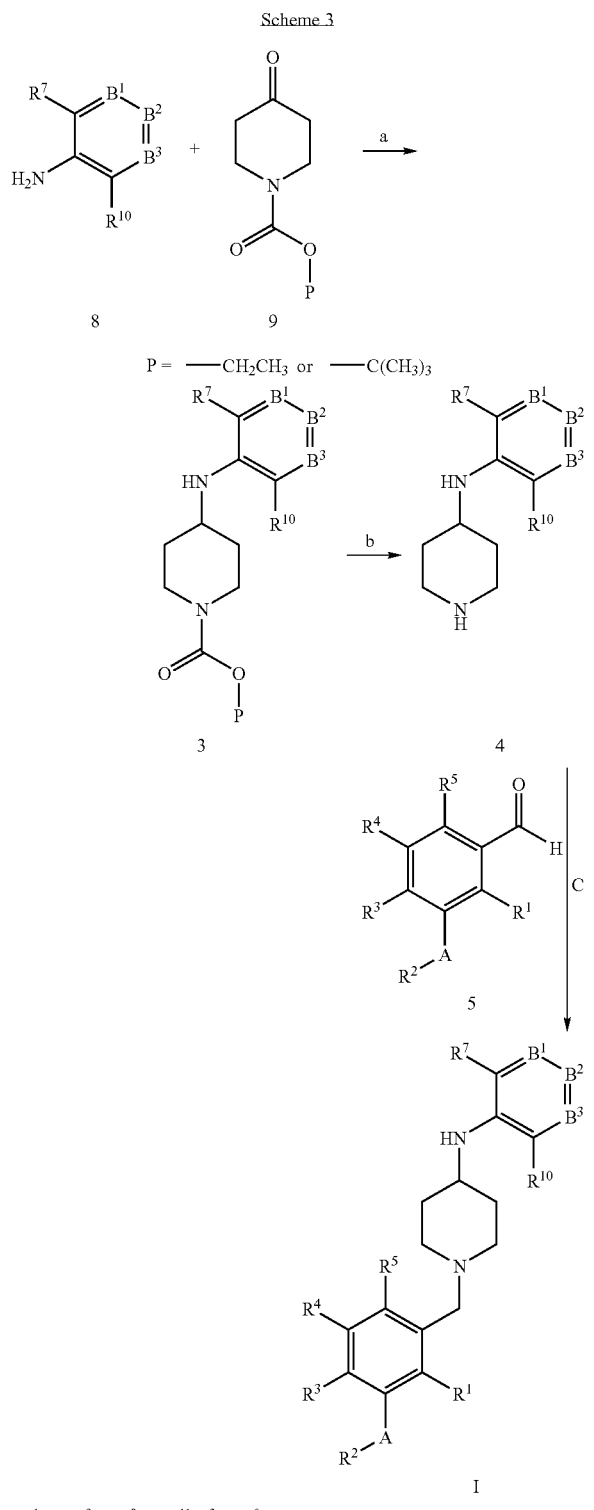

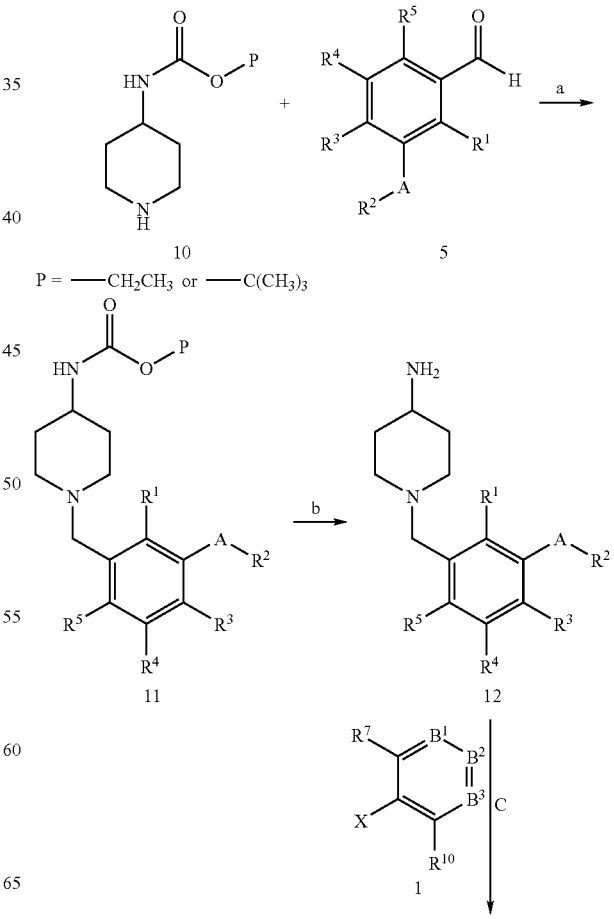

a B$^1$ = N, B$^2$ = CR$^9$ or CR$^{11}$, B$^3$ = CR$^8$ or N
b B$^1$ = CR$^{13}$, B$^2$ = N, B$^3$ = CR$^{14}$, R$^7$ = R$^{12}$ and R$^{10}$ = R$^{15}$ -continued

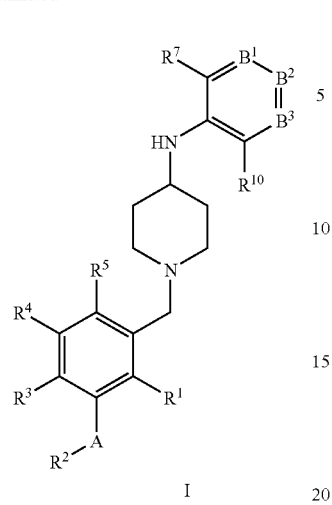

I a B¹ = N, B² = CR⁹ or CR¹¹, B³ = CR⁸ or N
b B¹ = CR¹³, B² = N, B³ = CR¹⁴, R⁷ = R¹² and R¹⁰ = R¹⁵

Target structures of formula I can also be accomplished employing an inverted reaction sequence, namely by first reductively coupling suitably protected piperidines (for protecting groups see *Protective Groups in Organic Synthesis*, T. W. Greene and P. G. M. Wuts, 3$^{rd}$ Edition, 1999, Wiley-Interscience) of formula 10 with aldehydes 5 in the presence of a reducing agent such as pyridine-BH₃ complex, NaBH(OAc)₃ or NaCNBH₃ under acidic conditions (e.g., acetic acid, formic acid), by using a Lewis acid (e.g., Ti(iPrO)₄, ZnCl₂) or under buffered conditions, e.g., in the presence of acetic acid and a tertiary amine like N-ethyl-diisopropylamine or triethylamine, in a suitable solvent such as dichloromethane (DCM), dichloroethane, ethanol or isopropanol (or mixtures thereof) at ambient or elevated temperatures using conventional heating or heating by microwave irradiation provide piperidines of general formula 11 (Scheme 4, step a). The protection group of piperidines 11 are then removed yielding the secondary amines 12 (Scheme 4, step b), which undergo Pd(0)-catalyzed amination reactions with heteroaryls 1 yielding target structures I (Scheme 4, step c). In contrast to the strategy outlined in Scheme 1 where the point of diversification is the benzyl moiety this synthetic route is of particular interest for the rapid and parallel variation of the heteroaryl moiety. The 4-amino-piperidines of formula 12 may thereby used either as a salt, e.g., hydrochloride or hydrobromide salt, or as the corresponding free amine.

Scheme 5

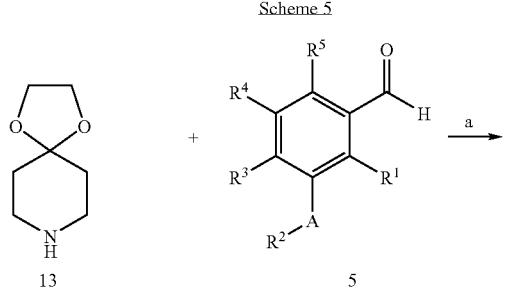

-continued

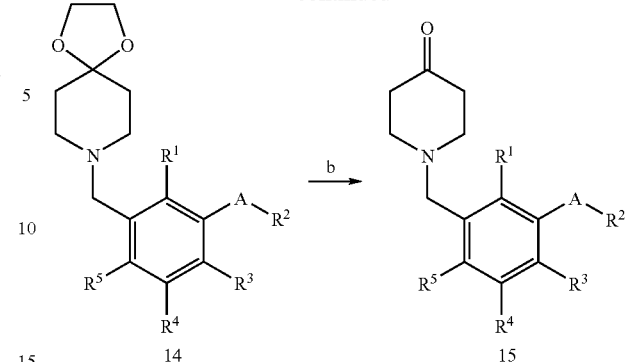

I a B¹ = N, B² = CR⁹ or CR¹¹, B³ = CR⁸ or N
b B¹ = CR¹³, B² = N, B³ = CR¹⁴, R⁷ = R¹² and R¹⁰ = R¹⁵

Alternatively, target structures of formula I can be accomplished employing the reaction sequence outlined in Scheme 5. Reductive coupling of suitably ketone protected piperidines (for protecting groups see *Protective Groups in Organic Synthesis*, T. W. Greene and P. G. M. Wuts, 3$^{rd}$ Edition, 1999, Wiley-Interscience) such as 1,4-dioxa-8-azaspiro[4.5]decane (13) with aldehydes 5 provides piperidines 14 (Scheme 5, step a), which are subsequently deprotected to ketones 15 (Scheme 5, step b). In the case of an acetal this deprotection step is preferentially conducted under acid catalysis (e.g., hydrochloric acid) in a solvent such as water under elevated temperatures. Finally, N-alkylation of benzyl-piperidinones 15 with anilines 8 under reductive reaction conditions affords target structures I (Scheme 5, step c). In contrast to the strategy outlined in Scheme 3, where the point of diversification is the benzyl moiety, and similarly to Scheme 4 this synthetic route is of particular interest if the variation of the heteroaryl group is aimed for in a rapid and parallel fashion.

The starting heteroaryl compounds 1 (e.g., 4-(5-bromo-pyridin-2-yl)-morpholine, 4-bromo-quinoline or 5-bromo-pyrimidine) and anilines 8 (e.g., 3-amino-pyridine, N-(5-amino-pyridin-2-yl)-acetamide or quinolin-3-ylamine) are known compounds and are commercially available or can be prepared by numerous methods using conventional reaction procedures generally known in the art. There is a plethora of references known in the art teaching methods useful for the preparation of aforementioned heterocyclic ring systems. The reader is referred to (a) A. R. Katritzky, *Handbook of Heterocyclic Chemistry*, 1985, Pergamon Press Ltd, Oxford, United Kingdom and references cited therein, (b) T. Eicher and S. Hauptmann (translated by H. Suschitzky and J. Suschitzky), *The Chemistry of Heterocycles*, 1995, Georg Thieme Verlag, Stuttgart, Deutschland and references cited therein and (c) H. Krauch and W. Kunz, *Reaktionen der organischen Chemie*, 6., neubearbeitete Auflage, 1997, Hüthig GmbH, Heidelberg, Deutschland and references cited therein.

Synthesis of Aldehyde Intermediates

The requisite aldehyde partners are either commercially available or can be derived by alkylation with alkyl halides, alkyl mesylates, alkyl tosylates or alcohols containing any other suitable leaving group in a polar solvent such as DMF (N,N-dimethylformamide) or acetone and a suitable base (e.g., $Cs_2CO_3$, $K_2CO_3$) at room temperature or elevated temperatures, by Mitsunobu reaction with alcohols activated by a mixture of triphenylphosphine and diethylazadicarboxylate, or by analogous alkylation of the phenolic carboxylic esters or acids of formula 16 (Scheme 6, step a). Reduction of the esters of formula 17 by a suitable reducing agent (e.g., diisobutylaluminium hydride at low temperature, with $LiAlH_4$ at elevated or ambient temperature) in a solvent such as THF (tetrahydrofurane) provides the corresponding benzylalcohols of formula 18 (Scheme 6, step b). These can then be oxidized to the aldehydes of formula 19, preferably with activated $MnO_2$ as oxidant in dichloromethane (Scheme 6, step c).

Alternatively the introduction of the side-chain can be accomplished by direct alkylation (sequential for unsymmetrical compounds) of the phenolic benzaldehydes of formula 20 providing the desired compounds of formula 19 directly (Scheme 6, step d).

A further well-established route towards the synthesis of benzylaldehydes of formula 22 consists in the reduction of the corresponding benzonitriles of formula 21 by a suitable reducing agent such as diisobutylaluminium hydride at low temperature in a non-protic polar solvent (e.g., THF; Scheme 6, step e).

Additional syntheses of aldehydes of formula II are described in the examples.

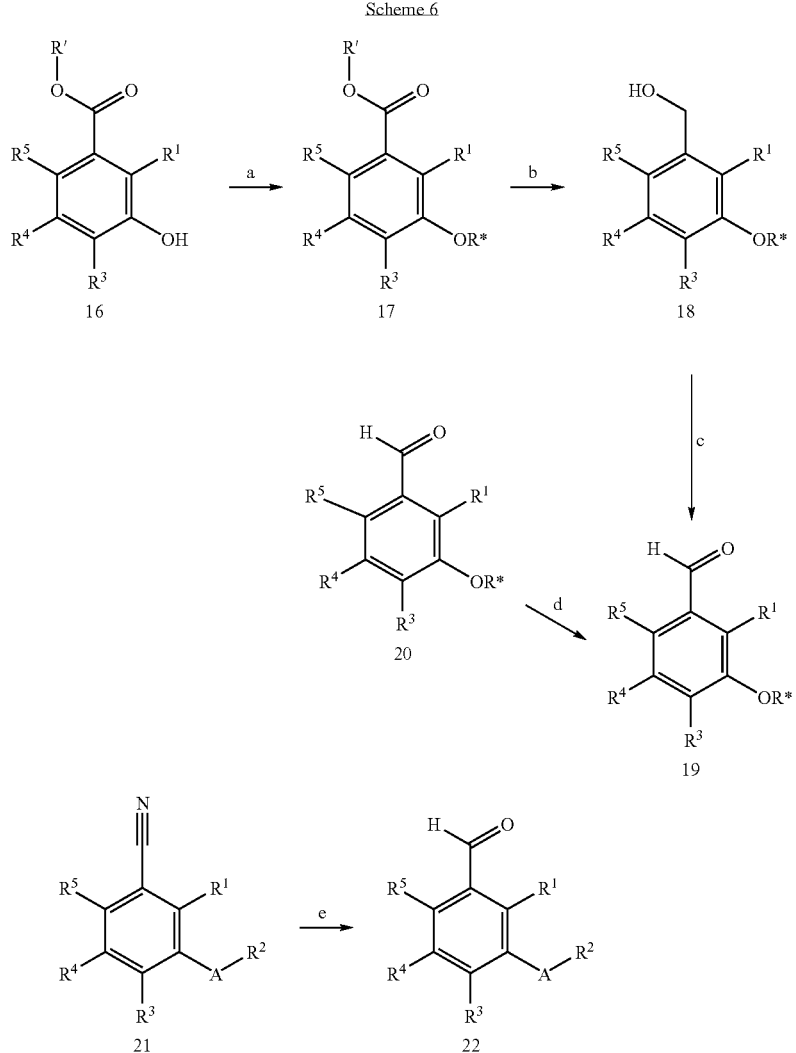

Scheme 6

As described hereinbefore, it has been found that the compounds of formula I possess pharmaceutical activity, in particular they are modulators of somatostatin receptor activity. More particularly, the compounds of the present invention have been found to be antagonists of the somatostatin receptor subtype 5 (SSTR5).

The following tests were carried out in order to determine the activity of the compounds of formula I.

A CHO cell line stably transfected with a plasmid encoding the human subtype 5 somatostatin receptor (GenBank accession number D16827) was obtained from Euroscreen. Cells were cultured and used for binding and functional assays.

Membranes of these cells were prepared by sonication in the presence of protease inhibitors and subsequent fractionating centrifugation. The protein concentration in the membrane preparation was determined using a commercial kit (BCA kit, Pierce, USA). Membranes were stored at −80° C. until use. After thawing membranes were diluted in assay buffer (50 mM Tris-HCl at pH 7.4, 5 mM $MgCl_2$ and 0.20% BSA) and subjected to Dounce homogenization.

For binding studies, 0.1 mL membrane suspension, corresponding to approximately $6 \times 10^{-15}$ mol receptor, was incubated for 1 h at rt with 0.05 nM $^{125}$I-labeled tracer (11-Tyr somatostatin-14, Perkin-Elmer) and either test compounds in varying concentrations or, for the determination of non-specific binding, 0.001 mM non-labeled somatostatin-14. The incubation was stopped by filtration through GF/B glassfiber filters and washing with ice-cold wash buffer (50 mM Tris-HCl at pH 7.4). The bound radioactivity was measured after application of a scintillation cocktail (Microscint 40) and expressed as disintegrations per minute (dpm).

The receptor concentration was determined in a prior saturation experiment where a fixed, arbitrary amount of membranes was incubated with a concentration range of radio-labeled tracer. This allows estimating the total number of specific binding sites per amount of protein (i.e., $B_{max}$), typically between 1 and 5 pmol/mg.

The concentration of the test compound required to result in half maximal inhibition of binding of the radio-labeled tracer ($IC_{50}$) was estimated from a concentration-versus-dpm graph. The binding affinity ($K_i$) was calculated from the $IC_{50}$ by applying the Cheng-Prussoff equation for single binding sites.

For functional experiments, 50,000 cells were incubated in Krebs Ringer HEPES buffer (115 mM NaCl, 4.7 mM KCl, 2.56 mM $CaCl_2$, 1.2 mM $KH_2PO_4$, 1.2 mM $MgSO_4$, 20 mM $NaHCO_3$ and 16 mM HEPES, adjusted to pH 7.4) supplemented with 1 mM IBMX and 0.1% BSA, then stimulated with 0.004 mM forskolin. Simultaneously with forskolin, test compounds in varying concentrations were applied. Cells were then incubated for 20 minutes at 37° C. and 5% $CO_2$. Subsequently, cells were lysed and cAMP concentration measured using a fluorescence-based commercial kit according to the manufacturer (HitHunter cAMP, DiscoverX).

The concentration of the test compound to induce a half maximal effect (i.e., $EC_{50}$) as well as the efficacy as compared to 0.15 nM somatostatin-14 were determined from concentration-versus-fluorescence (arbitrary units) graphs. For the determination of potential antagonism, 0.15 nM somatostatin-14 was applied together with the test compounds and the concentration of the test compounds to half maximally reverse the effect of somatostatin-14 (i.e., $IC_{50}$) were deduced from concentration-versus-fluorescence graphs.

The compounds of the present invention exhibit in a radioligand replacement assay $K_i$ values of 0.1 nM to 10 μM, preferably $K_i$ values of 0.1 nM to 500 nM and more preferably 0.1 nM to 100 nM for the human subtype 5 somatostatin receptor. The following table shows measured values for selected compounds of the present invention.

| | SSTR5 $K_i$ (nmol/l) |
|---|---|
| Example 79 | 25 |
| Example 99 | 62 |
| Example 122 | 492 |

The compounds of formula I and their pharmaceutically acceptable salts and esters can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or infusion solutions, or topically, e.g., in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The present invention will be further explained by reference to the following illustrative examples. They are, however, not intended to limit its scope in any manner.

EXAMPLES

Abbreviations

Ar=argon, DMF=N,N-dimethylformamide, DMSO=dimethyl sulfoxide, EI=electron impact (ionization), ESI=electron spray ionisation, HPLC=high performance liquid chromatography, Hyflo Super Cel®=filtration aid (Fluka), ISN=ion spray negative (mode), ISP=ion spray positive (mode), NMR=nuclear magnetic resonance, MPLC=medium pressure liquid chromatography, MS=mass spectrum, P=protecting group, R=any group, rt=room temperature, THF=tetrahydrofuran, X=halogen, X-Phos ligand=dicyclohexyl-(2',4',6'-triisopropyl-biphenyl-2-yl)-phosphane; Y=any group including heteroatoms and halides.

Example 1

[1-(3-Ethoxy-4-methyl-benzyl)-piperidin-4-yl]-pyridin-3-yl-amine

Step 1:
4-(Pyridin-3-ylamino)-piperidine-1-carboxylic acid tert-butyl ester

A mixture of 3-aminopyridine (2.60 g, 27.60 mmol, 1.0 equiv; commercially available) and 4-oxo-piperidine-1-carboxylic acid tert-butyl ester (5.50 g, 27.60 mmol, 1.0 equiv; commercially available) in conc. acetic acid (1.57 mL, 1.66 g, 27.60 mmol, 1.0 equiv) and dichloroethane (50 mL) was stirred at rt for 4 h. Sodium triacetoxyborohydride (7.02 g, 33.12 mmol, 1.2 equiv) was added in one portion and the reaction mixture stirred for an additional time period of 16 h. To the reaction mixture was added a sat. solution of NaCl (2×50 mL) and the crude extracted with ethyl acetate (3×100 mL). The combined organic phases were washed over a sat. solution of $Na_2CO_3$ (50 mL), dried over $MgSO_4$, concentrated by evaporation under reduced pressure and the crude material purified with silica column chromatography eluting with a gradient of dichloromethane/methanol (10:0→4:1) to yield 3.60 g (47%) of the title compound in 90% purity according to $^1$H NMR. $^1$H NMR (360 MHz, $CDCl_3$): δ 1.28-1.41 (m, 2H), 1.47 (s, 9H), 2.04 (dd, J=12.8 Hz, J=2.6 Hz, 2H), 2.93 (t, J=12.3 Hz, 2H), 3.44 (br s, 1H), 3.58 (br s, 1H), 4.07 (d, J=10.7 Hz, 2H), 6.83-6.91 (m, 1H), 7.08 (dd, J=8.2 Hz, J=4.5 Hz, 1H), 7.96 (d, J=3.6 Hz, 1H), 8.02 (d, J=2.5 Hz, 1H). MS (ESI): 278.5 [M+H]$^+$.

Step 2: Piperidin-4-yl-pyridin-3-yl-amine dihydrochloride (Intermediate A1)

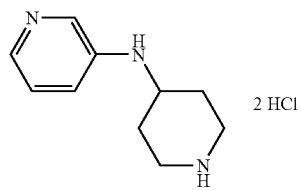

A solution of 4-(pyridin-3-ylamino)-piperidine-1-carboxylic acid tert-butyl ester (1.37 g, 5.00 mmol) in dioxane (20 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 178.3 [M+H]$^+$.

Step 3: [1-(3-Ethoxy-4-methyl-benzyl)-piperidin-4-yl]-pyridin-3-yl-amine

To a solution of piperidin-4-yl-pyridin-3-yl-amine dihydrochloride (37.5 mg, 0.15 mmol, 1.0 equiv; intermediate A1) in ethanol (1 mL), acetic acid (72.1 mg, 1.2 mmol, 8.0 equiv) and N-ethyl diisopropylamine (77.6 mg, 0.6 mmol, 4.0 equiv) was added 3-ethoxy-4-methyl-benzaldehyde (29.6 mg, 0.18 mmol, 1.2 equiv; intermediate B21, vide infra) and the mixture stirred at 55° C. After 1 h, sodium cyanoborohydride (47.1 mg, 0.75 mmol, 5.0 equiv), dissolved in ethanol (0.5 mL), was added and the mixture stirred at 55° C. over night. Removal of the solvent under reduced pressure and purification by preparative HPLC on reversed phase eluting with a gradient of acetonitrile/water provided 11.3 mg (23%) of the title compound. MS (ISP): 326.3 [M+H]$^+$.

The pyridine, quinoline and pyrimidine intermediates A2 to A13 were prepared as described below.
Synthesis of Pyridine, Quinoline and Pyrimidine Intermediates A2 and A13 to be used in Table I Intermediate A2

(6-Morpholin-4-yl-pyridin-3-yl)-piperidin-4-yl-amine dihydrochloride

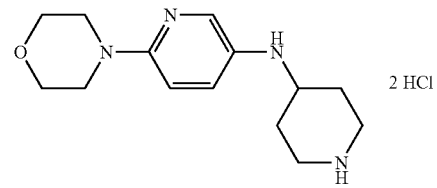

Step 1: 4-(6-Morpholin-4-yl-pyridin-3-ylamino)-piperidine-1-carboxylic acid tert-butyl ester To a degassed solution of 4-(5-bromo-pyridin-2-yl)-morpholine (4.47 g, 18.39 mmol, 1.0 equiv; commercially available) and 4-amino-piperidine-1-carboxylic acid tert-butyl ester (4.42 g, 22.07 mmol, 1.2 equiv; commercially available) in toluene (40 mL) was added KOtert-Bu (5.16 g, 46.00 mmol, 2.5 equiv), dicyclohexyl-(2',4',6'-triisopropyl-biphenyl-2-yl)-phosphane (0.18 g, 0.37 mmol, 0.02 equiv; X-Phos ligand [CAS RN 564483-18-7]; commercially available from Strem Chemicals, USA) and tris(dibenzylideneacetone)dipalladium(0) (1.52 g, 1.47 mmol, 0.08 equiv). The reaction mixture was stirred under nitrogen at 100° C. for 16 h, cooled to rt, filtered and the filtrate concentrated by evaporation under reduced pressure. The crude material was purified with silica column chromatography eluting with dichloromethane/methanol (20:1+0.5% triethylamine) to provide 1.60 g (24%) of the title compound in 90% purity according to $^1$H NMR. $^1$H NMR (400 MHz, $CH_3OD$): δ 1.20-1.37 (m, 2H), 1.46 (s, 9H), 1.95 (dd, J=13.0 Hz, J=2.7 Hz, 2H), 2.94 (br s, 2H), 3.21-3.28 (m, 4H), 3.32-3.41 (m, 1H), 3.73-3.84 (m, 4H), 4.01 (d, J=13.4 Hz, 2H), 6.74 (d, J=9.0 Hz, 1H), 7.12 (dd, J=9.0 Hz, J=2.9 Hz, 1H), 7.68 (d, J=2.7 Hz, 1H). MS (ISP): 363.3 [M+H]$^+$.

Step 2: (6-Morpholin-4-yl-pyridin-3-yl)-piperidin-4-yl-amine dihydrochloride

A solution of 4-(6-morpholin-4-yl-pyridin-3-ylamino)-piperidine-1-carboxylic acid tert-butyl ester (1.31 g, 3.61 mmol) in dioxane (20 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 263.4 [M+H]$^+$.

Intermediate A3

N-[5-(Piperidin-4-ylamino)-pyridin-2-yl]-acetamide dihydrochloride

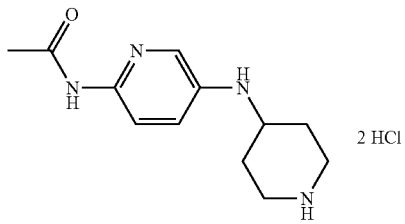

Step 1: 4-(6-Acetylamino-pyridin-3-ylamino)-piperidine-1-carboxylic acid tert-butyl ester A mixture of N-(5-amino-pyridin-2-yl)-acetamide (2.05 g, 13.55 mmol, 1.0 equiv; commercially available) and 4-oxo-piperidine-1-carboxylic acid tert-butyl ester (2.70 g, 13.55 mmol, 1.0 equiv; commercially available) in conc. acetic acid (0.78 mL, 0.81 g, 13.55 mmol, 1.0 equiv) and dichloroethane (50 mL) was stirred at rt for 4 h. Sodium triacetoxyborohydride (3.45 g, 16.26 mmol, 1.2 equiv) was added in one portion and the reaction mixture stirred for an additional time period of 16 h. To the reaction mixture was added a sat. solution of NaCl (2×50 mL) and the crude extracted with ethyl acetate (3×100 mL). The combined organic phases were washed over a sat. solution of Na$_2$CO$_3$ (50 mL), dried over MgSO$_4$, concentrated by evaporation under reduced pressure and the crude material purified with silica column chromatography eluting with a gradient of dichloromethane/methanol (50:1→12:1). Recrystallization from diethylether provided 0.91 g (20%) of the title compound in 90% purity according to $^1$H NMR. $^1$H NMR (400 MHz, DMSO): δ 1.12-1.28 (m, 2H), 1.40 (s, 9H), 1.86 (d, J=12.3 Hz, 2H), 2.00 (s, 3H), 2.90 (br s, 2H), 3.39 (d, J=9.1 Hz, 1H), 3.86 (d, J=12.8 Hz, 2H), 5.48 (d, J=8.4 Hz, 1H), 7.00 (d, J=8.9 Hz, 1H), 7.69 (d, J=2.7 Hz, 1H), 7.77 (d, J=8.9 Hz, 1H), 10.01 (s, 1H). MS (ESI): 335.3 [M+H]$^+$.

Step 2: N-[5-(Piperidin-4-ylamino)-pyridin-2-yl]-acetamide dihydrochloride

A solution of 4-(6-acetylamino-pyridin-3-ylamino)-piperidine-1-carboxylic acid tert-butyl ester (1.20 g, 3.59 mmol) in dioxane (20 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 235.3 [M+H]$^+$.

Intermediate A4

3-Methyl-N$^5$-piperidin-4-yl-pyridine-2,5-diamine dihydrochloride

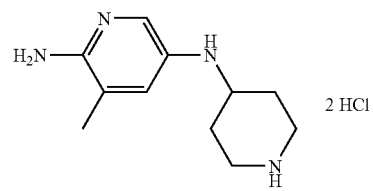

Step 1: 4-(6-Amino-5-methyl-pyridin-3-ylamino)-piperidine-1-carboxylic acid tert-butyl ester To a degassed solution of N-(5-bromo-3-methyl-pyridin-2-yl)-acetamide (4.92 g, 21.48 mmol, 1.0 equiv; commercially available) and 4-amino-piperidine-1-carboxylic acid tert-butyl ester (5.16 g, 25.77 mmol, 1.2 equiv; commercially available) in toluene (40 mL) was added KOtert-Bu (6.03 g, 53.69 mmol, 2.5 equiv), dicyclohexyl-(2',4',6'-triisopropyl-biphenyl-2-yl)-phosphane (0.21 g, 0.43 mmol, 0.02 equiv; X-Phos ligand [CAS RN 564483-18-7]; commercially available from Strem Chemicals, USA) and tris(dibenzylideneacetone)dipalladium(0) (1.78 g, 1.72 mmol, 0.08 equiv). The reaction mixture was stirred under nitrogen at 100° C. for 16 h, cooled to rt, filtered and the filtrate concentrated by evaporation under reduced pressure. The crude material was purified with silica column chromatography eluting with a gradient of ethyl acetate/triethylamine (10:0→4:1) and then recrystallized from ethyl acetate/heptane to provide 2.96 g (45%) of the title compound in 70% purity according to $^1$H NMR. $^1$H NMR (250 MHz, DMSO): δ 1.03-1.28 (m, 2H), 1.39 (s, 9H), 1.82 (dd, J=12.3 Hz, J=3.9 Hz, 2H), 1.98 (s, 3H), 2.72-2.98 (m, 2H), 3.11-3.29 (m, 1H), 3.84 (d, J=13.4 Hz, 2H), 4.52 (d, J=8.7 Hz, 1H), 5.60 (br s, 2H), 6.73 (d, J=2.3 Hz, 1H), 7.29 (d, J=2.7 Hz, 1H). MS (ESI): 307.2 [M+H]$^+$.

Step 2: 3-Methyl-N$^5$-piperidin-4-yl-pyridine-2,5-diamine dihydrochloride

A solution of 4-(6-amino-5-methyl-pyridin-3-ylamino)-piperidine-1-carboxylic acid tert-butyl ester (2.84 g, 9.27 mmol) in dioxane (30 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 207.1 [M+H]$^+$.

Intermediate A5

N-[6-Methyl-5-(piperidin-4-ylamino)-pyridin-2-yl]-acetamide dihydrochloride

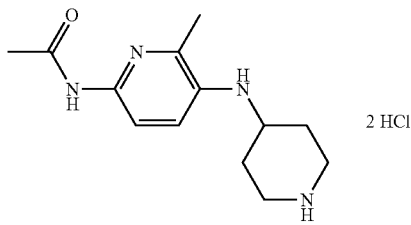

Step 1: 4-(6-Acetylamino-2-methyl-pyridin-3-ylamino)-piperidine-1-carboxylic acid tert-butyl ester To a degassed solution of N-(5-bromo-6-methyl-pyridin-2-yl)-acetamide (4.16 g, 18.18 mmol, 1.0 equiv; commercially available) and 4-amino-piperidine-1-carboxylic acid tert-butyl ester (4.37 g, 21.81 mmol, 1.2 equiv; commercially available) in toluene (40 mL) was added KOtert-Bu (5.10 g, 45.44 mmol, 2.5 equiv), dicyclohexyl-(2',4',6'-triisopropyl-biphenyl-2-yl)-phosphane (0.17 g, 0.36 mmol, 0.02 equiv; X-Phos ligand [CAS RN 564483-18-7]; commercially available from Strem Chemicals, USA) and tris(dibenzylideneacetone)dipalladium(0) (1.51 g, 1.45 mmol, 0.08 equiv). The reaction mixture was stirred under nitrogen at 100° C. for 16 h, cooled to rt, filtered and the filtrate concentrated by evaporation under reduced pressure. The crude material was purified with silica column chromatography eluting with a gradient of dichloromethane/methanol (10:0→9:1) and then recrystallized from diethylether to provide 0.38 g (6%) of the title compound in 90% purity according to $^1$H NMR. $^1$H NMR (250 MHz, DMSO): δ 1.31 (d, J=9.2 Hz, 2H), 1.40 (s, 9H), 1.86 (d, J=11.4 Hz, 2H), 1.99 (s, 3H), 2.24 (s, 3H), 2.86 (br s, 2H), 3.41 (br s, 1H), 3.92 (d, J=14.0 Hz, 2H), 4.51 (d, J=8.1 Hz, 1H), 7.00 (d, J=8.8 Hz, 1H), 7.69 (d, J=8.7 Hz, 1H), 9.98 (s, 1H). MS (ESI): 349.3 [M+H]$^+$.

Step 2: N-[6-Methyl-5-(piperidin-4-ylamino)-pyridin-2-yl]-acetamide dihydrochloride A solution of 4-(6-acetylamino-2-methyl-pyridin-3-ylamino)-piperidine-1-carboxylic acid tert-butyl ester (0.38 g, 1.09 mmol) in dioxane (10 mL) and 4 M HCl in dioxane (10 mL) was stirred at rt for 2 h. The solvent was removed under reduced pressure and the crude product used in the consecutive step without further purification assuming quantitative deprotection and formation of the dihydrochloride salt. MS (ISP): 249.3 [M+H]$^+$.

Intermediate A6

Piperidin-4-yl-quinolin-3-yl-amine dihydrochloride

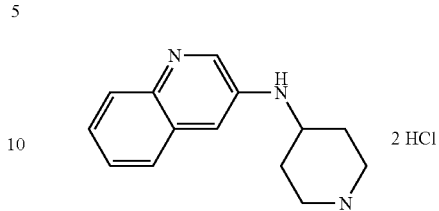

Step 1: 4-(Quinolin-3-ylamino)-piperidine-1-carboxylic acid tert-butyl ester A mixture of quinolin-3-ylamine (3.62 g, 25.09 mmol, 1.0 equiv, commercially available) and 4-oxo-piperidine-1-carboxylic acid tert-butyl ester (5.00 g, 25.09 mmol, 1.0 equiv; commercially available) in conc. acetic acid (1.44 mL, 1.51 g, 25.09 mmol, 1.0 equiv) and dichloroethane (50 mL) was stirred at rt for 4 h. Sodium triacetoxyborohydride (6.38 g, 30.11 mmol, 1.2 equiv) was added in one portion and the reaction mixture stirred for an additional time period of 16 h. To the reaction mixture was added a sat. solution of NaCl (2×50 mL) and the crude extracted with ethyl acetate (3×100 mL). The combined organic phases were washed over a sat. solution of Na$_2$CO$_3$ (50 mL), dried over MgSO$_4$, concentrated by evaporation under reduced pressure and the crude material purified with silica column chromatography eluting with a gradient of dichloromethane/methanol (10:1→9:1). Trituration from heptane/ethyl acetate provided 4.60 g (56%) of the title compound. $^1$H NMR (400 MHz, CDCl$_3$): δ 1.36-1.46 (m, 2H), 1.49 (s, 9H), 2.12 (d, J=10.5 Hz, 2H), 3.00 (t, J=11.9 Hz, 2H), 3.47-3.64 (m, 1H), 3.89 (d, J=7.7 Hz, 1H), 4.10 (br s, 2H), 7.03 (d, J=2.7 Hz, 1H), 7.37-7.47 (m, 2H), 7.59-7.64 (m, 1H), 7.89-7.98 (m, 1H), 8.42 (d, J=2.7 Hz, 1H).

Step 2: Piperidin-4-yl-quinolin-3-yl-amine dihydrochloride

A solution of 4-(quinolin-3-ylamino)-piperidine-1-carboxylic acid tert-butyl ester (1.77 g, 5.41 mmol) in dioxane (20 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 228.6 [M+H]$^+$.

Intermediate A7

(2-Methyl-pyridin-4-yl)-piperidin-4-yl-amine dihydrochloride

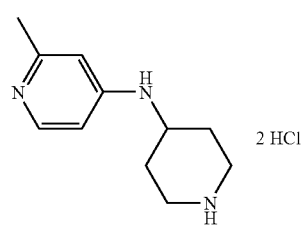

Step 1: 4-(2-Methyl-pyridin-4-ylamino)-piperidine-1-carboxylic acid tert-butyl ester To a degassed solution of 4-bromo-2-methyl-pyridine (1.99 g, 11.55 mmol, 1.0 equiv; commercially available) and 4-amino-piperidine-1-carboxylic acid tert-butyl ester (2.78 g, 13.86 mmol, 1.2 equiv; commercially available) in toluene (40 mL) was added KOtert-Bu (3.24 g, 28.87 mmol, 2.5 equiv), dicyclohexyl-(2',4',6'-triisopropyl-biphenyl-2-yl)-phosphane (0.11 g, 0.23 mmol, 0.02 equiv; X-Phos ligand [CAS RN 564483-18-7]; commercially available from Strem Chemicals, USA) and tris(dibenzylideneacetone) dipalladium(0) (0.96 g, 0.92 mmol, 0.08 equiv). The reaction mixture was stirred under nitrogen at 100° C. for 16 h, cooled to rt, filtered and the filtrate concentrated by evaporation under reduced pressure. The crude material was purified with silica column chromatography eluting with a gradient of ethyl acetate/triethylamine (10:0→9:1) to provide 1.75 g (52%) of the title compound in 90% purity according to $^1$H NMR. $^1$H NMR (400 MHz, DMSO): δ 1.14-1.29 (m, 2H), 1.40 (s, 9H), 1.84 (d, J=12.8 Hz, 2H), 2.24 (s, 3H), 2.90 (br s, 2H), 3.40-3.53 (m, 1H), 3.86 (d, J=13.0 Hz, 2H), 6.23-6.33 (m, 2H), 6.35 (s, 1H), 7.87 (d, J=5.8 Hz, 1H). MS (ESI): 292.2 [M+H]$^+$.

Step 2: (2-Methyl-pyridin-4-yl)-piperidin-4-yl-amine dihydrochloride

A solution of 4-(2-methyl-pyridin-4-ylamino)-piperidine-1-carboxylic acid tert-butyl ester (1.31 g, 4.50 mmol) in dioxane (20 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 192.1 [M+H]$^+$.

Intermediate A8

(3-Fluoro-pyridin-4-yl)-piperidin-4-yl-amine dihydrochloride

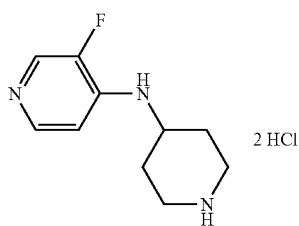

Step 1: 4-(3-Fluoro-pyridin-4-ylamino)-piperidine-1-carboxylic acid tert-butyl ester To a degassed solution of 4-bromo-3-fluoro-pyridine (2.98 g, 16.93 mmol, 1.0 equiv; commercially available) and 4-amino-piperidine-1-carboxylic acid tert-butyl ester (4.07 g, 20.31 mmol, 1.2 equiv; commercially available) in toluene (40 mL) was added KOtert-Bu (4.75 g, 42.32 mmol, 2.5 equiv), dicyclohexyl-(2',4',6'-triisopropyl-biphenyl-2-yl)-phosphane (0.16 g, 0.34 mmol, 0.02 equiv; X-Phos ligand [CAS RN 564483-18-7]; commercially available from Strem Chemicals, USA) and tris(dibenzylideneacetone) dipalladium(0) (1.40 g, 1.35 mmol, 0.08 equiv). The reaction mixture was stirred under nitrogen at 100° C. for 16 h, cooled to rt, filtered and the filtrate concentrated by evaporation under reduced pressure. The crude material was purified with silica column chromatography eluting with a gradient of dichloromethane/methanol (10:0→9:1) and then recrystallized from diethylether to provide 0.20 g (4%) of the title compound in 90% purity according to $^1$H NMR. $^1$H NMR (400 MHz, DMSO): δ 1.27-1.38 (m, 2H), 1.40 (s, 9H), 1.82 (d, J=10.9 Hz, 2H), 2.84 (br s, 2H), 3.51-3.53 (m, 1H), 3.96-3.98 (m, 2H), 6.34 (d, J=7.6 Hz, 1H), 6.79 (dd, J=7.9 Hz, J=5.6 Hz, 1H), 7.95 (d, J=5.5 Hz, 1H), 8.08 (d, J=4.0 Hz, 1H). MS (ESI): 296.2 [M+H]$^+$.

Step 2: (3-Fluoro-pyridin-4-yl)-piperidin-4-yl-amine dihydrochloride

A solution of 4-(3-fluoro-pyridin-4-ylamino)-piperidine-1-carboxylic acid tert-butyl ester (0.16 g, 0.54 mmol) in dioxane (10 mL) and 4 M HCl in dioxane (10 mL) was stirred at rt for 2 h. The solvent was removed under reduced pressure and the crude product used in the consecutive step without further purification assuming quantitative deprotection and formation of the dihydrochloride salt. MS (ISP): 196.3 [M+H]$^+$.

Intermediate A9

Piperidin-4-yl-quinolin-4-yl-amine dihydrochloride

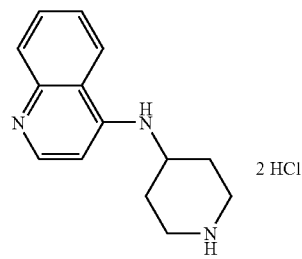

Step 1: 4-(Quinolin-4-ylamino)-piperidine-1-carboxylic acid tert-butyl ester To a degassed solution of 4-bromo-quinoline (4.00 g, 19.23 mmol, 1.0 equiv; commercially available) and 4-amino-piperidine-1-carboxylic acid tert-butyl ester (4.62 g, 23.08 mmol, 1.2 equiv; commercially available) in toluene (40 mL) was added KOtert-Bu (5.40 g, 48.07 mmol, 2.5 equiv), dicyclohexyl-(2',4',6'-triisopropyl-biphenyl-2-yl)-phosphane (0.18 g, 0.39 mmol, 0.02 equiv; X-Phos ligand [CAS RN 564483-18-7]; commercially available from Strem Chemicals, USA) and tris(dibenzylideneacetone) dipalladium(0) (1.59 g, 1.54 mmol, 0.08 equiv). The reaction mixture was stirred under nitrogen at 100° C. for 16 h, cooled to rt, filtered and the filtrate concentrated by evaporation under reduced pressure. The crude material was purified with silica column chromatography eluting with a gradient of ethyl acetate/triethylamine (10:0→20:1) to provide 3.40 g (54%) of the title compound in 90% purity according to $^1$H NMR. $^1$H NMR (400 MHz, DMSO): δ 1.39 (s, 9H), 1.55-1.70 (m, 2H), 1.93 (d, J=10.4 Hz, 2H), 2.93 (br s, 2H), 3.96-4.06 (m, 2H), 4.06-4.15 (m, 1H), 7.00 (d, J=7.0 Hz, 1H), 7.62-7.71 (m, 1H), 7.86-7.95 (m, 2H), 8.54 (d, J=6.9 Hz, 2H), 8.60 (d, J=8.6 Hz, 1H).

Step 2: Piperidin-4-yl-quinolin-4-yl-amine dihydrochloride

A solution of 4-(quinolin-4-ylamino)-piperidine-1-carboxylic acid tert-butyl ester (1.77 g, 5.41 mmol) in dioxane (20 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 228.6 [M+H]+.

Intermediate A10

(7-Chloro-quinolin-4-yl)-piperidin-4-yl-amine dihydrochloride

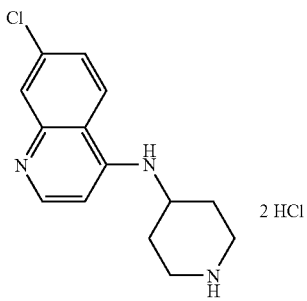

Step 1: 4-(7-Chloro-quinolin-4-ylamino)-piperidine-1-carboxylic acid tert-butyl ester To a degassed solution of 7-chloro-4-iodo-quinoline (5.33 g, 18.42 mmol, 1.0 equiv; commercially available) and 4-amino-piperidine-1-carboxylic acid tert-butyl ester (4.43 g, 22.11 mmol, 1.2 equiv; commercially available) in toluene (40 mL) was added KOtert-Bu (5.17 g, 46.06 mmol, 2.5 equiv), dicyclohexyl-(2',4',6'-triisopropyl-biphenyl-2-yl)-phosphane (0.18 g, 0.37 mmol, 0.02 equiv; X-Phos ligand [CAS RN 564483-18-7]; commercially available from Strem Chemicals, USA) and tris(dibenzylideneacetone) dipalladium(0) (1.53 g, 1.47 mmol, 0.08 equiv). The reaction mixture was stirred under nitrogen at 100° C. for 16 h, cooled to rt, filtered and the filtrate concentrated by evaporation under reduced pressure. The crude material was purified with silica column chromatography eluting with dichloromethane/methanol (20:1+0.5% triethylamine) and then recrystallized from heptane/ethyl acetate to provide 2.20 g (33%) of the title compound in 80% purity according to $^1$H NMR. $^1$H NMR (250 MHz, DMSO): δ 1.42 (s, 9H), 1.46-1.61 (m, 2H), 1.94 (d, J=10.3 Hz, 2H), 2.75-3.03 (m, 2H), 3.88 (br s, 1H), 3.94-4.14 (m, 2H), 6.75 (d, J=6.1 Hz, 1H), 7.56 (d, J=6.9 Hz, 2H), 7.82 (s, 1H), 8.31-8.55 (m, 2H). MS (ESI): 362.2 [M+H]+.

Step 2: (7-Chloro-quinolin-4-yl)-piperidin-4-yl-amine dihydrochloride

A solution of 4-(7-chloro-quinolin-4-ylamino)-piperidine-1-carboxylic acid tert-butyl ester (2.09 g, 5.78 mmol) in dioxane (30 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 262.3 [M+H]+.

Intermediate A11

Piperidin-4-yl-pyrimidin-5-yl-amine dihydrochloride

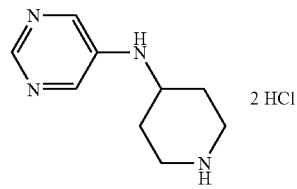

Step 1: 4-(Pyrimidin-5-ylamino)-piperidine-1-carboxylic acid tert-butyl ester A mixture of 5-bromo-pyrimidine (1.59 g, 10.00 mmol, 1.0 equiv; commercially available), 4-amino-piperidine-1-carboxylic acid tert-butyl ester (2.00 g, 10.00 mmol, 1.0 equiv), rac-2,2'-bis(diphenylphosphino)-1,1'-binaphthalene (0.25 g, 0.40 mmol, 0.04 equiv), tris(dibenzylideneacetone)dipalladium(0) (0.21 g, 0.20 mmol, 0.02 equiv) and KOtert-Bu (1.35 g, 12.01 mmol, 1.2 equiv) in toluene (10 mL) was heated under Ar by microwave irradiation to 100° C. for 2 h. The crude reaction mixture was filtered through Hyflo Super Cel, a sat. solution of sodium chloride (100 mL) was added and the mixture extracted with ethyl acetate (3×50 mL). The combined organic phases were concentrated by evaporation under reduced pressure and the residue purified by silica column chromatography using a MPLC system (CombiFlash Companion, Isco Inc.) eluting with a gradient of heptane (+1% triethylamine)/ethyl acetate to provide 1.30 g (47%) of the title compound. MS (ISP): 279.1 [M+H]+.

Step 2: Piperidin-4-yl-pyrimidin-5-yl-amine dihydrochloride

A solution of 4-(pyrimidin-5-ylamino)-piperidine-1-carboxylic acid tert-butyl ester (1.30 g, 4.67 mmol) in 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 179.1 [M+H]+.

Intermediate A12

(2-Phenyl-pyrimidin-5-yl)-piperidin-4-yl-amine dihydrochloride

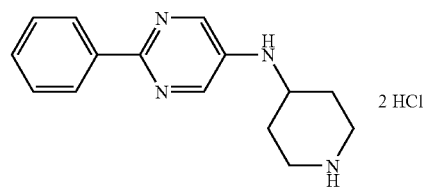

Step 1: 5-Bromo-2-phenyl-pyrimidine

To a degassed solution of phenylboronic acid (8.93 g, 73.22 mmol, 1.0 equiv; commercially available), 5-bromo-2-iodopyrimidine (20.86 g, 73.22 mmol, 1.0 equiv; commercially available) and tetrakis(triphenylphosphine) palladium(0) (0.85 g, 0.73 mmol, 0.01 equiv) in toluene (180 mL) was added Na$_2$CO$_3$ (15.52 g, 146.45 mmol, 2.0 equiv), dissolved in water (60 mL), and the reaction mixture heated to reflux. After 18 h, tetrakis(triphenylphosphine) palladium(0) (0.42 g, 0.37 mmol, 0.005 equiv) was added and the reaction mixture heated for an additional time period of 24 h. The solvent was removed under reduced pressure and the crude reaction product extracted from a sat. solution of NaCl (200 mL) with ethyl acetate (3×150 mL). The combined organic phases were dried over Na$_2$SO$_4$, concentrated by evaporation under reduced pressure and the crude material purified by silica column chromatography eluting with heptane/ethyl acetate (9:1) to provide 8.60 g (50%) of the title compound.

Step 2:
4-(Pyrimidin-5-ylamino)-piperidine-1-carboxylic acid tert-butyl ester

A mixture of 5-bromo-2-phenyl-pyrimidine (3.50 g, 14.89 mmol, 1.0 equiv), 4-amino-piperidine-1-carboxylic acid tert-butyl ester (4.48 g, 22.33 mmol, 1.5 equiv), copper(I) iodide (0.28 g, 1.49 mmol, 0.1 equiv), N,N-diethylsalicylamide (0.58 g, 2.98 mmol, 0.2 equiv) and K$_3$PO$_4$ (3.16 g, 14.89 mmol, 1.0 equiv) in degassed DMF (30 mL) was heated under Ar to 90° C. for 24 h. The solvent was removed under reduced pressure and the crude reaction product extracted from water (300 mL) and 25% NH$_4$OH (30 mL) with ethyl acetate (3×300 mL). The combined organic phases were dried over Na$_2$SO$_4$, concentrated by evaporation under reduced pressure and the crude material purified by silica column chromatography eluting with a gradient of heptane/ethyl acetate (4:1→1:1) to provide 1.98 g (38%) of the title compound. MS (ESI): 377.1 [M+Na]$^+$.

Step 3:
(2-Phenyl-pyrimidin-5-yl)-piperidin-4-yl-amine dihydrochloride

A solution of 4-(pyrimidin-5-ylamino)-piperidine-1-carboxylic acid tert-butyl ester (0.85 g, 2.40 mmol) in dioxane (20 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 255.6 [M+H]$^+$.

Intermediate A13

(2-Morpholin-4-yl-pyrimidin-5-yl)-piperidin-4-yl-amine dihydrochloride

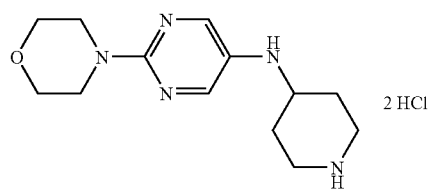

Step 1: 4-(2-Morpholin-4-yl-pyrimidin-5-ylamino)-piperidine-1-carboxylic acid tert-butyl ester To a degassed solution of 4-(5-bromo-pyrimidin-2-yl)-morpholine (4.70 g, 19.26 mmol, 1.0 equiv; commercially available) and 4-amino-piperidine-1-carboxylic acid tert-butyl ester (4.63 g, 23.11 mmol, 1.2 equiv; commercially available) in toluene (40 mL) was added KOtert-Bu (5.40 g, 48.15 mmol, 2.5 equiv), dicyclohexyl-(2',4',6'-triisopropyl-biphenyl-2-yl)-phosphane (0.18 g, 0.39 mmol, 0.02 equiv; X-Phos ligand [CAS RN 564483-18-7]; commercially available from Strem Chemicals, USA) and tris(dibenzylideneacetone)dipalladium(0) (1.60 g, 1.54 mmol, 0.08 equiv). The reaction mixture was stirred under nitrogen at 100° C. for 16 h, cooled to rt, filtered and the filtrate concentrated by evaporation under reduced pressure. The crude material was purified with silica column chromatography eluting with a gradient of heptane/ethyl acetate (3:2→2:3) to provide 0.14 g (2%) of the title compound in 90% purity according to $^1$H NMR. $^1$H NMR (360 MHz, DMSO): δ 1.11-1.25 (m, 2H), 1.39 (s, 9H), 1.84 (d, J=14.1 Hz, 2H), 2.88 (br s, 2H), 3.30 (br s, 1H), 3.46 (t, J=5.0 Hz, 4H), 3.64 (t, J=4.1 Hz, 4H), 3.84 (d, J=12.7 Hz, 2H), 5.03 (d, J=8.6 Hz, 1H), 7.96 (s, 2H). MS (ESI): 364.3 [M+H]$^+$.

Step 2: (2-Morpholin-4-yl-pyrimidin-5-yl)-piperidin-4-yl-amine dihydrochloride

A solution of 4-(2-morpholin-4-yl-pyrimidin-5-ylamino)-piperidine-1-carboxylic acid tert-butyl ester (0.12 g, 0.33 mmol) in dioxane (10 mL) and 4 M HCl in dioxane (10 mL) was stirred at rt for 2 h. The solvent was removed under reduced pressure and the crude product used in the consecutive step without further purification assuming quantitative deprotection and formation of the dihydrochloride salt. MS (ISP): 264.1 [M+H]$^+$.

The aldehyde intermediates B1 to B21 were prepared following literature precedents or in analogy to literature precedents or as described below.

Synthesis of Aldehyde Intermediates B1 to B21 to be used in Table 1

Intermediate B1

3-Ethoxy-4-fluoro-benzaldehyde

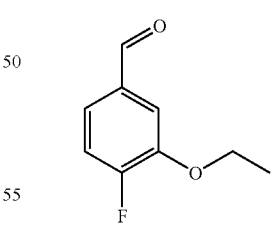

The title compound was prepared according to the procedure described for the synthesis of 4-chloro-3-ethoxy-benzaldehyde (intermediate B2, vide infra) starting from 4-fluoro-3-hydroxy-benzoic acid in 73% overall yield after purification by flash column chromatography on silica eluting with hexane/ethyl acetate (10:1). $^1$H NMR (300 MHz, DMSO): δ 1.32 (t, J=7.0 Hz, 3H), 4.12 (q, 7.0 Hz, 2H), 7.34-7.41 (m, 1H), 7.47-7.56 (m, 2H), 9.87 (s, 1H). MS (ISP): 186.1 [M+NH$_4$]$^+$.

Intermediate B2

4-Chloro-3-ethoxy-benzaldehyde [CAS RN 85259-46-7]

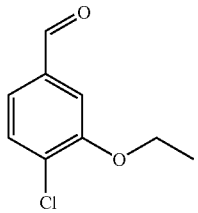

To a solution of 4-chloro-3-hydroxy-benzoic acid (3.0 g, 17.4 mmol, 1.0 equiv) in DMF (15 mL) was added $K_2CO_3$ (4.81 g, 34.8 mmol, 2.0 equiv) and ethyl iodide (4.03 mL, 5.97 g, 38.2 mmol, 2.2 equiv). The reaction mixture was stirred for 6 h at rt, diluted with water (20 mL) and extracted with ethyl acetate (3×50 mL). The organic phases were dried over $Na_2SO_4$ and concentrated to afford 3.6 g (91%) of 4-chloro-3-ethoxy-benzoic acid ethyl ester. The crude ester was then dissolved in THF (20 mL) and cooled to −78° C. under Ar. A solution of diisobutylaluminium hydride (95 mL, 95.0 mmol, 6.0 equiv; 1.0 M solution in THF) was slowly added over a time period of 15 min, the cooling bath removed on completion of addition and the reaction allowed to reach 0° C. After stirring for 1 h, the reaction was cooled to −78° C. and the excess hydride quenched by cautious addition of a solution of 1 M HCl (10 mL). The mixture was brought to rt, the organic phase separated and the aqueous layer extracted with ethyl acetate (3×100 mL). The combined organic phases were dried over $Na_2SO_4$ and concentrated by evaporation under reduced pressure providing 2.94 g (100%) of 4-chloro-3-ethoxy-benzyl alcohol. The crude alcohol (2.94 g, 15.75 mmol, 1.0 equiv) was dissolved in dichloromethane (15 mL) and activated $MnO_2$ (5.48 g, 63.0 mmol, 4.0 equiv) was added. The reaction mixture was stirred for 16 h, after which time the reaction was filtered through Hyflo Super Cel and concentrated. The residue was purified by flash column chromatography on silica eluting with heptane/ethyl acetate (4:1) to yield 1.51 g (52%) of the title compound. $^1$H NMR (300 MHz, $CDCl_3$): δ 1.51 (t, J=7.1 Hz, 3H), 4.19 (q, J=7.1 Hz, 2H), 7.37-7.42 (m, 2H), 7.55 (d, J=9.0 Hz, 1H), 9.94 (s, 1H).

Intermediate B3

3-Ethoxy-4-(1-ethyl-propoxy)-benzaldehyde

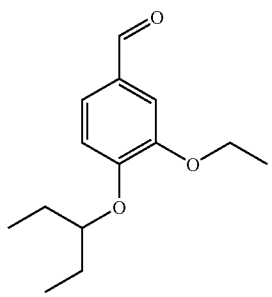

The title compound was prepared analogously to 3-ethoxy-4-methyl-benzaldehyde (intermediate B21, vide infra) by reaction of 3-ethoxy-4-hydroxy-benzaldehyde with 3-bromo-pentane in DMF using $K_2CO_3$ as base. MS (ISP): 237.1 $[M+H]^+$.

Intermediate B4

4-Methoxy-3-propoxy-benzaldehyde [CAS RN 5922-56-5]

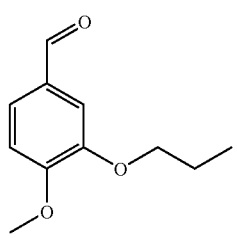

The title compound was prepared by reaction of isovanillin with propyl iodide in DMF using $K_2CO_3$ as base in analogy to the preparation of 3-ethoxy-4-methyl-benzaldehyde (intermediate B21, vide infra).

Intermediate B5

3-Allyloxy-4-methoxy-benzaldehyde [CAS RN 225939-36-6]

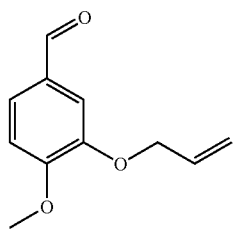

The title compound was prepared analogously to 3-ethoxy-4-methyl-benzaldehyde (intermediate B21, vide infra) by reaction of 3-hydroxy-4-methoxy-benzaldehyde with allyl-bromide in DMF using $K_2CO_3$ as base (see also A. W. White, R. Almassy, A. H. Calvert, N.J. Curtin, R. J. Griffin, Z. Hostomsky, K. Maegley, D. R. Newell, S. Srinivasan and B. T. Golding *J. Med. Chem.* 2000, 43, 4084-4097).

Intermediate B6

3-Butoxy-4-methoxy-benzaldehyde

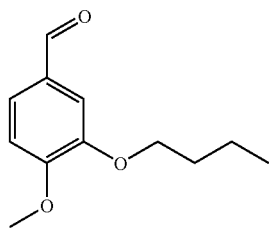

The title compound was prepared analogously to 3-ethoxy-4-methyl-benzaldehyde (intermediate B21, vide infra) by reaction of 3-hydroxy-4-methoxy-benzaldehyde with 4-bromo-butane in DMF using K$_2$CO$_3$ as base. MS (ISP): 209.1 [M+H]$^+$.

Intermediate B7

3-Isobutoxy-4-methoxy-benzaldehyde [CAS RN 57724-26-2]

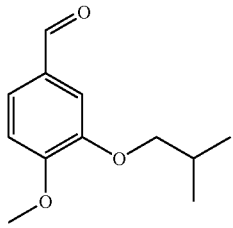

The title compound was prepared by reaction of isovanillin with 1-bromo-2-methyl propane as described in WO 04/000 806 A1 (Elbion AG).

Intermediate B8

8-Ethoxy-2,2-dimethyl-2H-chromene-6-carbaldehyde [CAS RN 210404-30-9]

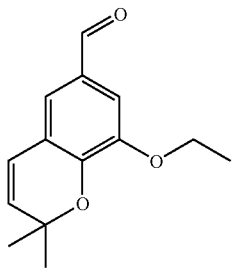

The title compound was prepared according to WO 01/083 476 A1 (Hoffmann-La Roche AG).

Intermediate B9

3,5-Diethoxy-benzaldehyde [CAS RN 120355-79-5]

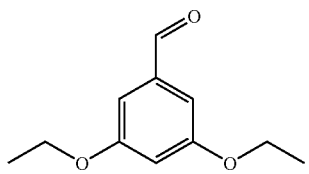

The title compound was prepared analogously to 3-ethoxy-4-methyl-benzaldehyde (intermediate B21, vide infra) by reaction of 3,5-dihydroxybenzaldehyde with ethyl iodide in DMF using K$_2$CO$_3$ as base.

Intermediate B10

3,5-Diisopropoxy-benzaldehyde [CAS RN 94169-64-9]

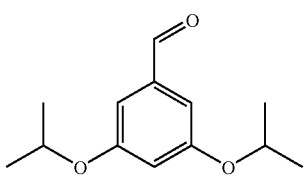

To a solution of 3,5-dihydroxy-benzaldehyde (5.0 g, 36.20 mmol, 1.0 equiv) in anhydrous DMF (30 mL) was added K$_2$CO$_3$ (15.0 g, 108.60 mmol, 3.0 equiv) and 2-bromo-propane (13.36 g, 10.20 mL, 108.60 mmol, 3.0 equiv) and the mixture stirred at 100° C. for 18 h. The K$_2$CO$_3$ was removed by filtration and the organic phase concentrated under reduced pressure. To the residue was added a sat. solution of NaCl (100 mL) and the solution extracted with ethyl acetate (3×100 mL). The combined organic phases were dried over MgSO$_4$ and the product purified by silica column chromatography using a MPLC system (CombiFlash Companion, Isco Inc.) eluting with a gradient of heptane/ethyl acetate affording 6.64 g (83%) of the title compound and 0.59 g (9%) of 3-hydroxy-5-isopropoxy-benzaldehyde (intermediate B20, vide infra). $^1$H NMR (300 MHz, CDCl$_3$): δ 1.35 (d, J=6.1 Hz, 12H), 4.59 (hept, J=6.1 Hz, 2H), 6.66-6.68 (m, 1H), 6.96-6.97 (m, 2H), 9.88 (s, 1H). MS (ISP): 223.1 [M+H]$^+$.

Intermediate B11

2,6-Diethoxy-4-formyl-benzoic acid ethyl ester [CAS RN 55687-55-3]

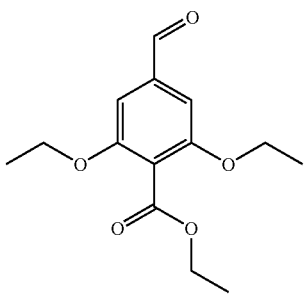

The title compound was prepared as described in DE 243 59 34 (Hoffmann-La Roche AG).

Intermediate B12

3,5-Diethoxy-4-fluoro-benzaldehyde

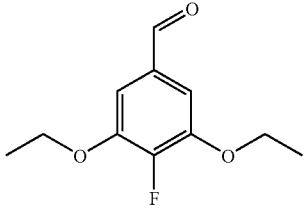

Step 1:
tert-Butyl-(4-fluoro-benzyloxy)-dimethyl-silane

To a solution of (4-fluoro-phenyl)-methanol (12.16 g, 96.4 mmol, 1.0 equiv) in anhydrous DMF (50 mL) at 0° C. under Ar was added imidazole (7.22 g, 106.1 mmol, 1.1 equiv) and tert-butyl-chloro-dimethyl-silane (15.99 g, 106.1 mmol, 1.1 equiv). After the addition was completed the cooling bath was removed and the reaction stirred for 18 h at rt. The reaction mixture was poured on ice, extracted with ethyl acetate (2×100 mL) and the combined organic phases washed with a sat. solution of $Na_2CO_3$ (2×100 mL) and NaCl (2×100 mL). The organic phase was dried over $Na_2SO_4$, concentrated by evaporation under reduced pressure yielding a brown oil that was purified by high vacuum destillation (bp 32-35° C. at 0.1 mbar) to give 23.0 g (99%) of the title compound. $^1$H NMR (400 MHz, CDCl$_3$): δ 0.00 (s, 6H), 0.84 (s, 9H), 4.60 (s, 2H), 6.89-6.94 (m, 2H), 7.16-7.20 (m, 2H). MS (EI): 183.1 [M-tert-Bu]$^+$.

Step 2: 5-(tert-Butyl-dimethyl-silanyloxymethyl)-2-fluoro-phenol

To a solution of tert-butyl-(4-fluoro-benzyloxy)-dimethyl-silane (5.00 g, 20.8 mmol, 1.0 equiv) in anhydrous THF (20 mL) was added at −78° C. under Ar a solution of sec-BuLi (17.6 mL, 22.8 mmol, 1.1 equiv; 1.3 M solution in hexane) within 30 min. Then a solution of trimethyl borate (2.37 mL, 2.20 g, 20.8 mmol, 1.0 equiv) in anhydrous THF (7.5 mL) was added slowly within 30 min and the cooling bath removed. A solution of conc. acetic acid (2.78 mL, 1.87 g, 31.2 mmol, 1.5 equiv) was slowly added followed by addition of a solution of 35% hydrogen peroxide in water (2.0 mL, 2.23 g, 22.9 mmol, 1.1 equiv) and the reaction mixture kept at 0° C. for 30 min. After stirring at rt for an additional 4 h, the reaction was extracted with diethyl ether (2×100 mL) and the combined organic phases washed with a solution of 10% NaOH (2×100 mL) and a sat. solution of NaCl (2×100 mL). The organic phase was dried over $Na_2SO_4$, concentrated by evaporation under reduced pressure and the crude material purified with column chromatography on silica eluting with hexane/ethyl acetate (19:1) providing 4.80 g (90%) of the title compound. $^1$H NMR (400 MHz, CDCl$_3$): δ 0.00 (s, 6H), 0.84 (s, 9H), 4.56 (s, 2H), 4.97 (br s, 1H), 6.68-6.72 (m, 1H), 6.87-6.94 (m, 2H). MS (EI): 256.2 [M]$^+$.

Step 3: 2-(tert-Butyl-dimethyl-silanyloxy)-4-(tert-butyl-dimethyl-silanyloxymethyl)-1-fluoro-benzene To a solution of 5-(tert-butyl-dimethyl-silanyloxymethyl)-2-fluoro-phenol (4.60 g, 17.9 mmol, 1.0 equiv) in anhydrous DMF (20 mL) at 0° C. under Ar was added imidazole (1.34 g, 19.7 mmol, 1.1 equiv) and tert-butyl-chloro-dimethyl-silane (2.97 g, 19.7 mmol, 1.1 equiv). After the addition was completed the cooling bath was removed and the reaction stirred for 18 h at rt. The reaction mixture was poured on ice, extracted with ethyl acetate (2×100 mL) and the combined organic phases washed with a sat. solution of $Na_2CO_3$ (2×100 mL) and NaCl (2×100 mL). The organic phase was dried over $Na_2SO_4$ and concentrated by evaporation under reduced pressure yielding 4.50 g (68%) of the title compound. $^1$H NMR (400 MHz, CDCl$_3$): δ 0.00 (s, 6H), 0.10 (s, 6H), 0.85 (s, 9H), 0.92 (s, 9H), 4.55 (s, 2H), 6.71-6.74 (m, 1H), 6.80-6.83 (m, 1H), 6.87-6.92 (m, 1H). MS (EI): 370.2 [M]$^+$.

Step 4: 3-(tert-Butyl-dimethyl-silanyloxy)-5-(tert-butyl-dimethyl-silanyloxymethyl)-2-fluoro-phenol To a solution of 2-(tert-butyl-dimethyl-silanyloxy)-4-(tert-butyl-dimethyl-silanyloxymethyl)-1-fluoro-benzene (23.70 g, 63.9 mmol, 1.0 equiv) in anhydrous THF (130 mL) was added at −78° C. under Ar a solution of sec-BuLi (54.5 mL, 71.6 mmol, 1.1 equiv; 1.3 M solution in hexane) within 30 min. Then a solution of trimethyl borate (7.13 mL, 6.64 g, 63.9 mmol, 1.0 equiv) in anhydrous THF (30 mL) was added slowly within 30 min and the cooling bath removed. A solution of conc. acetic acid (5.49 mL, 5.76 g, 95.9 mmol, 1.5 equiv) was slowly added followed by addition of a solution of 35% hydrogen peroxide in water (6.2 mL, 6.83 g, 70.3 mmol, 1.1 equiv) and the reaction mixture kept at 0° C. for 30 min. After stirring at rt for an additional 4 h, the reaction was extracted with diethyl ether (2×100 mL) and the combined organic phases washed with a solution of 10% NaOH (2×100 mL) and a sat. solution of NaCl (2×100 mL). The organic phase was dried over $Na_2SO_4$, concentrated by evaporation under reduced pressure and the crude material purified with column chromatography on silica eluting with hexane/ethyl acetate (19:1) providing 15.80 g (64%) of the title compound. $^1$H NMR (400 MHz, CDCl$_3$): δ 0.00 (s, 6H), 0.10 (s, 6H), 0.85 (s, 9H), 0.91 (s, 9H), 4.50 (s, 2H), 4.93 (br s, 1H), 6.37 (d, J=5.6 Hz, 1H), 6.47 (d, J=5.6 Hz, 1H). MS (EI): 329.2 [M-tert-Bu]$^+$.

Step 5: tert-Butyl-(3,5-diethoxy-4-fluoro-benzyloxy)-dimethyl-silane

To a solution of 3-(tert-butyl-dimethyl-silanyloxy)-5-(tert-butyl-dimethyl-silanyloxymethyl)-2-fluoro-phenol (5.80 g, 15.0 mmol, 1.0 equiv) in DMF (60 mL) was added $K_2CO_3$ (4.56 g, 33.0 mmol, 2.2 equiv) and ethyl bromide (2.46 mL, 3.60 g, 33.0 mmol, 2.2 equiv) and the reaction mixture stirred under Ar at 60° C. for 5 h. The $K_2CO_3$ was removed by filtration, the crude reaction mixture concentrated by evaporation under reduced pressure, the residue extracted with ethyl acetate (3×100 mL), the combined organic phases washed with water (2×100 ml) and dried over $Na_2SO_4$. The solvent was removed by evaporation under reduced pressure and the crude material purified with column chromatography on silica eluting with hexane/ethyl acetate (99:1) providing 3.10 g (63%) of the title compound. $^1$H NMR (400 MHz, CDCl$_3$): δ 0.00 (s, 6H), 0.85 (s, 9H), 1.33 (t, J=7.0 Hz, 6H), 4.00 (q, J=7.0 Hz, 4H), 4.55 (s, 2H), 6.47 (d, J=6.8 Hz, 2H). MS (ISP): 329.3 [M+H]$^+$.

Step 6: (3,5-Diethoxy-4-fluoro-phenyl)-methanol

To a solution of tert-butyl-(3,5-diethoxy-4-fluoro-benzyloxy)-dimethyl-silane (1.20 g, 3.65 mmol, 1.0 equiv) in methanol (8 mL) was added Dowex 50W-X8 (0.33 g, cation exchange resin) and the reaction mixture stirred under Ar at rt for 22 h. The resin was removed by filtration and the reaction mixture concentrated by evaporation under reduced pressure yielding the title compound in quantitative yield (0.78 g). $^1$H NMR (400 MHz, CDCl$_3$): δ 1.34 (t, J=7.0 Hz, 6H), 1.57 (t, J=5.4 Hz, 1H), 4.01 (q, J=7.0 Hz, 4H), 4.51 (d, J=5.4 Hz, 2H), 6.51 (d, J=6.8 Hz, 2H). MS (EI): 214.2 [M]$^+$.

Step 7: 3,5-Diethoxy-4-fluoro-benzaldehyde

To a solution of (3,5-diethoxy-4-fluoro-phenyl)-methanol (2.30 g, 10.7 mmol, 1.0 equiv) in 1,2-dichloroethane (50 mL) was added activated MnO$_2$ (2.89 g, 33.3 mmol, 3.1 equiv). The reaction mixture was stirred for 21 h at 50° C. and then filtered through Hyflo Super Cel providing after evaporation of the solvent under reduced pressure 1.90 g (83%) of the title compound. $^1$H NMR (400 MHz, CDCl$_3$): δ 1.38 (t, J=7.0 Hz, 6H), 4.09 (q, J=7.0 Hz, 4H), 7.04 (d, J=7.2 Hz, 2H), 9.75 (s, 1H). MS (EI): 212.1 [M]$^+$.

Intermediate B13

4-Chloro-3,5-diethoxy-benzaldehyde

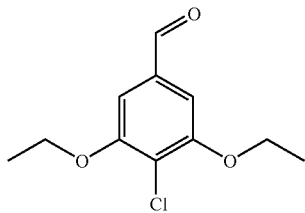

Step 1: 4-Chloro-3,5-diethoxy-benzoic acid ethyl ester

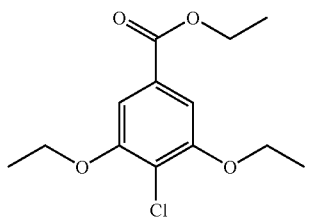

To a solution of 4-amino-3,5-diethoxy-benzoic acid ethyl ester (5.1 g, 20.13 mmol, 1.0 equiv; prepared as described in I. Kompis and A. Wick *Helv. Chim. Acta* 1977, 60, 3025-3034) in water (40 mL) and 37% HCl (40 mL) at 0° C. was added sodium nitrite (1.67 g, 24.16 mmol, 1.2 equiv). After 10 min, copper(I) chloride (12.0 g, 120.81 mmol, 6.0 equiv) was added, the reaction mixture stirred for an additional 5 h at 0° C. and then the ice bath removed. After stirring for 18 h, the crude reaction mixture was adjusted to pH=8 by addition of a solution of 1 M NaOH and the aqueous layer extracted with ethyl acetate (3×100 mL). The combined organic phases were dried over MgSO$_4$, concentrated by evaporation under reduced pressure and the crude material purified by silica column chromatography using a MPLC system (CombiFlash Companion, Isco Inc.) eluting with a gradient of heptane/ethyl acetate providing 5.0 g (91%) of the title compound. $^1$H NMR (300 MHz, CDCl$_3$): δ 1.32 (t, J=7.0 Hz, 4H), 1.40 (t, J=7.0 Hz, 6H), 4.09 (q, J=7.0 Hz, 4H), 4.30 (q, J=7.0 Hz, 2H), 7.18 (s, 2H). $^{13}$C NMR (75 MHz, CDCl$_3$): δ 13.33, 13.66, 60.29, 64.16, 105.75, 115.88, 128.25, 154.49, 165.01. MS (ISP): 273.3 [M+H]$^+$.

Step 2: (4-Chloro-3,5-diethoxy-phenyl)-methanol

To a solution of 4-chloro-3,5-diethoxy-benzoic acid ethyl ester (5.0 g, 18.33 mmol, 1.0 equiv) in dichloromethane (25 mL) was added slowly over a time period of 15 min under slight cooling to −30° C. a solution of diisobutylaluminium hydride (55.0 mL, 55.00 mmol, 3.0 equiv; 1.0 M solution in THF). After 30 min, the excess hydride was quenched by cautious addition of methanol (10 mL) and water (2 mL). The mixture was stirred for 30 min, a solution of 1 M HCl was added and the aqueous layer extracted with ethyl acetate (3×100 mL). The combined organic phases were dried over MgSO$_4$ and concentrated by evaporation under reduced pressure providing 4.0 g (95%) of the title compound. $^1$H NMR (300 MHz, CDCl$_3$): δ 1.45 (t, J=7.0 Hz, 6H), 1.93 (br s, 1H), 4.09 (q, J=7.0 Hz, 4H), 4.62 (s, 2H), 6.57 (s, 2H). $^{13}$C NMR (75 MHz, CDCl$_3$): δ 14.74, 64.96, 65.18, 104.30, 110.65, 140.29, 155.66. MS (ISP): 231.4 [M+H]$^+$.

Step 3: 4-Chloro-3,5-diethoxy-benzaldehyde

To a solution of (4-chloro-3,5-diethoxy-phenyl)-methanol (4.0 g, 17.34 mmol, 1.0 equiv) in THF (40 mL) was added activated MnO$_2$ (15.08 g, 173.4 mmol, 10.0 equiv) and the reaction mixture stirred for 18 h at rt. Filtration through Hyflo Super Cel and purification of the crude material by silica column chromatography using a MPLC system (CombiFlash Companion, Isco Inc.) eluting with a gradient of heptane/ethyl acetate provided 3.7 g (92%) of the title compound. $^1$H NMR (300 MHz, CDCl$_3$): δ 1.50 (t, J=7.0 Hz, 6H), 4.19 (q, J=7.0 Hz, 4H), 7.07 (s, 2H), 9.89 (s, 1H). $^{13}$C NMR (75 MHz, CDCl$_3$): δ 14.61, 65.22, 106.26, 118.64, 135.08, 156.22, 191.01. MS (EI): 229.4 [M]$^+$.

Intermediate B14

4-Bromo-3,5-diethoxy-benzaldehyde [CAS RN 363166-11-4]

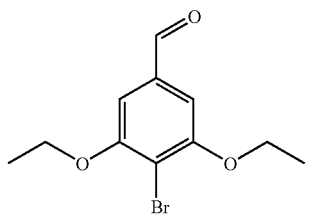

The title compound was prepared from 4-bromo-3,5-dihydroxy-benzoic acid as described in S. P. Dudek, H. D. Sikes and C. E. D. Chidsey *J. Am. Chem. Soc.* 2001, 123, 8033-8038.

Intermediate B15

3,5-Diethoxy-4-pyrrol-1-yl-benzaldehyde

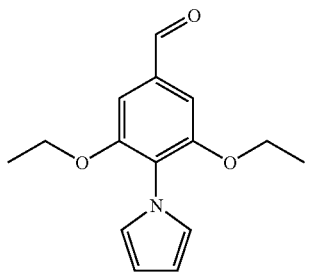

Step 1: 3,5-Diethoxy-4-pyrrol-1-yl-benzoic acid ethyl ester

To a solution of 4-amino-3,5-diethoxy-benzoic acid ethyl ester (3.0 g, 11.84 mmol, 1.0 equiv; prepared as described in I. Kompis and A. Wick Helv. Chim. Acta 1977, 60, 3025-3034) in heptane (10 mL) and conc. acetic acid (0.2 mL) was added 2,5-dimethoxy-tetrahydro-furan (1.88 g, 14.21 mmol, 1.2 equiv). After heating to reflux for 5 h, a Dean-Stark apparatus was attached and the reaction mixture heated for an additional time period of 5 h. Filtration of the crude reaction mixture and crystallization at 0° C. from heptane provided 2.94 g (82%) of the title compound. $^1$H NMR (300 MHz, DMSO): δ 1.15 (t, J=7.0 Hz, 6H), 1.27 (t, J=7.1 Hz, 3H), 3.98 (q, J=7.0 Hz, 4H), 4.28 (q, J=7.1 Hz, 2H), 6.07-6.08 (m, 2H), 6.73-6.74 (m, 2H), 7.22 (s, 2H). $^{13}$C NMR (75 MHz, DMSO): δ 14.11, 14.35, 61.06, 64.57, 106.87, 107.64, 122.61, 123.33, 129.29, 153.75, 165.06. MS (ISP): 303.4 [M+H]$^+$.

Step 2: 3,5-Diethoxy-4-pyrrol-1-yl-benzaldehyde

To a solution of 3,5-diethoxy-4-pyrrol-1-yl-benzoic acid ethyl ester (1.51 g, 4.98 mmol, 1.0 equiv) in toluene (5 mL) was added slowly over a time period of 15 min under slight cooling to 20° C. a solution of diisobutylaluminium hydride (8.9 mL, 12.45 mmol, 2.5 equiv; 20% solution in toluene). After 1 h the excess hydride was quenched by cautious addition of water (10 mL) and a 28% solution of NaOH (2 mL). The mixture was stirred for 30 min and the organic phase filtered over Hyflo Super Cel. The aqueous layer was extracted with toluene (2×50 mL), the combined organic phases washed with a sat. solution of NaCl (2×50 mL) and concentrated by evaporation under reduced pressure to afford 1.30 g (100%) of (3,5-diethoxy-4-pyrrol-1-yl-phenyl)-methanol. The crude alcohol (1.30 g, 4.98 mmol, 1.0 equiv) was dissolved in toluene (20 mL) and activated MnO$_2$ (7.79 g, 89.5 mmol, 18.0 equiv) was added. The reaction mixture was heated to reflux for 7 h, after which time the reaction mixture was filtered through Hyflo Super Cel and concentrated yielding 1.15 g (89% yield) of the title compound. $^1$H NMR (300 MHz, DMSO): δ 1.17 (t, J=7.0 Hz, 6H), 4.02 (q, J=7.0 Hz, 4H), 6.08-6.09 (m, 2H), 6.75-6.76 (m, 2H), 7.25 (s, 2H), 9.89 (s, 1H). MS (ISP): 260.1 [M+H]$^+$.

Intermediate B16

3-(2-Fluoro-ethoxy)-4-methoxy-benzaldehyde

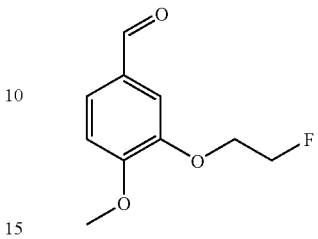

To a solution of 3-hydroxy-4-methoxy-benzaldehyde (10.0 g, 66.0 mmol, 1.0 equiv; commercially available) in anhydrous DMF (40 mL) was added K$_2$CO$_3$ (13.6 g, 99.0 mmol, 1.5 equiv) and 1-bromo-2-fluoro-ethane (9.2 mg, 72.0 mmol, 1.1 equiv) and the mixture stirred at rt for 48 h. The K$_2$CO$_3$ was removed by filtration and the organic phase concentrated under reduced pressure. To the residue was added a sat. solution of NaCl (100 mL) and the solution extracted with ethyl acetate (3×100 mL). The combined organic phases were dried over MgSO$_4$ and the product crystallized from a mixture of isopropanol/diethylether to yield 12.69 g (97%) of the title compound. $^1$H NMR (300 MHz, DMSO): δ 3.89 (s, 3H), 4.24-4.27 (m, 1H), 4.34-4.37 (m, 1H), 4.67-4.70 (m, 1H), 4.83-4.86 (m, 1H), 7.20 (d, J=8.4 Hz, 1H), 7.43 (d, J=1.9 Hz, 1H), 7.59 (dd, J=8.4 Hz, J=1.9 Hz, 1H), 9.84 (s, 1H). MS (ISP): 198.6 [M+H]$^+$.

Intermediate B17

4-Amino-3,5-diethoxy-benzaldehyde

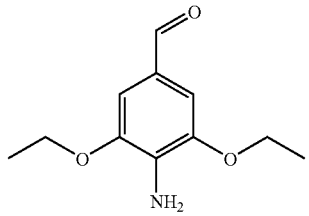

Step 1: (4-Amino-3,5-diethoxy-phenyl)-methanol

To a solution of 4-amino-3,5-diethoxy-benzoic acid ethyl ester (2.8 g, 11.05 mmol, 1.0 equiv; prepared as described in I. Kompis, A. Wick *Helv. Chim. Acta* 1977, 60, 3025-3034) in dichloromethane (50 mL) at 0° C. under Ar was slowly added diisobutylaluminium hydride (27.6 mL, 27.64 mmol, 2.5 equiv; 1.0 M solution in dichloromethane) over a time period of 15 min and the cooling bath removed on completion of addition. After stirring for 18 h, the excess hydride was quenched by cautious addition of a sat. solution of potassium sodium tartrate (10 mL). The solidified mixture was extracted with dichloromethane (5×200 mL) and THF (2×150 mL), the combined organic phases washed with water (3×100 mL), dried over MgSO$_4$, concentrated by evaporation under reduced pressure and the crude material purified by column chromatography on silica eluting with a gradient of heptane/ ethyl acetate (4:1→1:1) providing 1.10 g (47%) of the title compound. $^1$H NMR (300 MHz, CDCl$_3$): δ 1.42 (t, J=7.0 Hz, 3H), 3.82 (br s, 2H), 4.05 (q, J=7.0 Hz, 2H), 4.54 (s, 2H), 6.50 (s, 2H). $^{13}$C NMR (75 MHz, CDCl$_3$): δ 15.03, 64.21, 66.00, 104.51, 125.44, 129.89, 146.71. MS (ISP): 211.9 [M+H]$^+$.

Step 2: 4-Amino-3,5-diethoxy-benzaldehyde

To a solution of (4-amino-3,5-diethoxy-phenyl)-methanol (0.79 g, 3.74 mmol, 1.0 equiv) in DMF (20 mL) was added activated MnO$_2$ (1.63 g, 18.70 mmol, 5.0 equiv). The reaction mixture was stirred for 24 h at rt, filtered through Hyflo Super Cel, the filtrate extracted with ethyl acetate (3×50 mL) and the combined organic phases dried over MgSO$_4$ providing 0.69 g (88%) of the title compound. $^1$H NMR (300 MHz, DMSO): δ 1.46 (t, J=7.0 Hz, 3H), 4.15 (q, J=7.0 Hz, 2H), 4.50 (br s, 2H), 7.04 (s, 2H), 9.70 (s, 1H). MS (ISP): 210.0 [M+H]$^+$.

Intermediate B18

2,6-Diethoxy-4'-fluoro-biphenyl-4-carbaldehyde

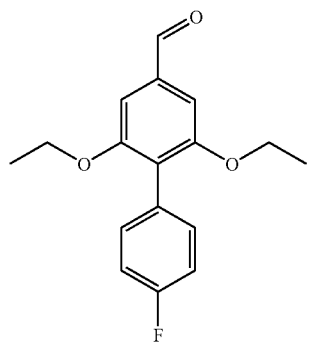

3,5-Diethoxy-4-iodo-benzaldehyde (14.05 g, 43.89 mmol, 1.0 equiv; prepared as described in WO 01/326 33 A1 (F. Hoffmann-La Roche AG); [CAS RN 338454-05-0]) was dissolved under Ar in toluene (180 mL) and water (20 mL) and treated successively with 4-fluorophenyl boronic acid (12.28 g, 87.78 mmol, 2.0 equiv), K$_3$PO$_4$ (50.12 g, 236.12 mmol, 5.38 equiv), tricyclohexylphosphine (2.80 g, 9.66 mmol, 0.22 equiv), and palladium(II) acetate (1.08 g, 4.83 mmol, 0.11 equiv). The reaction mixture was heated to 100° C. for 18 h under scrupulous exclusion of oxygen, when GC indicated the absence of starting iodo-compound. The reaction mixture was poured on crashed ice/NH$_4$Cl, extracted with ethyl acetate (2×200 mL) and the combined organic phases washed with a sat. solution of NaCl (2×100 mL) and water (2×100 mL). The organic phase was dried over Na$_2$SO$_4$, concentrated by evaporation under reduced pressure and the crude material purified by silica column chromatography eluting with a mixture of hexane/ethyl acetate (9:1). Recrystallization from hexane/ethyl acetate provided 10.44 g (83%) of the title compound as white crystals. MS (EI): 288.2 [M]$^+$.

Intermediate B19

5-Ethoxy-2-fluoro-4-(2-hydroxy-ethoxy)-benzaldehyde [CAS RN 376600-66-7]

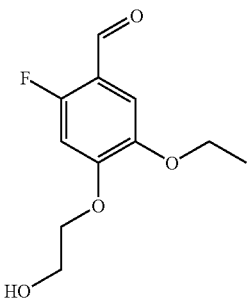

The title compound was prepared according to WO 01/090 051 (Hoffmann-La Roche AG).

Intermediate B20

3-Hydroxy-5-isopropoxy-benzaldehyde

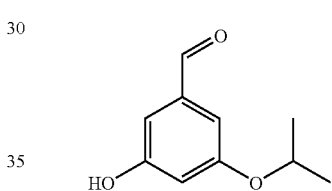

The title compound was isolated as a side-product in the synthesis of 3,5-diisopropoxy-benzaldehyde (intermediate B10). $^1$H NMR (300 MHz, CDCl$_3$): δ1.34 (d, J=6.1 Hz, 6H), 4.58 (hept, J=6.1 Hz, 1H), 6.28 (br s, 1H), 6.68-6.69 (m, 1H), 6.95-6.98 (m, 2H), 9.85 (s, 1H). MS (ISN): 179.1 [M−H]$^−$.

Intermediate B21

3-Ethoxy-4-methyl-benzaldehyde [CAS RN 157143-20-9]

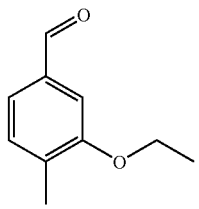

The title compound was prepared by reaction of commercially available 3-hydroxy-4-methyl-benzaldehyde with ethyl iodide in DMF using K$_2$CO$_3$ as base in analogy to the procedure described in M. J. Ashton, D. C. Cook, G. Fenton, J.-A. Karlsson, M. N. Palfreyman, D. Raeburn, A. J. Ratcliffe, J. E. Souness, S. Thurairatnam and N. Vicker *J. Med. Chem.* 1994, 37, 1696-1703.

Examples 2 to 237

According to the procedure described for the synthesis of example 1/step 3 further pyridine, quinoline and pyrimidine derivatives have been synthesized from piperidin-4-yl-pyridin-3-yl-amine dihydrochloride (intermediate A1), (6-morpholin-4-yl-pyridin-3-yl)-piperidin-4-yl-amine dihydrochloride (intermediate A2), N-[5-(piperidin-4-ylamino)-pyridin-2-yl]-acetamide dihydrochloride (intermediate A3), 3-methyl-N$^5$-piperidin-4-yl-pyridine-2,5-diamine dihydrochloride (intermediate A4), N-[6-methyl-5-(piperidin-4-ylamino)-pyridin-2-yl]-acetamide dihydrochloride (intermediate A5), piperidin-4-yl-quinolin-3-yl-amine dihydrochloride (intermediate A6), (2-methyl-pyridin-4-yl)-piperidin-4-yl-amine dihydrochloride (intermediate A7), (3-fluoro-pyridin-4-yl)-piperidin-4-yl-amine dihydrochloride (intermediate A8), piperidin-4-yl-quinolin-4-yl-amine dihydrochloride (intermediate A9), (7-chloro-quinolin-4-yl)-piperidin-4-yl-amine dihydrochloride (intermediate A10), piperidin-4-yl-pyrimidin-5-yl-amine dihydrochloride (intermediate A11), (2-phenyl-pyrimidin-5-yl)-piperidin-4-yl-amine dihydrochloride (intermediate A12) and (2-morpholin-4-yl-pyrimidin-5-yl)-piperidin-4-yl-amine dihydrochloride (intermediate A 13) and the respective aldehyde intermediate as indicated in Table 1. The results are compiled in Table 1 and comprise example 2 to example 237.

TABLE 1

| No | MW | Compound Name | Starting Materials | ISP [M + H]$^+$ |
|---|---|---|---|---|
| 2 | 329.42 | [1-(3-ethoxy-4-fluoro-benzyl)-piperidin-4-yl]-pyridin-3-yl-amine | piperidin-4-yl-pyridin-3-yl-amine dihydrochloride (intermediate A1) and 3-ethoxy-4-fluoro-benzaldehyde (intermediate B1) | [M + H]$^+$ 330.3 |
| 3 | 345.87 | [1-(4-chloro-3-ethoxy-benzyl)-piperidin-4-yl]-pyridin-3-yl-amine | piperidin-4-yl-pyridin-3-yl-amine dihydrochloride (intermediate A1) and 4-chloro-3-ethoxy-benzaldehyde (intermediate B2) | [M + H]$^+$ 346.1 |
| 4 | 341.45 | [1-(3-ethoxy-4-methoxy-benzyl)-piperidin-4-yl]-pyridin-3-yl-amine | piperidin-4-yl-pyridin-3-yl-amine dihydrochloride (intermediate A1) and 3-ethoxy-4-methoxy-benzaldehyde (commercially available) | [M + H]$^+$ 342.1 |
| 5 | 367.49 | [1-(4-allyloxy-3-ethoxy-benzyl)-piperidin-4-yl]-pyridin-3-yl-amine | piperidin-4-yl-pyridin-3-yl-amine dihydrochloride (intermediate A1) and 4-allyloxy-3-ethoxy-benzaldehyde (commercially available) | [M + H]$^+$ 368.1 |
| 6 | 383.54 | [1-(3-ethoxy-4-isobutoxy-benzyl)-piperidin-4-yl]-pyridin-3-yl-amine | piperidin-4-yl-pyridin-3-yl-amine dihydrochloride (intermediate A1) and 3-ethoxy-4-isobutoxy-benzaldehyde (commercially available) | [M + H]$^+$ 384.4 |
| 7 | 397.56 | {1-[3-ethoxy-4-(1-ethyl-propoxy)-benzyl]-piperidin-4-yl}-pyridin-3-yl-amine | piperidin-4-yl-pyridin-3-yl-amine dihydrochloride (intermediate A1) and 3-ethoxy-4-(1-ethyl-propoxy)-benzaldehyde (intermediate B3) | [M + H]$^+$ 398.3 |
| 8 | 395.55 | [1-(4-cyclopentyloxy-3-ethoxy-benzyl)-piperidin-4-yl]-pyridin-3-yl-amine | piperidin-4-yl-pyridin-3-yl-amine dihydrochloride (intermediate A1) and 4-cyclopentyloxy-3-ethoxy-benzaldehyde (commercially available) | [M + H]$^+$ 396.3 |
| 9 | 417.55 | [1-(4-benzyloxy-3-ethoxy-benzyl)-piperidin-4-yl]-pyridin-3-yl-amine | piperidin-4-yl-pyridin-3-yl-amine dihydrochloride (intermediate A1) and 4-benzyloxy-3-ethoxy-benzaldehyde (commercially available) | [M + H]$^+$ 418.1 |
| 10 | 377.43 | [1-(4-difluoromethoxy-3-ethoxy-benzyl)-piperidin-4-yl]-pyridin-3-yl-amine | piperidin-4-yl-pyridin-3-yl-amine dihydrochloride (intermediate A1) and 4-difluoromethoxy-3-ethoxy-benzaldehyde (commercially available) | [M + H]$^+$ 378.5 |
| 11 | 355.48 | [1-(4-methoxy-3-propoxy-benzyl)-piperidin-4-yl]-pyridin-3-yl-amine | piperidin-4-yl-pyridin-3-yl-amine dihydrochloride (intermediate A1) and 4-methoxy-3-propoxy-benzaldehyde (intermediate B4) | [M + H]$^+$ 356.1 |
| 12 | 353.47 | [1-(3-allyloxy-4-methoxy-benzyl)- | piperidin-4-yl-pyridin-3-yl-amine dihydrochloride | [M + H]$^+$ 354.3 |

TABLE 1-continued

| No | MW | Compound Name | Starting Materials | ISP [M + H]+ |
|---|---|---|---|---|
|  |  | piperidin-4-yl]-pyridin-3-yl-amine | (intermediate A1) and 3-allyloxy-4-methoxy-benzaldehyde (intermediate B5) |  |
| 13 | 369.51 | [1-(3-butoxy-4-methoxy-benzyl)-piperidin-4-yl]-pyridin-3-yl-amine | piperidin-4-yl-pyridin-3-yl-amine dihydrochloride (intermediate A1) and 3-butoxy-4-methoxy-benzaldehyde (intermediate B6) | [M + H]+ 370.1 |
| 14 | 369.51 | [1-(3-isobutoxy-4-methoxy-benzyl)-piperidin-4-yl]-pyridin-3-yl-amine | piperidin-4-yl-pyridin-3-yl-amine dihydrochloride (intermediate A1) and 3-isobutoxy-4-methoxy-benzaldehyde (intermediate B7) | [M + H]+ 370.1 |
| 15 | 381.52 | [1-(3-cyclopentyloxy-4-methoxy-benzyl)-piperidin-4-yl]-pyridin-3-yl-amine | piperidin-4-yl-pyridin-3-yl-amine dihydrochloride (intermediate A1) and 3-cyclopentyloxy-4-methoxy-benzaldehyde (commercially available) | [M + H]+ 382.3 |
| 16 | 393.53 | [1-(8-ethoxy-2,2-dimethyl-2H-chromen-6-ylmethyl)-piperidin-4-yl]-pyridin-3-yl-amine | piperidin-4-yl-pyridin-3-yl-amine dihydrochloride (intermediate A1) and 8-ethoxy-2,2-dimethyl-2H-chromene-6-carbaldehyde (intermediate B8) | [M + H]+ 394.1 |
| 17 | 355.48 | [1-(3,5-diethoxy-benzyl)-piperidin-4-yl]-pyridin-3-yl-amine | piperidin-4-yl-pyridin-3-yl-amine dihydrochloride (intermediate A1) and 3,5-diethoxy-benzaldehyde (intermediate B9) | [M + H]+ 356.2 |
| 18 | 383.54 | [1-(3,5-diisopropoxy-benzyl)-piperidin-4-yl]-pyridin-3-yl-amine | piperidin-4-yl-pyridin-3-yl-amine dihydrochloride (intermediate A1) and 3,5-diisopropoxy-benzaldehyde (intermediate B10) | [M + H]+ 384.3 |
| 19 | 427.54 | 2,6-diethoxy-4-[4-(pyridin-3-ylamino)-piperidin-1-ylmethyl]-benzoic acid ethyl ester | piperidin-4-yl-pyridin-3-yl-amine dihydrochloride (intermediate A1) and 2,6-diethoxy-4-formyl-benzoic acid ethyl ester (intermediate B11) | [M + H]+ 428.4 |
| 20 | 373.47 | [1-(3,5-diethoxy-4-fluoro-benzyl)-piperidin-4-yl]-pyridin-3-yl-amine | piperidin-4-yl-pyridin-3-yl-amine dihydrochloride (intermediate A1) and 3,5-diethoxy-4-fluoro-benzaldehyde (intermediate B12) | [M + H]+ 374.3 |
| 21 | 389.93 | [1-(4-chloro-3,5-diethoxy-benzyl)-piperidin-4-yl]-pyridin-3-yl-amine | piperidin-4-yl-pyridin-3-yl-amine dihydrochloride (intermediate A1) and 4-chloro-3,5-diethoxy-benzaldehyde (intermediate B13) | [M + H]+ 390.1 |
| 22 | 434.38 | [1-(4-bromo-3,5-diethoxy-benzyl)-piperidin-4-yl]-pyridin-3-yl-amine | piperidin-4-yl-pyridin-3-yl-amine dihydrochloride (intermediate A1) and 4-bromo-3,5-diethoxy-benzaldehyde (intermediate B14) | [M + H]+ 436.0 |
| 23 | 420.56 | [1-(3,5-diethoxy-4-pyrrol-1-yl-benzyl)-piperidin-4-yl]-pyridin-3-yl-amine | piperidin-4-yl-pyridin-3-yl-amine dihydrochloride (intermediate A1) and 3,5-diethoxy-4-pyrrol-1-yl-benzaldehyde (intermediate B15) | [M + H]+ 421.1 |
| 24 | 414.52 | [1-(3-ethoxy-4-fluoro-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 3-ethoxy-4-fluoro-benzaldehyde (intermediate B1) | [M + H]+ 415.2 |
| 25 | 430.98 | [1-(4-chloro-3-ethoxy-benzyl)-piperidin-4-yl]- | (6-morpholin-4-yl-pyridin-3-yl)-piperidin-4-yl-amine | [M + H]+ 431.2 |

TABLE 1-continued

| No | MW | Compound Name | Starting Materials | ISP [M + H]+ |
|---|---|---|---|---|
|  |  | (6-morpholin-4-yl-pyridin-3-yl)-amine | dihydrochloride (intermediate A2) and 4-chloro-3-ethoxy-benzaldehyde (intermediate B2) |  |
| 26 | 426.56 | [1-(3-ethoxy-4-methoxy-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 3-ethoxy-4-methoxy-benzaldehyde (commercially available) | [M + H]+ 427.3 |
| 27 | 480.65 | [1-(4-cyclopentyloxy-3-ethoxy-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 4-cyclopentyloxy-3-ethoxy-benzaldehyde (commercially available) | [M + H]+ 481.5 |
| 28 | 502.66 | [1-(4-benzyloxy-3-ethoxy-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 4-benzyloxy-3-ethoxy-benzaldehyde (commercially available) | [M + H]+ 503.3 |
| 29 | 462.54 | [1-(4-difluoromethoxy-3-ethoxy-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 4-difluoromethoxy-3-ethoxy-benzaldehyde (commercially available) | [M + H]+ 463.1 |
| 30 | 440.59 | [1-(4-methoxy-3-propoxy-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 4-methoxy-3-propoxy-benzaldehyde (intermediate B4) | [M + H]+ 441.3 |
| 31 | 440.59 | [1-(3-isopropoxy-4-methoxy-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 3-isopropoxy-4-methoxy-benzaldehyde (commercially available) | [M + H]+ 441.3 |
| 32 | 444.55 | {1-[3-(2-fluoro-ethoxy)-4-methoxy-benzyl]-piperidin-4-yl}-(6-morpholin-4-yl-pyridin-3-yl)-amine | (6-morpholin-4-yl-pyridin-3-yl)-piperidin-4-yl-amine dihydrochloride (intermediate A2) and 3-(2-fluoro-ethoxy)-4-methoxy-benzaldehyde (intermediate B16) | [M + H]+ 445.2 |
| 33 | 438.57 | [1-(3-allyloxy-4-methoxy-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 3-allyloxy-4-methoxy-benzaldehyde (intermediate B5) | [M + H]+ 439.2 |
| 34 | 454.61 | [1-(3-isobutoxy-4-methoxy-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 3-isobutoxy-4-methoxy-benzaldehyde (intermediate B7) | [M + H]+ 455.4 |
| 35 | 466.63 | [1-(3-cyclopentyloxy-4-methoxy-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 3-cyclopentyloxy-4-methoxy-benzaldehyde (commercially available) | [M + H]+ 467.2 |
| 36 | 478.64 | [1-(8-ethoxy-2,2-dimethyl-2H-chromen-6-ylmethyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 8-ethoxy-2,2-dimethyl-2H-chromene-6-carbaldehyde (intermediate B8) | [M + H]+ 479.3 |
| 37 | 440.59 | [1-(3,5-diethoxy-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 3,5-diethoxy-benzaldehyde (intermediate B9) | [M + H]+ 441.3 |

TABLE 1-continued

| No | MW | Compound Name | Starting Materials | ISP [M + H]+ |
|---|---|---|---|---|
| 38 | 468.64 | [1-(3,5-diisopropoxy-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 3,5-diisopropoxy-benzaldehyde (intermediate B10) | [M + H]+ 469.2 |
| 39 | 458.58 | [1-(3,5-diethoxy-4-fluoro-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 3,5-diethoxy-4-fluoro-benzaldehyde (intermediate B12) | [M + H]+ 459.3 |
| 40 | 475.03 | [1-(4-chloro-3,5-diethoxy-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 4-chloro-3,5-diethoxy-benzaldehyde (intermediate B13) | [M + H]+ 475.2 |
| 41 | 519.49 | [1-(4-bromo-3,5-diethoxy-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 4-bromo-3,5-diethoxy-benzaldehyde (intermediate B14) | [M + H]+ 521.3 |
| 42 | 455.60 | [1-(4-amino-3,5-diethoxy-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 4-amino-3,5-diethoxy-benzaldehyde (intermediate B17) | [M + H]+ 456.3 |
| 43 | 505.66 | [1-(3,5-diethoxy-4-pyrrol-1-yl-benzyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 3,5-diethoxy-4-pyrrol-1-yl-benzaldehyde (intermediate B15) | [M + H]+ 506.4 |
| 44 | 534.68 | [1-(2,6-diethoxy-4'-fluoro-biphenyl-4-ylmethyl)-piperidin-4-yl]-(6-morpholin-4-yl-pyridin-3-yl)-amine | (6-morpholin-4-yl-pyridin-3-yl)-piperidin-4-yl-amine dihydrochloride (intermediate A2) and 2,6-diethoxy-4'-fluoro-biphenyl-4-carbaldehyde (intermediate B18) | [M + H]+ 535.5 |
| 45 | 386.47 | N-{5-[1-(3-ethoxy-4-fluoro-benzyl)-piperidin-4-ylamino]-pyridin-2-yl}-acetamide | N-[5-(piperidin-4-ylamino)-pyridin-2-yl]-acetamide dihydrochloride (intermediate A3) and 3-ethoxy-4-fluoro-benzaldehyde (intermediate B1) | [M + H]+ 387.2 |
| 46 | 402.93 | N-{5-[1-(4-chloro-3-ethoxy-benzyl)-piperidin-4-ylamino]-pyridin-2-yl}-acetamide | N-[5-(piperidin-4-ylamino)-pyridin-2-yl]-acetamide dihydrochloride (intermediate A3) and 4-chloro-3-ethoxy-benzaldehyde (intermediate B2) | [M + H]+ 403.2 |
| 47 | 398.51 | N-{5-[1-(3-ethoxy-4-methoxy-benzyl)-piperidin-4-ylamino]-pyridin-2-yl}-acetamide | N-[5-(piperidin-4-ylamino)-pyridin-2-yl]-acetamide dihydrochloride (intermediate A3) and 3-ethoxy-4-methoxy-benzaldehyde (commercially available) | [M + H]+ 399.2 |
| 48 | 453.3 | N-{5-[1-(4-cyclopentyloxy-3-ethoxy-benzyl)-piperidin-4-ylamino]-pyridin-2-yl}-acetamide | N-[5-(piperidin-4-ylamino)-pyridin-2-yl]-acetamide dihydrochloride (intermediate A3) and 4-cyclopentyloxy-3-ethoxy-benzaldehyde (commercially available) | [M + H]+ 453.3 |
| 49 | 474.60 | N-{5-[1-(4-benzyloxy-3-ethoxy-benzyl)-piperidin-4-ylamino]-pyridin-2-yl}-acetamide | N-[5-(piperidin-4-ylamino)-pyridin-2-yl]-acetamide dihydrochloride (intermediate A3) and 4-benzyloxy-3-ethoxy-benzaldehyde (commercially available) | [M + H]+ 475.2 |
| 50 | 434.49 | N-{5-[1-(4-difluoromethoxy-3-ethoxy-benzyl)-piperidin-4-ylamino]- | N-[5-(piperidin-4-ylamino)-pyridin-2-yl]-acetamide dihydrochloride (intermediate A3) and 4-difluoromethoxy-3- | [M + H]+ 435.2 |

TABLE 1-continued

| No | MW | Compound Name | Starting Materials | ISP [M + H]+ |
|---|---|---|---|---|
| | | pyridin-2-yl}-acetamide | ethoxy-benzaldehyde (commercially available) | |
| 51 | 412.53 | N-{5-[1-(4-methoxy-3-propoxy-benzyl)-piperidin-4-ylamino]-pyridin-2-yl}-acetamide | N-[5-(piperidin-4-ylamino)-pyridin-2-yl]-acetamide dihydrochloride (intermediate A3) and 4-methoxy-3-propoxy-benzaldehyde (intermediate B4) | [M + H]+ 413.2 |
| 52 | 412.53 | N-{5-[1-(3-isopropoxy-4-methoxy-benzyl)-piperidin-4-ylamino]-pyridin-2-yl}-acetamide | N-[5-(piperidin-4-ylamino)-pyridin-2-yl]-acetamide dihydrochloride (intermediate A3) and 3-isopropoxy-4-methoxy-benzaldehyde (commercially available) | [M + H]+ 413.2 |
| 53 | 426.56 | N-{5-[1-(3-isobutoxy-4-methoxy-benzyl)-piperidin-4-ylamino]-pyridin-2-yl}-acetamide | N-[5-(piperidin-4-ylamino)-pyridin-2-yl]-acetamide dihydrochloride (intermediate A3) and 3-isobutoxy-4-methoxy-benzaldehyde (intermediate B7) | [M + H]+ 427.3 |
| 54 | 438.57 | N-{5-[1-(3-cyclopentyloxy-4-methoxy-benzyl)-piperidin-4-ylamino]-pyridin-2-yl}-acetamide | N-[5-(piperidin-4-ylamino)-pyridin-2-yl]-acetamide dihydrochloride (intermediate A3) and 3-cyclopentyloxy-4-methoxy-benzaldehyde (commercially available) | [M + H]+ 439.3 |
| 55 | 450.58 | N-{5-[1-(8-ethoxy-2,2-dimethyl-2H-chromen-6-ylmethyl)-piperidin-4-ylamino]-pyridin-2-yl}-acetamide | N-[5-(piperidin-4-ylamino)-pyridin-2-yl]-acetamide dihydrochloride (intermediate A3) and 8-ethoxy-2,2-dimethyl-2H-chromene-6-carbaldehyde (intermediate B8) | [M + H]+ 451.1 |
| 56 | 412.53 | N-{5-[1-(3,5-diethoxy-benzyl)-piperidin-4-ylamino]-pyridin-2-yl}-acetamide | N-[5-(piperidin-4-ylamino)-pyridin-2-yl]-acetamide dihydrochloride (intermediate A3) and 3,5-diethoxy-benzaldehyde (intermediate B9) | [M + H]+ 413.2 |
| 57 | 440.59 | N-{5-[1-(3,5-diisopropoxy-benzyl)-piperidin-4-ylamino]-pyridin-2-yl}-acetamide | N-[5-(piperidin-4-ylamino)-pyridin-2-yl]-acetamide dihydrochloride (intermediate A3) and 3,5-diisopropoxy-benzaldehyde (intermediate B10) | [M + H]+ 441.3 |
| 58 | 430.52 | N-{5-[1-(3,5-diethoxy-4-fluoro-benzyl)-piperidin-4-ylamino]-pyridin-2-yl}-acetamide | N-[5-(piperidin-4-ylamino)-pyridin-2-yl]-acetamide dihydrochloride (intermediate A3) and 3,5-diethoxy-4-fluoro-benzaldehyde (intermediate B12) | [M + H]+ 431.2 |
| 59 | 446.98 | N-{5-[1-(4-chloro-3,5-diethoxy-benzyl)-piperidin-4-ylamino]-pyridin-2-yl}-acetamide | N-[5-(piperidin-4-ylamino)-pyridin-2-yl]-acetamide dihydrochloride (intermediate A3) and 4-chloro-3,5-diethoxy-benzaldehyde (intermediate B13) | [M + H]+ 447.1 |
| 60 | 491.43 | N-{5-[1-(4-bromo-3,5-diethoxy-benzyl)-piperidin-4-ylamino]-pyridin-2-yl}-acetamide | N-[5-(piperidin-4-ylamino)-pyridin-2-yl]-acetamide dihydrochloride (intermediate A3) and 4-bromo-3,5-diethoxy-benzaldehyde (intermediate B14) | [M + H]+ 493.3 |
| 61 | 427.55 | N-{5-[1-(4-amino-3,5-diethoxy-benzyl)-piperidin-4-ylamino]-pyridin-2-yl}-acetamide | N-[5-(piperidin-4-ylamino)-pyridin-2-yl]-acetamide dihydrochloride (intermediate A3) and 4-amino-3,5-diethoxy-benzaldehyde (intermediate B17) | [M + H]+ 428.4 |
| 62 | 477.61 | N-{5-[1-(3,5-diethoxy-4-pyrrol-1-yl-benzyl)-piperidin-4-ylamino]-pyridin-2-yl}-acetamide | N-[5-(piperidin-4-ylamino)-pyridin-2-yl]-acetamide dihydrochloride (intermediate A3) and 3,5-diethoxy-4-pyrrol-1-yl-benzaldehyde (intermediate B15) | [M + H]+ 478.2 |
| 63 | 506.62 | N-{5-[1-(2,6-diethoxy-4'-fluoro-biphenyl-4- | N-[5-(piperidin-4-ylamino)-pyridin-2-yl]-acetamide | [M + H]+ 507.4 |

TABLE 1-continued

| No | MW | Compound Name | Starting Materials | ISP [M + H]+ |
|---|---|---|---|---|
| | | ylmethyl)-piperidin-4-ylamino]-pyridin-2-yl}-acetamide | dihydrochloride (intermediate A3) and 2,6-diethoxy-4'-fluoro-biphenyl-4-carbaldehyde (intermediate B18) | |
| 64 | 358.46 | N⁵-[1-(3-ethoxy-4-fluoro-benzyl)-piperidin-4-yl]-3-methyl-pyridine-2,5-diamine | 3-methyl-N⁵-piperidin-4-yl-pyridine-2,5-diamine dihydrochloride (intermediate A4) and 3-ethoxy-4-fluoro-benzaldehyde (intermediate B1) | [M + H]+ 359.3 |
| 65 | 374.92 | N⁵-[1-(4-chloro-3-ethoxy-benzyl)-piperidin-4-yl]-3-methyl-pyridine-2,5-diamine | 3-methyl-N⁵-piperidin-4-yl-pyridine-2,5-diamine dihydrochloride (intermediate A4) and 4-chloro-3-ethoxy-benzaldehyde (intermediate B2) | [M + H]+ 375.3 |
| 66 | 370.50 | N⁵-[1-(3-ethoxy-4-methoxy-benzyl)-piperidin-4-yl]-3-methyl-pyridine-2,5-diamine | 3-methyl-N⁵-piperidin-4-yl-pyridine-2,5-diamine dihydrochloride (intermediate A4) and 3-ethoxy-4-methoxy-benzaldehyde (commercially available) | [M + H]+ 371.3 |
| 67 | 398.55 | N⁵-[1-(3-ethoxy-4-isopropoxy-benzyl)-piperidin-4-yl]-3-methyl-pyridine-2,5-diamine | 3-methyl-N⁵-piperidin-4-yl-pyridine-2,5-diamine dihydrochloride (intermediate A4) and 3-ethoxy-4-isopropoxy-benzaldehyde (commercially available) | [M + H]+ 399.3 |
| 68 | 406.48 | N⁵-[1-(4-difluoromethoxy-3-ethoxy-benzyl)-piperidin-4-yl]-3-methyl-pyridine-2,5-diamine | 3-methyl-N⁵-piperidin-4-yl-pyridine-2,5-diamine dihydrochloride (intermediate A4) and 4-difluoromethoxy-3-ethoxy-benzaldehyde (commercially available) | [M + H]+ 407.3 |
| 69 | 384.52 | N⁵-[1-(4-methoxy-3-propoxy-benzyl)-piperidin-4-yl]-3-methyl-pyridine-2,5-diamine | 3-methyl-N⁵-piperidin-4-yl-pyridine-2,5-diamine dihydrochloride (intermediate A4) and 4-methoxy-3-propoxy-benzaldehyde (intermediate B4) | [M + H]+ 385.3 |
| 70 | 384.52 | N⁵-[1-(3-isopropoxy-4-methoxy-benzyl)-piperidin-4-yl]-3-methyl-pyridine-2,5-diamine | 3-methyl-N⁵-piperidin-4-yl-pyridine-2,5-diamine dihydrochloride (intermediate A4) and 3-isopropoxy-4-methoxy-benzaldehyde (commercially available) | [M + H]+ 385.3 |
| 71 | 382.51 | N⁵-[1-(3-allyloxy-4-methoxy-benzyl)-piperidin-4-yl]-3-methyl-pyridine-2,5-diamine | 3-methyl-N⁵-piperidin-4-yl-pyridine-2,5-diamine dihydrochloride (intermediate A4) and 3-allyloxy-4-methoxy-benzaldehyde (intermediate B5) | [M + H]+ 383.3 |
| 72 | 398.55 | N⁵-[1-(3-isobutoxy-4-methoxy-benzyl)-piperidin-4-yl]-3-methyl-pyridine-2,5-diamine | 3-methyl-N⁵-piperidin-4-yl-pyridine-2,5-diamine dihydrochloride (intermediate A4) and 3-isobutoxy-4-methoxy-benzaldehyde (intermediate B7) | [M + H]+ 399.3 |
| 73 | 410.56 | N⁵-[1-(3-cyclopentyloxy-4-methoxy-benzyl)-piperidin-4-yl]-3-methyl-pyridine-2,5-diamine | 3-methyl-N⁵-piperidin-4-yl-pyridine-2,5-diamine dihydrochloride (intermediate A4) and 3-cyclopentyloxy-4-methoxy-benzaldehyde (commercially available) | [M + H]+ 411.4 |
| 74 | 384.52 | N⁵-[1-(3,5-diethoxy-benzyl)-piperidin-4-yl]-3-methyl-pyridine-2,5-diamine | 3-methyl-N⁵-piperidin-4-yl-pyridine-2,5-diamine dihydrochloride (intermediate A4) and 3,5-diethoxy-benzaldehyde (intermediate B9) | [M + H]+ 385.3 |
| 75 | 412.58 | N⁵-[1-(3,5-diisopropoxy-benzyl)-piperidin-4-yl]-3-methyl-pyridine-2,5-diamine | 3-methyl-N⁵-piperidin-4-yl-pyridine-2,5-diamine dihydrochloride (intermediate A4) and 3,5-diisopropoxy-benzaldehyde (intermediate B10) | [M + H]+ 413.4 |

TABLE 1-continued

| No | MW | Compound Name | Starting Materials | ISP [M + H]+ |
|---|---|---|---|---|
| 76 | 456.59 | 4-[4-(6-amino-5-methyl-pyridin-3-ylamino)-piperidin-1-ylmethyl]-2,6-diethoxy-benzoic acid ethyl ester | 3-methyl-N5-piperidin-4-yl-pyridine-2,5-diamine dihydrochloride (intermediate A4) and 2,6-diethoxy-4-formyl-benzoic acid ethyl ester (intermediate B11) | [M + H]+ 457.4 |
| 77 | 402.51 | N5-[1-(3,5-diethoxy-4-fluoro-benzyl)-piperidin-4-yl]-3-methyl-pyridine-2,5-diamine | 3-methyl-N5-piperidin-4-yl-pyridine-2,5-diamine dihydrochloride (intermediate A4) and 3,5-diethoxy-4-fluoro-benzaldehyde (intermediate B12) | [M + H]+ 403.3 |
| 78 | 449.60 | N5-[1-(3,5-diethoxy-4-pyrrol-1-yl-benzyl)-piperidin-4-yl]-3-methyl-pyridine-2,5-diamine | 3-methyl-N5-piperidin-4-yl-pyridine-2,5-diamine dihydrochloride (intermediate A4) and 3,5-diethoxy-4-pyrrol-1-yl-benzaldehyde (intermediate B15) | [M + H]+ 450.4 |
| 79 | 478.61 | N5-[1-(2,6-diethoxy-4'-fluoro-biphenyl-4-ylmethyl)-piperidin-4-yl]-3-methyl-pyridine-2,5-diamine | 3-methyl-N5-piperidin-4-yl-pyridine-2,5-diamine dihydrochloride (intermediate A4) and 2,6-diethoxy-4'-fluoro-biphenyl-4-carbaldehyde (intermediate B18) | [M + H]+ 479.4 |
| 80 | 416.95 | N-{5-[1-(4-chloro-3-ethoxy-benzyl)-piperidin-4-ylamino]-6-methyl-pyridin-2-yl}-acetamide | N-[6-methyl-5-(piperidin-4-ylamino)-pyridin-2-yl]-acetamide dihydrochloride (intermediate A5) and 4-chloro-3-ethoxy-benzaldehyde (intermediate B2) | [M + H]+ 417.4 |
| 81 | 440.59 | N-{5-[1-(3-isobutoxy-4-methoxy-benzyl)-piperidin-4-ylamino]-6-methyl-pyridin-2-yl}-acetamide | N-[6-methyl-5-(piperidin-4-ylamino)-pyridin-2-yl]-acetamide dihydrochloride (intermediate A5) and 3-isobutoxy-4-methoxy-benzaldehyde (intermediate B7) | [M + H]+ 441.4 |
| 82 | 454.61 | N-{5-[1-(3,5-diisopropoxy-benzyl)-piperidin-4-ylamino]-6-methyl-pyridin-2-yl}-acetamide | N-[6-methyl-5-(piperidin-4-ylamino)-pyridin-2-yl]-acetamide dihydrochloride (intermediate A5) and 3,5-diisopropoxy-benzaldehyde (intermediate B10) | [M + H]+ 441.4 |
| 83 | 444.55 | N-{5-[1-(3,5-diethoxy-4-fluoro-benzyl)-piperidin-4-ylamino]-6-methyl-pyridin-2-yl}-acetamide | N-[6-methyl-5-(piperidin-4-ylamino)-pyridin-2-yl]-acetamide dihydrochloride (intermediate A5) and 3,5-diethoxy-4-fluoro-benzaldehyde (intermediate B12) | [M + H]+ 445.3 |
| 84 | 461.01 | N-{5-[1-(4-chloro-3,5-diethoxy-benzyl)-piperidin-4-ylamino]-6-methyl-pyridin-2-yl}-acetamide | N-[6-methyl-5-(piperidin-4-ylamino)-pyridin-2-yl]-acetamide dihydrochloride (intermediate A5) and 4-chloro-3,5-diethoxy-benzaldehyde (intermediate B13) | [M + H]+ 461.3 |
| 85 | 441.58 | N-{5-[1-(4-amino-3,5-diethoxy-benzyl)-piperidin-4-ylamino]-6-methyl-pyridin-2-yl}-acetamide | N-[6-methyl-5-(piperidin-4-ylamino)-pyridin-2-yl]-acetamide dihydrochloride (intermediate A5) and 4-amino-3,5-diethoxy-benzaldehyde (intermediate B17) | [M + H]+ 442.4 |
| 86 | 491.64 | N-{5-[1-(3,5-diethoxy-4-pyrrol-1-yl-benzyl)-piperidin-4-ylamino]-6-methyl-pyridin-2-yl}-acetamide | N-[6-methyl-5-(piperidin-4-ylamino)-pyridin-2-yl]-acetamide dihydrochloride (intermediate A5) and 3,5-diethoxy-4-pyrrol-1-yl-benzaldehyde (intermediate B15) | [M + H]+ 492.5 |
| 87 | 520.65 | N-{5-[1-(2,6-diethoxy-4'-fluoro-biphenyl-4-ylmethyl)-piperidin-4-ylamino]-6-methyl-pyridin-2-yl}-acetamide | N-[6-methyl-5-(piperidin-4-ylamino)-pyridin-2-yl]-acetamide dihydrochloride (intermediate A5) and 2,6-diethoxy-4'-fluoro-biphenyl-4- | [M + H]+ 521.5 |

TABLE 1-continued

| No | MW | Compound Name | Starting Materials | ISP [M + H]+ |
|---|---|---|---|---|
| | | | carbaldehyde (intermediate B18) | |
| 88 | 379.48 | [1-(3-ethoxy-4-fluoro-benzyl)-piperidin-4-yl]-quinolin-3-yl-amine | piperidin-4-yl-quinolin-3-yl-amine dihydrochloride (intermediate A6) and 3-ethoxy-4-fluoro-benzaldehyde (intermediate B1) | [M + H]+ 380.3 |
| 89 | 395.93 | [1-(4-chloro-3-ethoxy-benzyl)-piperidin-4-yl]-quinolin-3-yl-amine | piperidin-4-yl-quinolin-3-yl-amine dihydrochloride (intermediate A6) and 4-chloro-3-ethoxy-benzaldehyde (intermediate B2) | [M + H]+ 396.1 |
| 90 | 377.49 | 2-ethoxy-4-[4-(quinolin-3-ylamino)-piperidin-1-ylmethyl]-phenol | piperidin-4-yl-quinolin-3-yl-amine dihydrochloride (intermediate A6) and 3-ethoxy-4-hydroxy-benzaldehyde (commercially available) | [M + H]+ 378.3 |
| 91 | 391.51 | [1-(3-ethoxy-4-methoxy-benzyl)-piperidin-4-yl]-quinolin-3-yl-amine | piperidin-4-yl-quinolin-3-yl-amine dihydrochloride (intermediate A6) and 3-ethoxy-4-methoxy-benzaldehyde (commercially available) | [M + H]+ 392.1 |
| 92 | 405.54 | [1-(3,4-diethoxy-benzyl)-piperidin-4-yl]-quinolin-3-yl-amine | piperidin-4-yl-quinolin-3-yl-amine dihydrochloride (intermediate A6) and 3,4-diethoxy-benzaldehyde (commercially available) | [M + H]+ 406.3 |
| 93 | 417.55 | [1-(4-allyloxy-3-ethoxy-benzyl)-piperidin-4-yl]-quinolin-3-yl-amine | piperidin-4-yl-quinolin-3-yl-amine dihydrochloride (intermediate A6) and 4-allyloxy-3-ethoxy-benzaldehyde (commercially available) | [M + H]+ 418.1 |
| 94 | 419.57 | [1-(3-ethoxy-4-isopropoxy-benzyl)-piperidin-4-yl]-quinolin-3-yl-amine | piperidin-4-yl-quinolin-3-yl-amine dihydrochloride (intermediate A6) and 3-ethoxy-4-isopropoxy-benzaldehyde (commercially available) | [M + H]+ 420.1 |
| 95 | 433.60 | [1-(3-ethoxy-4-isobutoxy-benzyl)-piperidin-4-yl]-quinolin-3-yl-amine | piperidin-4-yl-quinolin-3-yl-amine dihydrochloride (intermediate A6) and 3-ethoxy-4-isobutoxy-benzaldehyde (commercially available) | [M + H]+ 434.3 |
| 96 | 447.62 | {1-[3-ethoxy-4-(1-ethyl-propoxy)-benzyl]-piperidin-4-yl}-quinolin-3-yl-amine | piperidin-4-yl-quinolin-3-yl-amine dihydrochloride (intermediate A6) and 3-ethoxy-4-(1-ethyl-propoxy)-benzaldehyde (intermediate B3) | [M + H]+ 448.2 |
| 97 | 445.61 | [1-(4-cyclopentyloxy-3-ethoxy-benzyl)-piperidin-4-yl]-quinolin-3-yl-amine | piperidin-4-yl-quinolin-3-yl-amine dihydrochloride (intermediate A6) and 4-cyclopentyloxy-3-ethoxy-benzaldehyde (commercially available) | [M + H]+ 446.3 |
| 98 | 467.61 | [1-(4-benzyloxy-3-ethoxy-benzyl)-piperidin-4-yl]-quinolin-3-yl-amine | piperidin-4-yl-quinolin-3-yl-amine dihydrochloride (intermediate A6) and 4-benzyloxy-3-ethoxy-benzaldehyde (commercially available) | [M + H]+ 468.2 |
| 99 | 427.49 | [1-(4-difluoromethoxy-3-ethoxy-benzyl)-piperidin-4-yl]-quinolin-3-yl-amine | piperidin-4-yl-quinolin-3-yl-amine dihydrochloride (intermediate A6) and 4-difluoromethoxy-3-ethoxy-benzaldehyde (commercially available) | [M + H]+ 428.3 |
| 100 | 405.54 | [1-(4-methoxy-3-propoxy-benzyl)-piperidin-4-yl]-quinolin-3-yl-amine | piperidin-4-yl-quinolin-3-yl-amine dihydrochloride (intermediate A6) and 4-methoxy-3-propoxy-benzaldehyde (intermediate B4) | [M + H]+ 406.3 |

TABLE 1-continued

| No | MW | Compound Name | Starting Materials | ISP [M + H]+ |
|---|---|---|---|---|
| 101 | 405.54 | [1-(3-isopropoxy-4-methoxy-benzyl)-piperidin-4-yl]-quinolin-3-yl-amine | piperidin-4-yl-quinolin-3-yl-amine dihydrochloride (intermediate A6) and 3-isopropoxy-4-methoxy-benzaldehyde (commercially available) | [M + H]+ 406.5 |
| 102 | 409.50 | {1-[3-(2-fluoro-ethoxy)-4-methoxy-benzyl]-piperidin-4-yl}-quinolin-3-yl-amine | piperidin-4-yl-quinolin-3-yl-amine dihydrochloride (intermediate A6) and 3-(2-fluoro-ethoxy)-4-methoxy-benzaldehyde (intermediate B16) | [M + H]+ 410.3 |
| 103 | 403.53 | [1-(3-allyloxy-4-methoxy-benzyl)-piperidin-4-yl]-quinolin-3-yl-amine | piperidin-4-yl-quinolin-3-yl-amine dihydrochloride (intermediate A6) and 3-allyloxy-4-methoxy-benzaldehyde (intermediate B5) | [M + H]+ 404.2 |
| 104 | 401.51 | [1-(4-methoxy-3-prop-2-ynyloxy-benzyl)-piperidin-4-yl]-quinolin-3-yl-amine | piperidin-4-yl-quinolin-3-yl-amine dihydrochloride (intermediate A6) and 4-methoxy-3-prop-2-ynyloxy-benzaldehyde (commercially available) | [M + H]+ 402.3 |
| 105 | 419.57 | [1-(3-butoxy-4-methoxy-benzyl)-piperidin-4-yl]-quinolin-3-yl-amine | piperidin-4-yl-quinolin-3-yl-amine dihydrochloride (intermediate A6) and 3-butoxy-4-methoxy-benzaldehyde (intermediate B6) | [M + H]+ 420.1 |
| 106 | 419.57 | [1-(3-isobutoxy-4-methoxy-benzyl)-piperidin-4-yl]-quinolin-3-yl-amine | piperidin-4-yl-quinolin-3-yl-amine dihydrochloride (intermediate A6) and 3-isobutoxy-4-methoxy-benzaldehyde (intermediate B7) | [M + H]+ 420.2 |
| 107 | 431.58 | [1-(3-cyclopentyloxy-4-methoxy-benzyl)-piperidin-4-yl]-quinolin-3-yl-amine | piperidin-4-yl-quinolin-3-yl-amine dihydrochloride (intermediate A6) and 3-cyclopentyloxy-4-methoxy-benzaldehyde (commercially available) | [M + H]+ 432.4 |
| 108 | 439.53 | 2-{2-ethoxy-5-fluoro-4-[4-(quinolin-3-ylamino)-piperidin-1-ylmethyl]-phenoxy}-ethanol | piperidin-4-yl-quinolin-3-yl-amine dihydrochloride (intermediate A6) and 5-ethoxy-2-fluoro-4-(2-hydroxy-ethoxy)-benzaldehyde (intermediate B19) | [M + H]+ 440.4 |
| 109 | 443.59 | [1-(8-ethoxy-2,2-dimethyl-2H-chromen-6-ylmethyl)-piperidin-4-yl]-quinolin-3-yl-amine | piperidin-4-yl-quinolin-3-yl-amine dihydrochloride (intermediate A6) and 8-ethoxy-2,2-dimethyl-2H-chromene-6-carbaldehyde (intermediate B8) | [M + H]+ 444.3 |
| 110 | 405.54 | [1-(3,5-diethoxy-benzyl)-piperidin-4-yl]-quinolin-3-yl-amine | piperidin-4-yl-quinolin-3-yl-amine dihydrochloride (intermediate A6) and 3,5-diethoxy-benzaldehyde (intermediate B9) | [M + H]+ 406.3 |
| 111 | 433.60 | [1-(3,5-diisopropoxy-benzyl)-piperidin-4-yl]-quinolin-3-yl-amine | piperidin-4-yl-quinolin-3-yl-amine dihydrochloride (intermediate A6) and 3,5-diisopropoxy-benzaldehyde (intermediate B10) | [M + H]+ 434.3 |
| 112 | 477.60 | 2,6-diethoxy-4-[4-(quinolin-3-ylamino)-piperidin-1-ylmethyl]-benzoic acid ethyl ester | piperidin-4-yl-quinolin-3-yl-amine dihydrochloride (intermediate A6) and 2,6-diethoxy-4-formyl-benzoic acid ethyl ester (intermediate B11) | [M + H]+ 478.2 |
| 113 | 423.53 | [1-(3,5-diethoxy-4-fluoro-benzyl)-piperidin-4-yl]-quinolin-3-yl-amine | piperidin-4-yl-quinolin-3-yl-amine dihydrochloride (intermediate A6) and 3,5-diethoxy-4-fluoro-benzaldehyde (intermediate B12) | [M + H]+ 424.2 |

TABLE 1-continued

| No | MW | Compound Name | Starting Materials | ISP [M + H]+ |
|---|---|---|---|---|
| 114 | 439.99 | [1-(4-chloro-3,5-diethoxy-benzyl)-piperidin-4-yl]-quinolin-3-yl-amine | piperidin-4-yl-quinolin-3-yl-amine dihydrochloride (intermediate A6) and 4-chloro-3,5-diethoxy-benzaldehyde (intermediate B13) | [M + H]+ 440.3 |
| 115 | 484.44 | [1-(4-bromo-3,5-diethoxy-benzyl)-piperidin-4-yl]-quinolin-3-yl-amine | piperidin-4-yl-quinolin-3-yl-amine dihydrochloride (intermediate A6) and 4-bromo-3,5-diethoxy-benzaldehyde (intermediate B14) | [M + H]+ 486.2 |
| 116 | 420.56 | [1-(4-amino-3,5-diethoxy-benzyl)-piperidin-4-yl]-quinolin-3-yl-amine | piperidin-4-yl-quinolin-3-yl-amine dihydrochloride (intermediate A6) and 4-amino-3,5-diethoxy-benzaldehyde (intermediate B17) | [M + H]+ 421.1 |
| 117 | 470.62 | [1-(3,5-diethoxy-4-pyrrol-1-yl-benzyl)-piperidin-4-yl]-quinolin-3-yl-amine | piperidin-4-yl-quinolin-3-yl-amine dihydrochloride (intermediate A6) and 3,5-diethoxy-4-pyrrol-1-yl-benzaldehyde (intermediate B15) | [M + H]+ 471.1 |
| 118 | 499.63 | [1-(2,6-diethoxy-4'-fluoro-biphenyl-4-ylmethyl)-piperidin-4-yl]-quinolin-3-yl-amine | piperidin-4-yl-quinolin-3-yl-amine dihydrochloride (intermediate A6) and 2,6-diethoxy-4'-fluoro-biphenyl-4-carbaldehyde (intermediate B18) | [M + H]+ 500.2 |
| 119 | 343.45 | [1-(3-ethoxy-4-fluoro-benzyl)-piperidin-4-yl]-(2-methyl-pyridin-4-yl)-amine | (2-methyl-pyridin-4-yl)-piperidin-4-yl-amine dihydrochloride (intermediate A7) and 3-ethoxy-4-fluoro-benzaldehyde (intermediate B1) | [M + H]+ 344.3 |
| 120 | 359.90 | [1-(4-chloro-3-ethoxy-benzyl)-piperidin-4-yl]-(2-methyl-pyridin-4-yl)-amine | (2-methyl-pyridin-4-yl)-piperidin-4-yl-amine dihydrochloride (intermediate A7) and 4-chloro-3-ethoxy-benzaldehyde (intermediate B2) | [M + H]+ 360.3 |
| 121 | 355.48 | [1-(3-ethoxy-4-methoxy-benzyl)-piperidin-4-yl]-(2-methyl-pyridin-4-yl)-amine | (2-methyl-pyridin-4-yl)-piperidin-4-yl-amine dihydrochloride (intermediate A7) and 3-ethoxy-4-methoxy-benzaldehyde (commercially available) | [M + H]+ 356.2 |
| 122 | 397.56 | [1-(3-ethoxy-4-isobutoxy-benzyl)-piperidin-4-yl]-(2-methyl-pyridin-4-yl)-amine | (2-methyl-pyridin-4-yl)-piperidin-4-yl-amine dihydrochloride (intermediate A7) and 3-ethoxy-4-isobutoxy-benzaldehyde (commercially available) | [M + H]+ 398.4 |
| 123 | 409.57 | [1-(4-cyclopentyloxy-3-ethoxy-benzyl)-piperidin-4-yl]-(2-methyl-pyridin-4-yl)-amine | (2-methyl-pyridin-4-yl)-piperidin-4-yl-amine dihydrochloride (intermediate A7) and 4-cyclopentyloxy-3-ethoxy-benzaldehyde (commercially available) | [M + H]+ 410.3 |
| 124 | 431.58 | [1-(4-benzyloxy-3-ethoxy-benzyl)-piperidin-4-yl]-(2-methyl-pyridin-4-yl)-amine | (2-methyl-pyridin-4-yl)-piperidin-4-yl-amine dihydrochloride (intermediate A7) and 4-benzyloxy-3-ethoxy-benzaldehyde (commercially available) | [M + H]+ 432.3 |
| 125 | 391.46 | [1-(4-difluoromethoxy-3-ethoxy-benzyl)-piperidin-4-yl]-(2-methyl-pyridin-4-yl)-amine | (2-methyl-pyridin-4-yl)-piperidin-4-yl-amine dihydrochloride (intermediate A7) and 4-difluoromethoxy-3-ethoxy-benzaldehyde (commercially available) | [M + H]+ 392.1 |
| 126 | 369.51 | [1-(4-methoxy-3-propoxy-benzyl)-piperidin-4-yl]-(2-methyl-pyridin-4-yl)-amine | (2-methyl-pyridin-4-yl)-piperidin-4-yl-amine dihydrochloride (intermediate A7) and 4-methoxy-3- | [M + H]+ 370.2 |

TABLE 1-continued

| No | MW | Compound Name | Starting Materials | ISP [M + H]+ |
|---|---|---|---|---|
| | | amine | propoxy-benzaldehyde (intermediate B4) | |
| 127 | 383.54 | [1-(3-isobutoxy-4-methoxy-benzyl)-piperidin-4-yl]-(2-methyl-pyridin-4-yl)-amine | (2-methyl-pyridin-4-yl)-piperidin-4-yl-amine dihydrochloride (intermediate A7) and 3-isobutoxy-4-methoxy-benzaldehyde (intermediate B7) | [M + H]+ 384.3 |
| 128 | 395.55 | [1-(3-cyclopentyloxy-4-methoxy-benzyl)-piperidin-4-yl]-(2-methyl-pyridin-4-yl)-amine | (2-methyl-pyridin-4-yl)-piperidin-4-yl-amine dihydrochloride (intermediate A7) and 3-cyclopentyloxy-4-methoxy-benzaldehyde (commercially available) | [M + H]+ 396.3 |
| 129 | 407.56 | [1-(8-ethoxy-2,2-dimethyl-2H-chromen-6-ylmethyl)-piperidin-4-yl]-(2-methyl-pyridin-4-yl)-amine | (2-methyl-pyridin-4-yl)-piperidin-4-yl-amine dihydrochloride (intermediate A7) and 8-ethoxy-2,2-dimethyl-2H-chromene-6-carbaldehyde (intermediate B8) | [M + H]+ 408.5 |
| 130 | 369.51 | [1-(3,5-diethoxy-benzyl)-piperidin-4-yl]-(2-methyl-pyridin-4-yl)-amine | (2-methyl-pyridin-4-yl)-piperidin-4-yl-amine dihydrochloride (intermediate A7) and 3,5-diethoxy-benzaldehyde (intermediate B9) | [M + H]+ 370.3 |
| 131 | 397.56 | [1-(3,5-diisopropoxy-benzyl)-piperidin-4-yl]-(2-methyl-pyridin-4-yl)-amine | (2-methyl-pyridin-4-yl)-piperidin-4-yl-amine dihydrochloride (intermediate A7) and 3,5-diisopropoxy-benzaldehyde (intermediate B10) | [M + H]+ 398.4 |
| 132 | 441.57 | 2,6-diethoxy-4-[4-(2-methyl-pyridin-4-ylamino)-piperidin-1-ylmethyl]-benzoic acid ethyl ester | (2-methyl-pyridin-4-yl)-piperidin-4-yl-amine dihydrochloride (intermediate A7) and 2,6-diethoxy-4-formyl-benzoic acid ethyl ester (intermediate B11) | [M + H]+ 442.5 |
| 133 | 387.50 | [1-(3,5-diethoxy-4-fluoro-benzyl)-piperidin-4-yl]-(2-methyl-pyridin-4-yl)-amine | (2-methyl-pyridin-4-yl)-piperidin-4-yl-amine dihydrochloride (intermediate A7) and 3,5-diethoxy-4-fluoro-benzaldehyde (intermediate B12) | [M + H]+ 388.2 |
| 134 | 403.95 | [1-(4-chloro-3,5-diethoxy-benzyl)-piperidin-4-yl]-(2-methyl-pyridin-4-yl)-amine | (2-methyl-pyridin-4-yl)-piperidin-4-yl-amine dihydrochloride (intermediate A7) and 4-chloro-3,5-diethoxy-benzaldehyde (intermediate B13) | [M + H]+ 404.4 |
| 135 | 448.41 | [1-(4-bromo-3,5-diethoxy-benzyl)-piperidin-4-yl]-(2-methyl-pyridin-4-yl)-amine | (2-methyl-pyridin-4-yl)-piperidin-4-yl-amine dihydrochloride (intermediate A7) and 4-bromo-3,5-diethoxy-benzaldehyde (intermediate B14) | [M + H]+ 450.3 |
| 136 | 384.52 | [1-(4-amino-3,5-diethoxy-benzyl)-piperidin-4-yl]-(2-methyl-pyridin-4-yl)-amine | (2-methyl-pyridin-4-yl)-piperidin-4-yl-amine dihydrochloride (intermediate A7) and 4-amino-3,5-diethoxy-benzaldehyde (intermediate B17) | [M + H]+ 385.3 |
| 137 | 434.58 | [1-(3,5-diethoxy-4-pyrrol-1-yl-benzyl)-piperidin-4-yl]-(2-methyl-pyridin-4-yl)-amine | (2-methyl-pyridin-4-yl)-piperidin-4-yl-amine dihydrochloride (intermediate A7) and 3,5-diethoxy-4-pyrrol-1-yl-benzaldehyde (intermediate B15) | [M + H]+ 435.5 |
| 138 | 463.60 | [1-(2,6-diethoxy-4'-fluoro-biphenyl-4-ylmethyl)-piperidin-4-yl]-(2-methyl-pyridin-4-yl)-amine | (2-methyl-pyridin-4-yl)-piperidin-4-yl-amine dihydrochloride (intermediate A7) and 2,6-diethoxy-4'-fluoro-biphenyl-4-carbaldehyde (intermediate B18) | [M + H]+ 464.4 |

TABLE 1-continued

| No | MW | Compound Name | Starting Materials | ISP [M + H]+ |
|---|---|---|---|---|
| 139 | 636.86 | [1-(4-chloro-3-ethoxy-benzyl)-piperidin-4-yl]-(3-fluoro-pyridin-4-yl)-amine | (3-fluoro-pyridin-4-yl)-piperidin-4-yl-amine dihydrochloride (intermediate A8) and 4-chloro-3-ethoxy-benzaldehyde (intermediate B2) | [M + H]+ 364.2 |
| 140 | 407.92 | [1-(4-chloro-3,5-diethoxy-benzyl)-piperidin-4-yl]-(3-fluoro-pyridin-4-yl)-amine | (3-fluoro-pyridin-4-yl)-piperidin-4-yl-amine dihydrochloride (intermediate A8) and 4-chloro-3,5-diethoxy-benzaldehyde (intermediate B13) | [M + H]+ 408.4 |
| 141 | 388.49 | [1-(4-amino-3,5-diethoxy-benzyl)-piperidin-4-yl]-(3-fluoro-pyridin-4-yl)-amine | (3-fluoro-pyridin-4-yl)-piperidin-4-yl-amine dihydrochloride (intermediate A8) and 4-amino-3,5-diethoxy-benzaldehyde (intermediate B17) | [M + H]+ 389.1 |
| 142 | 467.56 | [1-(2,6-diethoxy-4'-fluoro-biphenyl-4-ylmethyl)-piperidin-4-yl]-(3-fluoro-pyridin-4-yl)-amine | (3-fluoro-pyridin-4-yl)-piperidin-4-yl-amine dihydrochloride (intermediate A8) and 2,6-diethoxy-4'-fluoro-biphenyl-4-carbaldehyde (intermediate B18) | [M + H]+ 468.3 |
| 143 | 379.48 | [1-(3-ethoxy-4-fluoro-benzyl)-piperidin-4-yl]-quinolin-4-yl-amine | piperidin-4-yl-quinolin-4-yl-amine dihydrochloride (intermediate A9) and 3-ethoxy-4-fluoro-benzaldehyde (intermediate B1) | [M + H]+ 380.3 |
| 144 | 395.93 | [1-(4-chloro-3-ethoxy-benzyl)-piperidin-4-yl]-quinolin-4-yl-amine | piperidin-4-yl-quinolin-4-yl-amine dihydrochloride (intermediate A9) and 4-chloro-3-ethoxy-benzaldehyde (intermediate B2) | [M + H]+ 396.1 |
| 145 | 377.49 | 2-ethoxy-4-[4-(quinolin-4-ylamino)-piperidin-1-ylmethyl]-phenol | piperidin-4-yl-quinolin-4-yl-amine dihydrochloride (intermediate A9) and 3-ethoxy-4-hydroxy-benzaldehyde (commercially available) | [M + H]+ 378.2 |
| 146 | 391.51 | [1-(3-ethoxy-4-methoxy-benzyl)-piperidin-4-yl]-quinolin-4-yl-amine | piperidin-4-yl-quinolin-4-yl-amine dihydrochloride (intermediate A9) and 3-ethoxy-4-methoxy-benzaldehyde (commercially available) | [M + H]+ 392.0 |
| 147 | 405.54 | [1-(3,4-diethoxy-benzyl)-piperidin-4-yl]-quinolin-4-yl-amine | piperidin-4-yl-quinolin-4-yl-amine dihydrochloride (intermediate A9) and 3,4-diethoxy-benzaldehyde (commercially available) | [M + H]+ 406.3 |
| 148 | 417.55 | [1-(4-allyloxy-3-ethoxy-benzyl)-piperidin-4-yl]-quinolin-4-yl-amine | piperidin-4-yl-quinolin-4-yl-amine dihydrochloride (intermediate A9) and 4-allyloxy-3-ethoxy-benzaldehyde (commercially available) | [M + H]+ 418.1 |
| 149 | 419.57 | [1-(3-ethoxy-4-isopropoxy-benzyl)-piperidin-4-yl]-quinolin-4-yl-amine | piperidin-4-yl-quinolin-4-yl-amine dihydrochloride (intermediate A9) and 3-ethoxy-4-isopropoxy-benzaldehyde (commercially available) | [M + H]+ 420.1 |
| 150 | 433.60 | [1-(3-ethoxy-4-isobutoxy-benzyl)-piperidin-4-yl]-quinolin-4-yl-amine | piperidin-4-yl-quinolin-4-yl-amine dihydrochloride (intermediate A9) and 3-ethoxy-4-isobutoxy-benzaldehyde (commercially available) | [M + H]+ 434.3 |
| 151 | 447.62 | {1-[3-ethoxy-4-(1-ethyl-propoxy)-benzyl]-piperidin-4-yl}-quinolin-4-yl-amine | piperidin-4-yl-quinolin-4-yl-amine dihydrochloride (intermediate A9) and 3-ethoxy-4-(1-ethyl-propoxy)-benzaldehyde (intermediate B3) | [M + H]+ 448.2 |

TABLE 1-continued

| No | MW | Compound Name | Starting Materials | ISP [M + H]+ |
|---|---|---|---|---|
| 152 | 445.61 | [1-(4-cyclopentyloxy-3-ethoxy-benzyl)-piperidin-4-yl]-quinolin-4-yl-amine | piperidin-4-yl-quinolin-4-yl-amine dihydrochloride (intermediate A9) and 4-cyclopentyloxy-3-ethoxy-benzaldehyde (commercially available) | [M + H]+ 446.1 |
| 153 | 467.61 | [1-(4-benzyloxy-3-ethoxy-benzyl)-piperidin-4-yl]-quinolin-4-yl-amine | piperidin-4-yl-quinolin-4-yl-amine dihydrochloride (intermediate A9) and 4-benzyloxy-3-ethoxy-benzaldehyde (commercially available) | [M + H]+ 468.2 |
| 154 | 427.49 | [1-(4-difluoromethoxy-3-ethoxy-benzyl)-piperidin-4-yl]-quinolin-4-yl-amine | piperidin-4-yl-quinolin-4-yl-amine dihydrochloride (intermediate A9) and 4-difluoromethoxy-3-ethoxy-benzaldehyde (commercially available) | [M + H]+ 428.3 |
| 155 | 405.54 | [1-(4-methoxy-3-propoxy-benzyl)-piperidin-4-yl]-quinolin-4-yl-amine | piperidin-4-yl-quinolin-4-yl-amine dihydrochloride (intermediate A9) and 4-methoxy-3-propoxy-benzaldehyde (intermediate B4) | [M + H]+ 406.3 |
| 156 | 405.54 | [1-(3-isopropoxy-4-methoxy-benzyl)-piperidin-4-yl]-quinolin-4-yl-amine | piperidin-4-yl-quinolin-4-yl-amine dihydrochloride (intermediate A9) and 3-isopropoxy-4-methoxy-benzaldehyde (commercially available) | [M + H]+ 406.3 |
| 157 | 409.50 | {1-[3-(2-fluoro-ethoxy)-4-methoxy-benzyl]-piperidin-4-yl}-quinolin-4-yl-amine | piperidin-4-yl-quinolin-4-yl-amine dihydrochloride (intermediate A9) and 3-(2-fluoro-ethoxy)-4-methoxy-benzaldehyde (intermediate B16) | [M + H]+ 410.3 |
| 158 | 403.53 | [1-(3-allyloxy-4-methoxy-benzyl)-piperidin-4-yl]-quinolin-4-yl-amine | piperidin-4-yl-quinolin-4-yl-amine dihydrochloride (intermediate A9) and 3-allyloxy-4-methoxy-benzaldehyde (intermediate B5) | [M + H]+ 404.3 |
| 159 | 401.51 | [1-(4-methoxy-3-prop-2-ynyloxy-benzyl)-piperidin-4-yl]-quinolin-4-yl-amine | piperidin-4-yl-quinolin-4-yl-amine dihydrochloride (intermediate A9) and 4-methoxy-3-prop-2-ynyloxy-benzaldehyde (commercially available) | [M + H]+ 402.3 |
| 160 | 419.57 | [1-(3-butoxy-4-methoxy-benzyl)-piperidin-4-yl]-quinolin-4-yl-amine | piperidin-4-yl-quinolin-4-yl-amine dihydrochloride (intermediate A9) and 3-butoxy-4-methoxy-benzaldehyde (intermediate B6) | [M + H]+ 420.1 |
| 161 | 419.57 | [1-(3-isobutoxy-4-methoxy-benzyl)-piperidin-4-yl]-quinolin-4-yl-amine | piperidin-4-yl-quinolin-4-yl-amine dihydrochloride (intermediate A9) and 3-isobutoxy-4-methoxy-benzaldehyde (intermediate B7) | [M + H]+ 420.1 |
| 162 | 431.58 | [1-(3-cyclopentyloxy-4-methoxy-benzyl)-piperidin-4-yl]-quinolin-4-yl-amine | piperidin-4-yl-quinolin-4-yl-amine dihydrochloride (intermediate A9) and 3-cyclopentyloxy-4-methoxy-benzaldehyde (commercially available) | [M + H]+ 432.2 |
| 163 | 443.59 | [1-(8-ethoxy-2,2-dimethyl-2H-chromen-6-ylmethyl)-piperidin-4-yl]-quinolin-4-yl-amine | piperidin-4-yl-quinolin-4-yl-amine dihydrochloride (intermediate A9) and 8-ethoxy-2,2-dimethyl-2H-chromene-6-carbaldehyde (intermediate B8) | [M + H]+ 444.2 |
| 164 | 405.54 | [1-(3,5-diethoxy-benzyl)-piperidin-4-yl]-quinolin-4-yl-amine | piperidin-4-yl-quinolin-4-yl-amine dihydrochloride (intermediate A9) and 3,5-diethoxy-benzaldehyde (intermediate B9) | [M + H]+ 406.3 |

TABLE 1-continued

| No | MW | Compound Name | Starting Materials | ISP [M + H]+ |
|---|---|---|---|---|
| 165 | 433.60 | [1-(3,5-diisopropoxy-benzyl)-piperidin-4-yl]-quinolin-4-yl-amine | piperidin-4-yl-quinolin-4-yl-amine dihydrochloride (intermediate A9) and 3,5-diisopropoxy-benzaldehyde (intermediate B10) | [M + H]+ 434.3 |
| 166 | 477.60 | 2,6-diethoxy-4-[4-(quinolin-4-ylamino)-piperidin-1-ylmethyl]-benzoic acid ethyl ester | piperidin-4-yl-quinolin-4-yl-amine dihydrochloride (intermediate A9) and 2,6-diethoxy-4-formyl-benzoic acid ethyl ester (intermediate B11) | [M + H]+ 478.2 |
| 167 | 423.53 | [1-(3,5-diethoxy-4-fluoro-benzyl)-piperidin-4-yl]-quinolin-4-yl-amine | piperidin-4-yl-quinolin-4-yl-amine dihydrochloride (intermediate A9) and 3,5-diethoxy-4-fluoro-benzaldehyde (intermediate B12) | [M + H]+ 424.2 |
| 168 | 439.99 | [1-(4-chloro-3,5-diethoxy-benzyl)-piperidin-4-yl]-quinolin-4-yl-amine | piperidin-4-yl-quinolin-4-yl-amine dihydrochloride (intermediate A9) and 4-chloro-3,5-diethoxy-benzaldehyde (intermediate B13) | [M + H]+ 440.3 |
| 169 | 484.44 | [1-(4-bromo-3,5-diethoxy-benzyl)-piperidin-4-yl]-quinolin-4-yl-amine | piperidin-4-yl-quinolin-4-yl-amine dihydrochloride (intermediate A9) and 4-bromo-3,5-diethoxy-benzaldehyde (intermediate B14) | [M + H]+ 486.2 |
| 170 | 420.56 | [1-(4-amino-3,5-diethoxy-benzyl)-piperidin-4-yl]-quinolin-4-yl-amine | piperidin-4-yl-quinolin-4-yl-amine dihydrochloride (intermediate A9) and 4-amino-3,5-diethoxy-benzaldehyde (intermediate B17) | [M + H]+ 421.2 |
| 171 | 470.62 | [1-(3,5-diethoxy-4-pyrrol-1-yl-benzyl)-piperidin-4-yl]-quinolin-4-yl-amine | piperidin-4-yl-quinolin-4-yl-amine dihydrochloride (intermediate A9) and 3,5-diethoxy-4-pyrrol-1-yl-benzaldehyde (intermediate B15) | [M + H]+ 471.1 |
| 172 | 499.63 | [1-(2,6-diethoxy-4'-fluoro-biphenyl-4-ylmethyl)-piperidin-4-yl]-quinolin-4-yl-amine | piperidin-4-yl-quinolin-4-yl-amine dihydrochloride (intermediate A9) and 2,6-diethoxy-4'-fluoro-biphenyl-4-carbaldehyde (intermediate B18) | [M + H]+ 500.2 |
| 173 | 413.92 | (7-chloro-quinolin-4-yl)-[1-(3-ethoxy-4-fluoro-benzyl)-piperidin-4-yl]-amine | (7-chloro-quinolin-4-yl)-piperidin-4-yl-amine dihydrochloride (intermediate A10) and 3-ethoxy-4-fluoro-benzaldehyde (intermediate B1) | [M + H]+ 414.3 |
| 174 | 430.38 | [1-(4-chloro-3-ethoxy-benzyl)-piperidin-4-yl]-(7-chloro-quinolin-4-yl)-amine | (7-chloro-quinolin-4-yl)-piperidin-4-yl-amine dihydrochloride (intermediate A10) and 4-chloro-3-ethoxy-benzaldehyde (intermediate B2) | [M + H]+ 430.3 |
| 175 | 411.93 | 4-[4-(7-chloro-quinolin-4-ylamino)-piperidin-1-ylmethyl]-2-ethoxy-phenol | (7-chloro-quinolin-4-yl)-piperidin-4-yl-amine dihydrochloride (intermediate A10) and 3-ethoxy-4-hydroxy-benzaldehyde (commercially available) | [M + H]+ 412.0 |
| 176 | 425.96 | (7-chloro-quinolin-4-yl)-[1-(3-ethoxy-4-methoxy-benzyl)-piperidin-4-yl]-amine | (7-chloro-quinolin-4-yl)-piperidin-4-yl-amine dihydrochloride (intermediate A10) and 3-ethoxy-4-methoxy-benzaldehyde (commercially available) | [M + H]+ 426.1 |
| 177 | 452.00 | [1-(4-allyloxy-3-ethoxy-benzyl)-piperidin-4-yl]-(7-chloro-quinolin-4-yl)-amine | (7-chloro-quinolin-4-yl)-piperidin-4-yl-amine dihydrochloride (intermediate A10) and 4-allyloxy-3-ethoxy- | [M + H]+ 452.1 |

TABLE 1-continued

| No | MW | Compound Name | Starting Materials | ISP [M + H]+ |
|---|---|---|---|---|
| 178 | 454.01 | (7-chloro-quinolin-4-yl)-[1-(3-ethoxy-4-isopropoxy-benzyl)-piperidin-4-yl]-amine | (7-chloro-quinolin-4-yl)-piperidin-4-yl-amine dihydrochloride (intermediate A10) and 3-ethoxy-4-isopropoxy-benzaldehyde (commercially available) | [M + H]+ 454.3 |
| 179 | 468.04 | (7-chloro-quinolin-4-yl)-[1-(3-ethoxy-4-isobutoxy-benzyl)-piperidin-4-yl]-amine | (7-chloro-quinolin-4-yl)-piperidin-4-yl-amine dihydrochloride (intermediate A10) and 3-ethoxy-4-isobutoxy-benzaldehyde (commercially available) | [M + H]+ 468.2 |
| 180 | 482.07 | (7-chloro-quinolin-4-yl)-{1-[3-ethoxy-4-(1-ethyl-propoxy)-benzyl]-piperidin-4-yl}-amine | (7-chloro-quinolin-4-yl)-piperidin-4-yl-amine dihydrochloride (intermediate A10) and 3-ethoxy-4-(1-ethyl-propoxy)-benzaldehyde (intermediate B3) | [M + H]+ 482.3 |
| 181 | 480.05 | (7-chloro-quinolin-4-yl)-[1-(4-cyclopentyloxy-3-ethoxy-benzyl)-piperidin-4-yl]-amine | (7-chloro-quinolin-4-yl)-piperidin-4-yl-amine dihydrochloride (intermediate A10) and 4-cyclopentyloxy-3-ethoxy-benzaldehyde (commercially available) | [M + H]+ 480.2 |
| 182 | 502.06 | [1-(4-benzyloxy-3-ethoxy-benzyl)-piperidin-4-yl]-(7-chloro-quinolin-4-yl)-amine | (7-chloro-quinolin-4-yl)-piperidin-4-yl-amine dihydrochloride (intermediate A10) and 4-benzyloxy-3-ethoxy-benzaldehyde (commercially available) | [M + H]+ 502.1 |
| 183 | 461.94 | (7-chloro-quinolin-4-yl)-[1-(4-difluoromethoxy-3-ethoxy-benzyl)-piperidin-4-yl]-amine | (7-chloro-quinolin-4-yl)-piperidin-4-yl-amine dihydrochloride (intermediate A10) and 4-difluoromethoxy-3-ethoxy-benzaldehyde (commercially available) | [M + H]+ 462.3 |
| 184 | 439.99 | (7-chloro-quinolin-4-yl)-[1-(4-methoxy-3-propoxy-benzyl)-piperidin-4-yl]-amine | (7-chloro-quinolin-4-yl)-piperidin-4-yl-amine dihydrochloride (intermediate A10) and 4-methoxy-3-propoxy-benzaldehyde (intermediate B4) | [M + H]+ 440.3 |
| 185 | 439.99 | (7-chloro-quinolin-4-yl)-[1-(3-isopropoxy-4-methoxy-benzyl)-piperidin-4-yl]-amine | (7-chloro-quinolin-4-yl)-piperidin-4-yl-amine dihydrochloride (intermediate A10) and 3-isopropoxy-4-methoxy-benzaldehyde (commercially available) | [M + H]+ 440.3 |
| 186 | 443.95 | (7-chloro-quinolin-4-yl)-{1-[3-(2-fluoro-ethoxy)-4-methoxy-benzyl]-piperidin-4-yl}-amine | (7-chloro-quinolin-4-yl)-piperidin-4-yl-amine dihydrochloride (intermediate A10) and 3-(2-fluoro-ethoxy)-4-methoxy-benzaldehyde (intermediate B16) | [M + H]+ 444.1 |
| 187 | 437.97 | [1-(3-allyloxy-4-methoxy-benzyl)-piperidin-4-yl]-(7-chloro-quinolin-4-yl)-amine | (7-chloro-quinolin-4-yl)-piperidin-4-yl-amine dihydrochloride (intermediate A10) and 3-allyloxy-4-methoxy-benzaldehyde (intermediate B5) | [M + H]+ 438.1 |
| 188 | 435.95 | (7-chloro-quinolin-4-yl)-[1-(4-methoxy-3-prop-2-ynyloxy-benzyl)-piperidin-4-yl]-amine | (7-chloro-quinolin-4-yl)-piperidin-4-yl-amine dihydrochloride (intermediate A10) and 4-methoxy-3-prop-2-ynyloxy-benzaldehyde (commercially available) | [M + H]+ 436.1 |
| 189 | 454.01 | (7-chloro-quinolin-4-yl)-[1-(3-isobutoxy-4-methoxy-benzyl)-piperidin-4-yl]-amine | (7-chloro-quinolin-4-yl)-piperidin-4-yl-amine dihydrochloride (intermediate A10) and 3-isobutoxy-4-methoxy-benzaldehyde (intermediate B7) | [M + H]+ 454.3 |
| 190 | 466.02 | (7-chloro-quinolin-4-yl)-[1-(3-cyclopentyloxy-4-methoxy-benzyl)- | (7-chloro-quinolin-4-yl)-piperidin-4-yl-amine dihydrochloride (intermediate | [M + H]+ 466.2 |

TABLE 1-continued

| No | MW | Compound Name | Starting Materials | ISP [M + H]+ |
|---|---|---|---|---|
| | | piperidin-4-yl]-amine | A10) and 3-cyclopentyloxy-4-methoxy-benzaldehyde (commercially available) | |
| 191 | 473.98 | 2-{4-[4-(7-chloro-quinolin-4-ylamino)-piperidin-1-ylmethyl]-2-ethoxy-5-fluoro-phenoxy}-ethanol | (7-chloro-quinolin-4-yl)-piperidin-4-yl-amine dihydrochloride (intermediate A10) and 5-ethoxy-2-fluoro-4-(2-hydroxy-ethoxy)-benzaldehyde (intermediate B19) | [M + H]+ 474.0 |
| 192 | 478.04 | (7-chloro-quinolin-4-yl)-[1-(8-ethoxy-2,2-dimethyl-2H-chromen-6-ylmethyl)-piperidin-4-yl]-amine | (7-chloro-quinolin-4-yl)-piperidin-4-yl-amine dihydrochloride (intermediate A10) and 8-ethoxy-2,2-dimethyl-2H-chromene-6-carbaldehyde (intermediate B8) | [M + H]+ 478.1 |
| 193 | 439.99 | (7-chloro-quinolin-4-yl)-[1-(3,5-diethoxy-benzyl)-piperidin-4-yl]-amine | (7-chloro-quinolin-4-yl)-piperidin-4-yl-amine dihydrochloride (intermediate A10) and 3,5-diethoxy-benzaldehyde (intermediate B9) | [M + H]+ 440.3 |
| 194 | 468.04 | (7-chloro-quinolin-4-yl)-[1-(3,5-diisopropoxy-benzyl)-piperidin-4-yl]-amine | (7-chloro-quinolin-4-yl)-piperidin-4-yl-amine dihydrochloride (intermediate A10) and 3,5-diisopropoxy-benzaldehyde (intermediate B10) | [M + H]+ 468.4 |
| 195 | 512.05 | 4-[4-(7-chloro-quinolin-4-ylamino)-piperidin-1-ylmethyl]-2,6-diethoxy-benzoic acid ethyl ester | (7-chloro-quinolin-4-yl)-piperidin-4-yl-amine dihydrochloride (intermediate A10) and 2,6-diethoxy-4-formyl-benzoic acid ethyl ester (intermediate B11) | [M + H]+ 512.3 |
| 196 | 457.98 | (7-chloro-quinolin-4-yl)-[1-(3,5-diethoxy-4-fluoro-benzyl)-piperidin-4-yl]-amine | (7-chloro-quinolin-4-yl)-piperidin-4-yl-amine dihydrochloride (intermediate A10) and 3,5-diethoxy-4-fluoro-benzaldehyde (intermediate B12) | [M + H]+ 458.4 |
| 197 | 474.43 | [1-(4-chloro-3,5-diethoxy-benzyl)-piperidin-4-yl]-(7-chloro-quinolin-4-yl)-amine | (7-chloro-quinolin-4-yl)-piperidin-4-yl-amine dihydrochloride (intermediate A10) and 4-chloro-3,5-diethoxy-benzaldehyde (intermediate B13) | [M + H]+ 474.0 |
| 198 | 518.89 | [1-(4-bromo-3,5-diethoxy-benzyl)-piperidin-4-yl]-(7-chloro-quinolin-4-yl)-amine | (7-chloro-quinolin-4-yl)-piperidin-4-yl-amine dihydrochloride (intermediate A10) and 4-bromo-3,5-diethoxy-benzaldehyde (intermediate B14) | [M + H]+ 520.2 |
| 199 | 505.06 | (7-chloro-quinolin-4-yl)-[1-(3,5-diethoxy-4-pyrrol-1-yl-benzyl)-piperidin-4-yl]-amine | (7-chloro-quinolin-4-yl)-piperidin-4-yl-amine dihydrochloride (intermediate A10) and 3,5-diethoxy-4-pyrrol-1-yl-benzaldehyde (intermediate B15) | [M + H]+ 505.4 |
| 200 | 534.07 | (7-chloro-quinolin-4-yl)-[1-(2,6-diethoxy-4'-fluoro-biphenyl-4-ylmethyl)-piperidin-4-yl]-amine | (7-chloro-quinolin-4-yl)-piperidin-4-yl-amine dihydrochloride (intermediate A10) and 2,6-diethoxy-4'-fluoro-biphenyl-4-carbaldehyde (intermediate B18) | [M + H]+ 534.5 |
| 201 | 346.86 | [1-(4-chloro-3-ethoxy-benzyl)-piperidin-4-yl]-pyrimidin-5-yl-amine | piperidin-4-yl-pyrimidin-5-yl-amine dihydrochloride (intermediate A11) and 4-chloro-3-ethoxy-benzaldehyde (intermediate B2) | [M + H]+ 347.2 |
| 202 | 370.50 | [1-(3-isobutoxy-4-methoxy-benzyl)-piperidin-4-yl]-pyrimidin-5-yl-amine | piperidin-4-yl-pyrimidin-5-yl-amine dihydrochloride (intermediate A11) and 3-isobutoxy-4-methoxy- | [M + H]+ 371.2 |

TABLE 1-continued

| No | MW | Compound Name | Starting Materials | ISP [M + H]+ |
|---|---|---|---|---|
| 203 | 394.52 | [1-(8-ethoxy-2,2-dimethyl-2H-chromen-6-ylmethyl)-piperidin-4-yl]-pyrimidin-5-yl-amine | benzaldehyde (intermediate B7) piperidin-4-yl-pyrimidin-5-yl-amine dihydrochloride (intermediate A11) and 8-ethoxy-2,2-dimethyl-2H-chromene-6-carbaldehyde (intermediate B8) | [M + H]+ 395.3 |
| 204 | 356.47 | [1-(3,5-diethoxy-benzyl)-piperidin-4-yl]-pyrimidin-5-yl-amine | piperidin-4-yl-pyrimidin-5-yl-amine dihydrochloride (intermediate A11) and 3,5-diethoxy-benzaldehyde (intermediate B9) | [M + H]+ 357.3 |
| 205 | 342.44 | 3-isopropoxy-5-[4-(pyrimidin-5-ylamino)-piperidin-1-ylmethyl]-phenol | piperidin-4-yl-pyrimidin-5-yl-amine dihydrochloride (intermediate A11) and 3-hydroxy-5-isopropoxy-benzaldehyde (intermediate B20) | [M + H]+ 343.3 |
| 206 | 384.52 | [1-(3,5-diisopropoxy-benzyl)-piperidin-4-yl]-pyrimidin-5-yl-amine | piperidin-4-yl-pyrimidin-5-yl-amine dihydrochloride (intermediate A11) and 3,5-diisopropoxy-benzaldehyde (intermediate B10) | [M + H]+ 385.4 |
| 207 | 374.46 | [1-(3,5-diethoxy-4-fluoro-benzyl)-piperidin-4-yl]-pyrimidin-5-yl-amine | piperidin-4-yl-pyrimidin-5-yl-amine dihydrochloride (intermediate A11) and 3,5-diethoxy-4-fluoro-benzaldehyde (intermediate B12) | [M + H]+ 375.3 |
| 208 | 390.91 | [1-(4-chloro-3,5-diethoxy-benzyl)-piperidin-4-yl]-pyrimidin-5-yl-amine | piperidin-4-yl-pyrimidin-5-yl-amine dihydrochloride (intermediate A11) and 4-chloro-3,5-diethoxy-benzaldehyde (intermediate B13) | [M + H]+ 391.2 |
| 209 | 435.37 | [1-(4-bromo-3,5-diethoxy-benzyl)-piperidin-4-yl]-pyrimidin-5-yl-amine | piperidin-4-yl-pyrimidin-5-yl-amine dihydrochloride (intermediate A11) and 4-bromo-3,5-diethoxy-benzaldehyde (intermediate B14) | [M + H]+ 437.2 |
| 210 | 371.48 | [1-(4-amino-3,5-diethoxy-benzyl)-piperidin-4-yl]-pyrimidin-5-yl-amine | piperidin-4-yl-pyrimidin-5-yl-amine dihydrochloride (intermediate A11) and 4-amino-3,5-diethoxy-benzaldehyde (intermediate B17) | [M + H]+ 372.2 |
| 211 | 421.54 | [1-(3,5-diethoxy-4-pyrrol-1-yl-benzyl)-piperidin-4-yl]-pyrimidin-5-yl-amine | piperidin-4-yl-pyrimidin-5-yl-amine dihydrochloride (intermediate A11) and 3,5-diethoxy-4-pyrrol-1-yl-benzaldehyde (intermediate B15) | [M + H]+ 422.2 |
| 212 | 402.54 | [1-(3-ethoxy-4-methyl-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 3-ethoxy-4-methyl-benzaldehyde (intermediate B21) | [M + H]+ 403.3 |
| 213 | 406.50 | [1-(3-ethoxy-4-fluoro-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 3-ethoxy-4-fluoro-benzaldehyde (intermediate B1) | [M + H]+ 407.2 |
| 214 | 422.96 | [1-(4-chloro-3-ethoxy-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 4-chloro-3-ethoxy-benzaldehyde (intermediate B2) | [M + H]+ 423.0 |
| 215 | 418.54 | [1-(3-ethoxy-4-methoxy-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 3-ethoxy-4-methoxy- | [M + H]+ 419.1 |

TABLE 1-continued

| No | MW | Compound Name | Starting Materials | ISP [M + H]+ |
|---|---|---|---|---|
| 216 | 444.58 | [1-(4-allyloxy-3-ethoxy-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 4-allyloxy-3-ethoxy-benzaldehyde (commercially available) benzaldehyde (commercially available) | [M + H]+ 445.1 |
| 217 | 460.62 | [1-(3-ethoxy-4-isobutoxy-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 3-ethoxy-4-isobutoxy-benzaldehyde (commercially available) | [M + H]+ 461.1 |
| 218 | 474.65 | {1-[3-ethoxy-4-(1-ethyl-propoxy)-benzyl]-piperidin-4-yl}-(2-phenyl-pyrimidin-5-yl)-amine | (2-phenyl-pyrimidin-5-yl)-piperidin-4-yl-amine dihydrochloride (intermediate A12) and 3-ethoxy-4-(1-ethyl-propoxy)-benzaldehyde (intermediate B3) | [M + H]+ 475.3 |
| 219 | 472.63 | [1-(4-cyclopentyloxy-3-ethoxy-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 4-cyclopentyloxy-3-ethoxy-benzaldehyde (commercially available) | [M + H]+ 473.1 |
| 220 | 454.52 | [1-(4-difluoromethoxy-3-ethoxy-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 4-difluoromethoxy-3-ethoxy-benzaldehyde (commercially available) | [M + H]+ 455.3 |
| 221 | 432.57 | [1-(4-methox-3-propoxy-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 4-methoxy-3-propoxy-benzaldehyde (intermediate B4) | [M + H]+ 433.2 |
| 222 | 432.57 | [1-(3-isopropoxy-4-methoxy-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 3-isopropoxy-4-methoxy-benzaldehyde (commercially available) | [M + H]+ 433.4 |
| 223 | 430.55 | [1-(3-allyloxy-4-methoxy-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 3-allyloxy-4-methoxy-benzaldehyde (intermediate B5) | [M + H]+ 431.2 |
| 224 | 446.59 | [1-(3-butoxy-4-methoxy-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 3-butoxy-4-methoxy-benzaldehyde (intermediate B6) | [M + H]+ 447.1 |
| 225 | 446.59 | [1-(3-isobutoxy-4-methoxy-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 3-isobutoxy-4-methoxy-benzaldehyde (intermediate B7) | [M + H]+ 447.1 |
| 226 | 458.61 | [1-(3-cyclopentyloxy-4-methoxy-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 3-cyclopentyloxy-4-methoxy-benzaldehyde (commercially available) | [M + H]+ 459.3 |
| 227 | 470.62 | [1-(8-ethoxy-2,2-dimethyl-2H-chromen-6-ylmethyl)-piperidin-4-yl]-(2-phenyl-pyrimidin-5-yl)-amine | (2-phenyl-pyrimidin-5-yl)-piperidin-4-yl-amine dihydrochloride (intermediate A12) and 8-ethoxy-2,2-dimethyl-2H-chromene-6-carbaldehyde (intermediate B8) | [M + H]+ 471.1 |
| 228 | 432.57 | [1-(3,5-diethoxy-benzyl)-piperidin-4-yl]-(2- | (2-phenyl-pyrimidin-5-yl)-piperidin-4-yl-amine | [M + H]+ 433.4 |

TABLE 1-continued

| No | MW | Compound Name | Starting Materials | ISP [M + H]⁺ |
|---|---|---|---|---|
| | | phenyl-pyrimidin-5-yl)-amine | dihydrochloride (intermediate A12) and 3,5-diethoxy-benzaldehyde (intermediate B9) | |
| 229 | 504.63 | 2,6-diethoxy-4-[4-(2-phenyl-pyrimidin-5-ylamino)-piperidin-1-ylmethyl]-benzoic acid ethyl ester | (2-phenyl-pyrimidin-5-yl)-piperidin-4-yl-amine dihydrochloride (intermediate A12) and 2,6-diethoxy-4-formyl-benzoic acid ethyl ester (intermediate B11) | [M + H]⁺ 505.2 |
| 230 | 450.56 | [1-(3,5-diethoxy-4-fluoro-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 3,5-diethoxy-4-fluoro-benzaldehyde (intermediate B12) | [M + H]⁺ 451.1 |
| 231 | 467.01 | [1-(4-chloro-3,5-diethoxy-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 4-chloro-3,5-diethoxy-benzaldehyde (intermediate B13) | [M + H]⁺ 467.2 |
| 232 | 511.47 | [1-(4-bromo-3,5-diethoxy-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 4-bromo-3,5-diethoxy-benzaldehyde (intermediate B14) | [M + H]⁺ 513.2 |
| 233 | 497.64 | [1-(3,5-diethoxy-4-pyrrol-1-yl-benzyl)-piperidin-4-yl]-(2-phenyl-pyrimidin-5-yl)-amine | (2-phenyl-pyrimidin-5-yl)-piperidin-4-yl-amine dihydrochloride (intermediate A12) and 3,5-diethoxy-4-pyrrol-1-yl-benzaldehyde (intermediate B15) | [M + H]⁺ 498.1 |
| 234 | 526.66 | [1-(2,6-diethoxy-4'-fluoro-biphenyl-4-ylmethyl)-piperidin-4-yl]-(2-phenyl-pyrimidin-5-yl)-amine | (2-phenyl-pyrimidin-5-yl)-piperidin-4-yl-amine dihydrochloride (intermediate A12) and 2,6-diethoxy-4'-fluoro-biphenyl-4-carbaldehyde (intermediate B18) | [M + H]⁺ 527.2 |
| 235 | 431.97 | [1-(4-chloro-3-ethoxy-benzyl)-piperidin-4-yl]-(2-morpholin-4-yl-pyrimidin-5-yl)-amine | (2-morpholin-4-yl-pyrimidin-5-yl)-piperidin-4-yl-amine dihydrochloride (intermediate A13) and 4-chloro-3-ethoxy-benzaldehyde (intermediate B2) | [M + H]⁺ 432.3 |
| 236 | 476.02 | [1-(4-chloro-3,5-diethoxy-benzyl)-piperidin-4-yl]-(2-morpholin-4-yl-pyrimidin-5-yl)-amine | (2-morpholin-4-yl-pyrimidin-5-yl)-piperidin-4-yl-amine dihydrochloride (intermediate A13) and 4-chloro-3,5-diethoxy-benzaldehyde (intermediate B13) | [M + H]⁺ 476.2 |
| 237 | 535.66 | [1-(2,6-diethoxy-4'-fluoro-biphenyl-4-ylmethyl)-piperidin-4-yl]-(2-morpholin-4-yl-pyrimidin-5-yl)-amine | (2-morpholin-4-yl-pyrimidin-5-yl)-piperidin-4-yl-amine dihydrochloride (intermediate A13) and 2,6-diethoxy-4'-fluoro-biphenyl-4-carbaldehyde (intermediate B18) | [M + H]⁺ 536.3 |

Example A

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |

101
-continued

| Ingredients | Per tablet | |
|---|---|---|
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 mg or 350 mg, respectively. The kernels are lacquered with an aqueous solution/suspension of the above mentioned film coat

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula I | 3.0 mg |
|---|---|
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula I | 50.0 mg |
|---|---|
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

It is to be understood that the invention is not limited to the particular embodiments of the invention described above, as variations of the particular embodiments may be made and still fall within the scope of the appended claims

What is claimed is:
1. A compound of formula I:

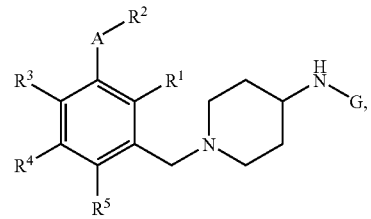

wherein
A is —O— or —NH—;
$R^1$ is selected from the group consisting of hydrogen, $C_{1-7}$-alkoxy and halogen;
$R^2$ is selected from the group consisting of $C_{2-7}$-alkyl, $C_{2-7}$-alkenyl, $C_{3-7}$-alkinyl, $C_{3-7}$-cycloalkyl, halogen-$C_{1-7}$-alkyl, $C_{1-7}$-alkoxy-$C_{1-7}$-alkyl and benzyl;
$R^3$ is selected from the group consisting of hydrogen, $C_{1-7}$-alkyl,
hydroxy, $C_{1-7}$-alkoxy, $C_{2-7}$-alkenyloxy,
hydroxy-$C_{1-7}$-alkoxy, $C_{1-7}$-alkoxy-$C_{1-7}$-alkoxy,
—O-benzyl, —O—$C_{3-7}$-cycloalkyl,
unsubstituted phenyl or phenyl substituted by one to three groups independently selected from $C_{1-7}$-alkyl, halogen and $C_{1-7}$-alkoxy,
halogen, halogen-$C_{1-7}$-alkyl, halogen-$C_{1-7}$-alkoxy, amino, pyrrolyl, and
—C(O)OR$^6$, wherein $R^6$ is $C_{1-7}$-alkyl;
$R^4$ is selected from the group consisting of hydrogen, hydroxy, $C_{1-7}$-alkoxy, amino, nitro, hydroxy-$C_{1-7}$-alkoxy, $C_{1-7}$-alkoxy-$C_{1-7}$-alkoxy, and —O-benzyl;
or $R^3$ and $R^4$ are bonded to each other to form a ring together with the carbon atoms they are attached to and $R^3$ and $R^4$ together are —O—C(CH$_3$)$_2$—CH═CH—;
$R^5$ is selected from the group consisting of hydrogen, halogen and $C_{1-7}$-alkoxy;

G is selected from the groups

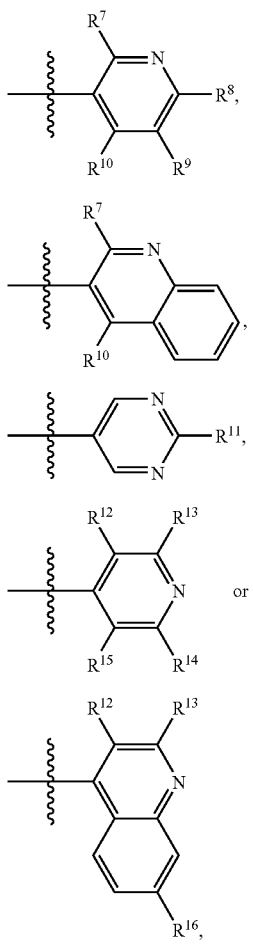

wherein
$R^7$, $R^9$ and $R^{10}$ independently from each other are hydrogen or $C_{1-7}$-alkyl;
$R^8$ is selected from the group consisting of hydrogen, amino, heterocyclyl selected from the group consisting of pyrrolidinyl, piperidinyl, piperazinyl and morpholinyl, and —NH—C(O)—$R^{15}$, wherein $R^{15}$ is $C_{1-7}$-alkyl;
$R^{11}$ is selected from the group consisting of hydrogen, $C_{1-7}$-alkyl, phenyl, and heterocyclyl selected from the group consisting of pyrrolidinyl, piperidinyl, piperazinyl and morpholinyl;
$R^{12}$, $R^{13}$, $R^{14}$ and $R^{15}$ independently from each other are selected from the group consisting of hydrogen, $C_{1-7}$-alkyl, halogen and halogen-$C_{1-7}$-alkyl;
$R^{16}$ is hydrogen or halogen;
and pharmaceutically acceptable salts thereof.

2. The compound according to claim 1, wherein A is O.
3. The compound according to claim 1, wherein $R^1$ is hydrogen.
4. The compound according to claim 1, wherein $R^2$ is selected from the group consisting of $C_{2-7}$-alkyl, $C_{2-7}$-alkenyl, $C_{3-7}$-alkinyl, $C_{3-7}$-cycloalkyl and halogen-$C_{1-7}$-alkyl.
5. The compound according to claim 1, wherein $R^2$ is selected from the group consisting of ethyl, propyl, isopropyl, allyl, 2-fluoroethyl, butyl, isobutyl, cyclopentyl and 2-propynyl.

6. The compound according to claim 1, wherein $R^3$ is selected from the group consisting of
hydrogen, $C_{1-7}$-alkyl, hydroxy, $C_{1-7}$-alkoxy, $C_{2-7}$-alkenyloxy,
hydroxy-$C_{1-7}$-alkoxy, —O-benzyl, —O—$C_{3-7}$-cycloalkyl,
phenyl substituted by halogen,
halogen, halogen-$C_{1-7}$-alkoxy,
amino, pyrrolyl, and
—C(O)$OR^6$, wherein $R^6$ is $C_{1-7}$-alkyl.
7. The compound according to claim 1, wherein $R^3$ is selected from the group consisting of hydrogen, $C_{1-7}$-alkoxy, halogen, halogen-$C_{1-7}$-alkoxy and pyrrolyl.
8. The compound according to claim 1, wherein $R^3$ is halogen.
9. The compound according to claim 1, wherein $R^4$ is selected from the group consisting of hydrogen, hydroxy and $C_{1-7}$-alkoxy.
10. The compound according to claim 1, wherein $R^5$ is hydrogen.
11. The compound according to claim 1, wherein G is

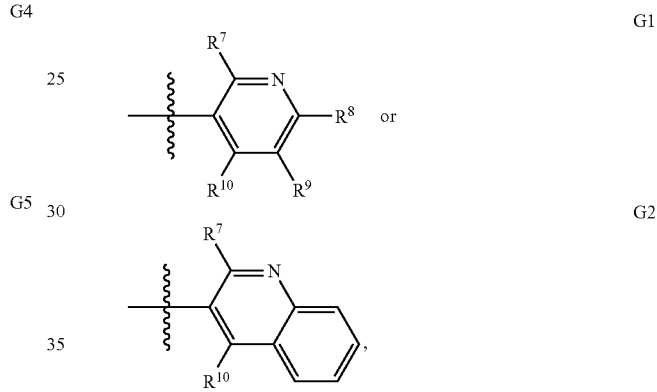

and wherein
$R^7$, $R^9$ and $R^{10}$ independently from each other are hydrogen or $C_{1-7}$-alkyl; and
$R^8$ is selected from the group consisting of hydrogen, amino, heterocyclyl selected from the group consisting of pyrrolidinyl, piperidinyl, piperazinyl and morpholinyl, and
—NH—C(O)—$R^{15}$, wherein $R^{15}$ is $C_{1-7}$-alkyl.
12. The compound according to claim 1, wherein G is

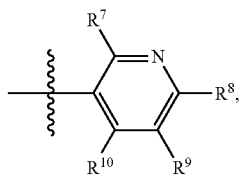

and wherein
$R^7$, $R^9$ and $R^{10}$ independently from each other are hydrogen or $C_{1-7}$-alkyl; and
$R^8$ is selected from the group consisting of hydrogen, amino, heterocyclyl selected from the group consisting of pyrrolidinyl, piperidinyl, piperazinyl and morpholinyl, and
—NH—C(O)—$R^{15}$, wherein $R^{15}$ is $C_{1-7}$-alkyl.
13. The compound according to claim 12, wherein $R^7$, $R^8$, $R^9$ and $R^{10}$ are hydrogen.

14. The compound according to claim 1, wherein G is

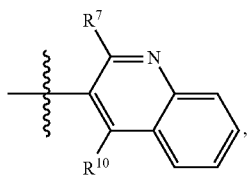

and wherein $R^7$ and $R^{10}$ independently from each other are hydrogen or $C_{1-7}$-alkyl.

15. The compound according to claim 14, wherein $R^7$ and $R^{10}$ are hydrogen.

16. The compound according to claim 1, wherein G is

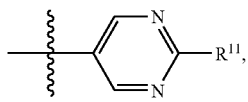

and wherein $R^{11}$ is selected from the group consisting of hydrogen, $C_{1-7}$-alkyl, phenyl, and heterocyclyl selected from the group consisting of pyrrolidinyl, piperidinyl, piperazinyl and morpholinyl.

17. The compound according to claim 16, wherein $R^{11}$ is phenyl.

18. The compound according to claim 1, wherein G is

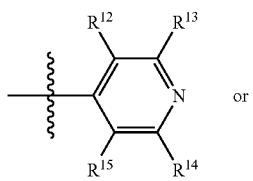

or

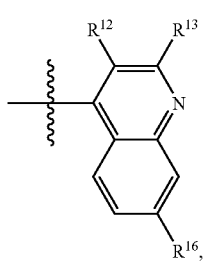

and wherein
$R^{12}$, $R^{13}$, $R^{14}$ and $R^{15}$ independently from each other are selected from the group consisting of hydrogen, $C_{1-7}$-alkyl, halogen and halogen-$C_{1-7}$-alkyl; and
$R^{16}$ is hydrogen or halogen.

19. The compound according to claim 1, wherein G is

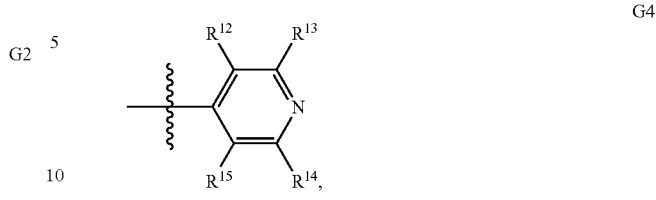

and wherein $R^{12}$, $R^{13}$, $R^{14}$ and $R^{15}$ independently from each other are selected from the group consisting of hydrogen, $C_{1-7}$-alkyl, halogen and halogen-$C_{1-7}$-alkyl.

20. The compound according to claim 1, wherein G is

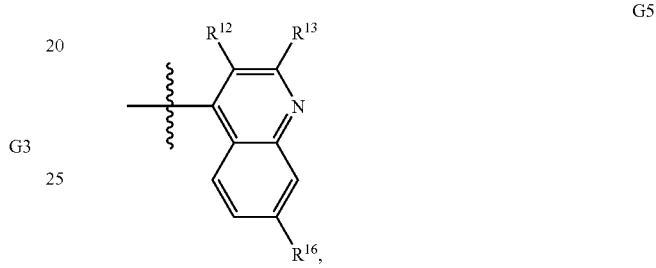

and wherein $R^{12}$ and $R^{13}$ independently from each other are selected from the group consisting of hydrogen, $C_{1-7}$-alkyl, halogen and halogen-$C_{1-7}$-alkyl, and $R^{16}$ is hydrogen or halogen.

21. Compounds of formula I according to claim 1, selected from the group consisting of
[1-(3-ethoxy-4-methyl-benzyl)-piperidin-4-yl]-pyridin-3-yl-amine,
[1-(3-ethoxy-4-fluoro-benzyl)-piperidin-4-yl]-pyridin-3-yl-amine,
[1-(4-chloro-3-ethoxy-benzyl)-piperidin-4-yl]-pyridin-3-yl-amine,
[1-(3-ethoxy-4-methoxy-benzyl)-piperidin-4-yl]-pyridin-3-yl-amine,
[1-(4-allyloxy-3-ethoxy-benzyl)-piperidin-4-yl]-pyridin-3-yl-amine,
[1-(3-ethoxy-4-isobutoxy-benzyl)-piperidin-4-yl]-pyridin-3-yl-amine,
{1-[3-ethoxy-4-(1-ethyl-propoxy)-benzyl]-piperidin-4-yl}-pyridin-3-yl-amine,
[1-(4-cyclopentyloxy-3-ethoxy-benzyl)-piperidin-4-yl]-pyridin-3-yl-amine,
[1-(4-benzyloxy-3-ethoxy-benzyl)-piperidin-4-yl]-pyridin-3-yl-amine,
[1-(4-difluoromethoxy-3-ethoxy-benzyl)-piperidin-4-yl]-pyridin-3-yl-amine,
[1-(4-methoxy-3-propoxy-benzyl)-piperidin-4-yl]-pyridin-3-yl-amine,
[1-(3-allyloxy-4-methoxy-benzyl)-piperidin-4-yl]-pyridin-3-yl-amine,
[1-(3-butoxy-4-methoxy-benzyl)-piperidin-4-yl]-pyridin-3-yl-amine,
[1-(3-isobutoxy-4-methoxy-benzyl)-piperidin-4-yl]-pyridin-3-yl-amine,
[1-(3-cyclopentyloxy-4-methoxy-benzyl)-piperidin-4-yl]-pyridin-3-yl-amine,

[1-(8-ethoxy-2,2-dimethyl-2H-chromen-6-ylmethyl)-piperidin-4-yl]-pyridin-3-yl-amine,
[1-(3,5-diethoxy-benzyl)-piperidin-4-yl]-pyridin-3-yl-amine,
[1-(3,5-diisopropoxy-benzyl)-piperidin-4-yl]-pyridin-3-yl-amine,
2,6-diethoxy-4-[4-(pyridin-3-ylamino)-piperidin-1-ylmethyl]-benzoic acid ethyl ester,
[1-(3,5-diethoxy-4-fluoro-benzyl)-piperidin-4-yl]-pyridin-3-yl-amine,
[1-(4-chloro-3,5-diethoxy-benzyl)-piperidin-4-yl]-pyridin-3-yl-amine,
[1-(4-bromo-3,5-diethoxy-benzyl)-piperidin-4-yl]-pyridin-3-yl-amine,
[1-(3,5-diethoxy-4-pyrrol-1-yl-benzyl)-piperidin-4-yl]-pyridin-3-yl-amine,
[1-(3-ethoxy-4-fluoro-benzyl)-piperidin-4-yl]-(6-morpholin-4-yl-pyridin-3-yl)-amine,
[1-(4-chloro-3-ethoxy-benzyl)-piperidin-4-yl]-(6-morpholin-4-yl-pyridin-3-yl)-amine,
[1-(3-ethoxy-4-methoxy-benzyl)-piperidin-4-yl]-(6-morpholin-4-yl-pyridin-3-yl)-amine,
[1-(4-cyclopentyloxy-3-ethoxy-benzyl)-piperidin-4-yl]-(6-morpholin-4-yl-pyridin-3-yl)-amine,
[1-(4-benzyloxy-3-ethoxy-benzyl)-piperidin-4-yl]-(6-morpholin-4-yl-pyridin-3-yl)-amine,
[1-(4-difluoromethoxy-3-ethoxy-benzyl)-piperidin-4-yl]-(6-morpholin-4-yl-pyridin-3-yl)-amine,
[1-(4-methoxy-3-propoxy-benzyl)-piperidin-4-yl]-(6-morpholin-4-yl-pyridin-3-yl)-amine,
[1-(3-isopropoxy-4-methoxy-benzyl)-piperidin-4-yl]-(6-morpholin-4-yl-pyridin-3-yl)-amine,
{1-[3-(2-fluoro-ethoxy)-4-methoxy-benzyl]-piperidin-4-yl}-(6-morpholin-4-yl-pyridin-3-yl)-amine,
[1-(3-allyloxy-4-methoxy-benzyl)-piperidin-4-yl]-(6-morpholin-4-yl-pyridin-3-yl)-amine,
[1-(3-isobutoxy-4-methoxy-benzyl)-piperidin-4-yl]-(6-morpholin-4-yl-pyridin-3-yl)-amine,
[1-(3-cyclopentyloxy-4-methoxy-benzyl)-piperidin-4-yl]-(6-morpholin-4-yl-pyridin-3-yl)-amine,
[1-(8-ethoxy-2,2-dimethyl-2H-chromen-6-ylmethyl)-piperidin-4-yl]-(6-morpholin-4-yl-pyridin-3-yl)-amine,
[1-(3,5-diethoxy-benzyl)-piperidin-4-yl]-(6-morpholin-4-yl-pyridin-3-yl)-amine,
[1-(3,5-diisopropoxy-benzyl)-piperidin-4-yl]-(6-morpholin-4-yl-pyridin-3-yl)-amine,
[1-(3,5-diethoxy-4-fluoro-benzyl)-piperidin-4-yl]-(6-morpholin-4-yl-pyridin-3-yl)-amine,
[1-(4-chloro-3,5-diethoxy-benzyl)-piperidin-4-yl]-(6-morpholin-4-yl-pyridin-3-yl)-amine,
[1-(4-bromo-3,5-diethoxy-benzyl)-piperidin-4-yl]-(6-morpholin-4-yl-pyridin-3-yl)-amine,
[1-(4-amino-3,5-diethoxy-benzyl)-piperidin-4-yl]-(6-morpholin-4-yl-pyridin-3-yl)-amine,
[1-(3,5-diethoxy-4-pyrrol-1-yl-benzyl)-piperidin-4-yl]-(6-morpholin-4-yl-pyridin-3-yl)-amine,
[1-(2,6-diethoxy-4'-fluoro-biphenyl-4-ylmethyl)-piperidin-4-yl]-(6-morpholin-4-yl-pyridin-3-yl)-amine,
N-{5-[1-(3-ethoxy-4-fluoro-benzyl)-piperidin-4-ylamino]-pyridin-2-yl}-acetamide,
N-{5-[1-(4-chloro-3-ethoxy-benzyl)-piperidin-4-ylamino]-pyridin-2-yl}-acetamide,
N-{5-[1-(3-ethoxy-4-methoxy-benzyl)-piperidin-4-ylamino]-pyridin-2-yl}-acetamide,
N-{5-[1-(4-cyclopentyloxy-3-ethoxy-benzyl)-piperidin-4-ylamino]-pyridin-2-yl}-acetamide,
N-{5-[1-(4-benzyloxy-3-ethoxy-benzyl)-piperidin-4-ylamino]-pyridin-2-yl}-acetamide,
N-{5-[1-(4-difluoromethoxy-3-ethoxy-benzyl)-piperidin-4-ylamino]-pyridin-2-yl}-acetamide,
N-{5-[1-(4-methoxy-3-propoxy-benzyl)-piperidin-4-ylamino]-pyridin-2-yl}-acetamide,
N-{5-[1-(3-isopropoxy-4-methoxy-benzyl)-piperidin-4-ylamino]-pyridin-2-yl}-acetamide,
N-{5-[1-(3-isobutoxy-4-methoxy-benzyl)-piperidin-4-ylamino]-pyridin-2-yl}-acetamide,
N-{5-[1-(3-cyclopentyloxy-4-methoxy-benzyl)-piperidin-4-ylamino]-pyridin-2-yl}-acetamide,
N-{5-[1-(8-ethoxy-2,2-dimethyl-2H-chromen-6-ylmethyl)-piperidin-4-ylamino]-pyridin-2-yl}-acetamide,
N-{5-[1-(3,5-diethoxy-benzyl)-piperidin-4-ylamino]-pyridin-2-yl}-acetamide,
N-{5-[1-(3,5-diisopropoxy-benzyl)-piperidin-4-ylamino]-pyridin-2-yl}-acetamide,
N-{5-[1-(3,5-diethoxy-4-fluoro-benzyl)-piperidin-4-ylamino]-pyridin-2-yl}-acetamide,
N-{5-[1-(4-chloro-3,5-diethoxy-benzyl)-piperidin-4-ylamino]-pyridin-2-yl}-acetamide,
N-{5-[1-(4-bromo-3,5-diethoxy-benzyl)-piperidin-4-ylamino]-pyridin-2-yl}-acetamide,
N-{5-[1-(4-amino-3,5-diethoxy-benzyl)-piperidin-4-ylamino]-pyridin-2-yl}-acetamide,
N-{5-[1-(3,5-diethoxy-4-pyrrol-1-yl-benzyl)-piperidin-4-ylamino]-pyridin-2-yl}-acetamide,
N-{5-[1-(2,6-diethoxy-4'-fluoro-biphenyl-4-ylmethyl)-piperidin-4-ylamino]-pyridin-2-yl}-acetamide,
$N^5$-[1-(3-ethoxy-4-fluoro-benzyl)-piperidin-4-yl]-3-methyl-pyridine-2,5-diamine,
$N^5$-[1-(4-chloro-3-ethoxy-benzyl)-piperidin-4-yl]-3-methyl-pyridine-2,5-diamine,
$N^5$-[1-(3-ethoxy-4-methoxy-benzyl)-piperidin-4-yl]-3-methyl-pyridine-2,5-diamine,
$N^5$-[1-(3-ethoxy-4-isopropoxy-benzyl)-piperidin-4-yl]-3-methyl-pyridine-2,5-diamine,
$N^5$-[1-(4-difluoromethoxy-3-ethoxy-benzyl)-piperidin-4-yl]-3-methyl-pyridine-2,5-diamine,
$N^5$-[1-(4-methoxy-3-propoxy-benzyl)-piperidin-4-yl]-3-methyl-pyridine-2,5-diamine,
$N^5$-[1-(3-isopropoxy-4-methoxy-benzyl)-piperidin-4-yl]-3-methyl-pyridine-2,5-diamine,
$N^5$-[1-(3-allyloxy-4-methoxy-benzyl)-piperidin-4-yl]-3-methyl-pyridine-2,5-diamine,
$N^5$-[1-(3-isobutoxy-4-methoxy-benzyl)-piperidin-4-yl]-3-methyl-pyridine-2,5-diamine,
$N^5$-[1-(3-cyclopentyloxy-4-methoxy-benzyl)-piperidin-4-yl]-3-methyl-pyridine-2,5-diamine,
$N^5$-[1-(3,5-diethoxy-benzyl)-piperidin-4-yl]-3-methyl-pyridine-2,5-diamine,
$N^5$-[1-(3,5-diisopropoxy-benzyl)-piperidin-4-yl]-3-methyl-pyridine-2,5-diamine,
4-[4-(6-amino-5-methyl-pyridin-3-ylamino)-piperidin-1-ylmethyl]-2,6-diethoxy-benzoic acid ethyl ester,
$N^5$-[1-(3,5-diethoxy-4-fluoro-benzyl)-piperidin-4-yl]-3-methyl-pyridine-2,5-diamine,
$N^5$-[1-(3,5-diethoxy-4-pyrrol-1-yl-benzyl)-piperidin-4-yl]-3-methyl-pyridine-2,5-diamine,
$N^5$-[1-(2,6-diethoxy-4'-fluoro-biphenyl-4-ylmethyl)-piperidin-4-yl]-3-methyl-pyridine-2,5-diamine,
N-{5-[1-(4-chloro-3-ethoxy-benzyl)-piperidin-4-ylamino]-6-methyl-pyridin-2-yl}-acetamide,
N-{5-[1-(3-isobutoxy-4-methoxy-benzyl)-piperidin-4-ylamino]-6-methyl-pyridin-2-yl}-acetamide, N-{5-[1-(3,5-diisopropoxy-benzyl)-piperidin-4-ylamino]-6-methyl-pyridin-2-yl}-acetamide,
N-{5-[1-(3,5-diethoxy-4-fluoro-benzyl)-piperidin-4-ylamino]-6-methyl-pyridin-2-yl}-acetamide,
N-{5-[1-(4-chloro-3,5-diethoxy-benzyl)-piperidin-4-ylamino]-6-methyl-pyridin-2-yl}-acetamide,
N-{5-[1-(4-amino-3,5-diethoxy-benzyl)-piperidin-4-ylamino]-6-methyl-pyridin-2-yl}-acetamide,
N-{5-[1-(3,5-diethoxy-4-pyrrol-1-yl-benzyl)-piperidin-4-ylamino]-6-methyl-pyridin-2-yl}-acetamide,
N-{5-[1-(2,6-diethoxy-4'-fluoro-biphenyl-4-ylmethyl)-piperidin-4-ylamino]-6-methyl-pyridin-2-yl}-acetamide,
[1-(3-ethoxy-4-fluoro-benzyl)-piperidin-4-yl]-quinolin-3-yl-amine,
[1-(4-chloro-3-ethoxy-benzyl)-piperidin-4-yl]-quinolin-3-yl-amine,
2-ethoxy-4-[4-(quinolin-3-ylamino)-piperidin-1-ylmethyl]-phenol,
[1-(3-ethoxy-4-methoxy-benzyl)-piperidin-4-yl]-quinolin-3-yl-amine,
[1-(3,4-diethoxy-benzyl)-piperidin-4-yl]-quinolin-3-yl-amine,
[1-(4-allyloxy-3-ethoxy-benzyl)-piperidin-4-yl]-quinolin-3-yl-amine,
[1-(3-ethoxy-4-isopropoxy-benzyl)-piperidin-4-yl]-quinolin-3-yl-amine,
[1-(3-ethoxy-4-isobutoxy-benzyl)-piperidin-4-yl]-quinolin-3-yl-amine,
{1-[3-ethoxy-4-(1-ethyl-propoxy)-benzyl]-piperidin-4-yl}-quinolin-3-yl-amine,
[1-(4-cyclopentyloxy-3-ethoxy-benzyl)-piperidin-4-yl]-quinolin-3-yl-amine,
[1-(4-benzyloxy-3-ethoxy-benzyl)-piperidin-4-yl]-quinolin-3-yl-amine,
[1-(4-difluoromethoxy-3-ethoxy-benzyl)-piperidin-4-yl]-quinolin-3-yl-amine,
[1-(4-methoxy-3-propoxy-benzyl)-piperidin-4-yl]-quinolin-3-yl-amine,
[1-(3-isopropoxy-4-methoxy-benzyl)-piperidin-4-yl]-quinolin-3-yl-amine,
{1-[3-(2-fluoro-ethoxy)-4-methoxy-benzyl]-piperidin-4-yl}-quinolin-3-yl-amine,
[1-(3-allyloxy-4-methoxy-benzyl)-piperidin-4-yl]-quinolin-3-yl-amine,
[1-(4-methoxy-3-prop-2-ynyloxy-benzyl)-piperidin-4-yl]-quinolin-3-yl-amine,
[1-(3-butoxy-4-methoxy-benzyl)-piperidin-4-yl]-quinolin-3-yl-amine,
[1-(3-isobutoxy-4-methoxy-benzyl)-piperidin-4-yl]-quinolin-3-yl-amine,
[1-(3-cyclopentyloxy-4-methoxy-benzyl)-piperidin-4-yl]-quinolin-3-yl-amine,
2-{2-ethoxy-5-fluoro-4-[4-(quinolin-3-ylamino)-piperidin-1-ylmethyl]-phenoxy}-ethanol,
[1-(8-ethoxy-2,2-dimethyl-2H-chromen-6-ylmethyl)-piperidin-4-yl]-quinolin-3-yl-amine,
[1-(3,5-diethoxy-benzyl)-piperidin-4-yl]-quinolin-3-yl-amine,
[1-(3,5-diisopropoxy-benzyl)-piperidin-4-yl]-quinolin-3-yl-amine,
2,6-diethoxy-4-[4-(quinolin-3-ylamino)-piperidin-1-ylmethyl]-benzoic acid ethyl ester,
[1-(3,5-diethoxy-4-fluoro-benzyl)-piperidin-4-yl]-quinolin-3-yl-amine,
[1-(4-chloro-3,5-diethoxy-benzyl)-piperidin-4-yl]-quinolin-3-yl-amine,
[1-(4-bromo-3,5-diethoxy-benzyl)-piperidin-4-yl]-quinolin-3-yl-amine,
[1-(4-amino-3,5-diethoxy-benzyl)-piperidin-4-yl]-quinolin-3-yl-amine,
[1-(3,5-diethoxy-4-pyrrol-1-yl-benzyl)-piperidin-4-yl]-quinolin-3-yl-amine,
[1-(2,6-diethoxy-4'-fluoro-biphenyl-4-ylmethyl)-piperidin-4-yl]-quinolin-3-yl-amine,
[1-(3-ethoxy-4-fluoro-benzyl)-piperidin-4-yl]-(2-methyl-pyridin-4-yl)-amine,
[1-(4-chloro-3-ethoxy-benzyl)-piperidin-4-yl]-(2-methyl-pyridin-4-yl)-amine,
[1-(3-ethoxy-4-methoxy-benzyl)-piperidin-4-yl]-(2-methyl-pyridin-4-yl)-amine,
[1-(3-ethoxy-4-isobutoxy-benzyl)-piperidin-4-yl]-(2-methyl-pyridin-4-yl)-amine,
[1-(4-cyclopentyloxy-3-ethoxy-benzyl)-piperidin-4-yl]-(2-methyl-pyridin-4-yl)-amine,
[1-(4-benzyloxy-3-ethoxy-benzyl)-piperidin-4-yl]-(2-methyl-pyridin-4-yl)-amine,
[1-(4-difluoromethoxy-3-ethoxy-benzyl)-piperidin-4-yl]-(2-methyl-pyridin-4-yl)-amine,
[1-(4-methoxy-3-propoxy-benzyl)-piperidin-4-yl]-(2-methyl-pyridin-4-yl)-amine,
[1-(3-isobutoxy-4-methoxy-benzyl)-piperidin-4-yl]-(2-methyl-pyridin-4-yl)-amine,
[1-(3-cyclopentyloxy-4-methoxy-benzyl)-piperidin-4-yl]-(2-methyl-pyridin-4-yl)-amine,
[1-(8-ethoxy-2,2-dimethyl-2H-chromen-6-ylmethyl)-piperidin-4-yl]-(2-methyl-pyridin-4-yl)-amine,
[1-(3,5-diethoxy-benzyl)-piperidin-4-yl]-(2-methyl-pyridin-4-yl)-amine,
[1-(3,5-diisopropoxy-benzyl)-piperidin-4-yl]-(2-methyl-pyridin-4-yl)-amine,
2,6-diethoxy-4-[4-(2-methyl-pyridin-4-ylamino)-piperidin-1-ylmethyl]-benzoic acid ethyl ester,
[1-(3,5-diethoxy-4-fluoro-benzyl)-piperidin-4-yl]-(2-methyl-pyridin-4-yl)-amine,
[1-(4-chloro-3,5-diethoxy-benzyl)-piperidin-4-yl]-(2-methyl-pyridin-4-yl)-amine,
[1-(4-bromo-3,5-diethoxy-benzyl)-piperidin-4-yl]-(2-methyl-pyridin-4-yl)-amine,
[1-(4-amino-3,5-diethoxy-benzyl)-piperidin-4-yl]-(2-methyl-pyridin-4-yl)-amine,
[1-(3,5-diethoxy-4-pyrrol-1-yl-benzyl)-piperidin-4-yl]-(2-methyl-pyridin-4-yl)-amine,
[1-(2,6-diethoxy-4'-fluoro-biphenyl-4-ylmethyl)-piperidin-4-yl]-(2-methyl-pyridin-4-yl)-amine,
[1-(4-chloro-3-ethoxy-benzyl)-piperidin-4-yl]-(3-fluoro-pyridin-4-yl)-amine,
[1-(4-chloro-3,5-diethoxy-benzyl)-piperidin-4-yl]-(3-fluoro-pyridin-4-yl)-amine,
[1-(4-amino-3,5-diethoxy-benzyl)-piperidin-4-yl]-(3-fluoro-pyridin-4-yl)-amine,
[1-(2,6-diethoxy-4'-fluoro-biphenyl-4-ylmethyl)-piperidin-4-yl]-(3-fluoro-pyridin-4-yl)-amine,
[1-(3-ethoxy-4-fluoro-benzyl)-piperidin-4-yl]-quinolin-4-yl-amine,
[1-(4-chloro-3-ethoxy-benzyl)-piperidin-4-yl]-quinolin-4-yl-amine,
2-ethoxy-4-[4-(quinolin-4-ylamino)-piperidin-1-ylmethyl]-phenol,
[1-(3-ethoxy-4-methoxy-benzyl)-piperidin-4-yl]-quinolin-4-yl-amine,
[1(3,4-diethoxy-benzyl)-piperidin-4-yl]-quinolin-4-yl-amine,

[1-(4-allyloxy-3-ethoxy-benzyl)-piperidin-4-yl]-quinolin-4-yl-amine,
[1-(3-ethoxy-4-isopropoxy-benzyl)-piperidin-4-yl]-quinolin-4-yl-amine,
[1-(3-ethoxy-4-isobutoxy-benzyl)-piperidin-4-yl]-quinolin-4-yl-amine,
{1-[3-ethoxy-4-(1-ethyl-propoxy)-benzyl]-piperidin-4-yl}-quinolin-4-yl-amine,
[1-(4-cyclopentyloxy-3-ethoxy-benzyl)-piperidin-4-yl]-quinolin-4-yl-amine,
[1-(4-benzyloxy-3-ethoxy-benzyl)-piperidin-4-yl]-quinolin-4-yl-amine,
[1-(4-difluoromethoxy-3-ethoxy-benzyl)-piperidin-4-yl]-quinolin-4-yl-amine,
[1-(4-methoxy-3-propoxy-benzyl)-piperidin-4-yl]-quinolin-4-yl-amine,
[1-(3-isopropoxy-4-methoxy-benzyl)-piperidin-4-yl]-quinolin-4-yl-amine,
{1-[3-(2-fluoro-ethoxy)-4-methoxy-benzyl]-piperidin-4-yl}-quinolin-4-yl-amine,
[1-(3-allyloxy-4-methoxy-benzyl)-piperidin-4-yl]-quinolin-4-yl-amine, [1-(4-methoxy-3-prop-2-ynyloxy-benzyl)-piperidin-4-yl]-quinolin-4-yl-amine,
[1-(3-butoxy-4-methoxy-benzyl)-piperidin-4-yl]-quinolin-4-yl-amine,
[1-(3-isobutoxy-4-methoxy-benzyl)-piperidin-4-yl]-quinolin-4-yl-amine,
[1-(3-cyclopentyloxy-4-methoxy-benzyl)-piperidin-4-yl]-quinolin-4-yl-amine,
[1-(8-ethoxy-2,2-dimethyl-2H-chromen-6-ylmethyl)-piperidin-4-yl]-quinolin-4-yl-amine,
[1-(3,5-diethoxy-benzyl)-piperidin-4-yl]-quinolin-4-yl-amine,
[1-(3,5-diisopropoxy-benzyl)-piperidin-4-yl]-quinolin-4-yl-amine,
2,6-diethoxy-4-[4-(quinolin-4-ylamino)-piperidin-1-ylmethyl]-benzoic acid ethyl ester,
[1-(3,5-diethoxy-4-fluoro-benzyl)-piperidin-4-yl]-quinolin-4-yl-amine,
[1-(4-chloro-3,5-diethoxy-benzyl)-piperidin-4-yl]-quinolin-4-yl-amine,
[1-(4-bromo-3,5-diethoxy-benzyl)-piperidin-4-yl]-quinolin-4-yl-amine,
[1-(4-amino-3,5-diethoxy-benzyl)-piperidin-4-yl]-quinolin-4-yl-amine,
[1-(3,5-diethoxy-4-pyrrol-1-yl-benzyl)-piperidin-4-yl]-quinolin-4-yl-amine,
[1-(2,6-diethoxy-4'-fluoro-biphenyl-4-ylmethyl)-piperidin-4-yl]-quinolin-4-yl-amine,
(7-chloro-quinolin-4-yl)-[1-(3-ethoxy-4-fluoro-benzyl)-piperidin-4-yl]-amine,
[1-(4-chloro-3-ethoxy-benzyl)-piperidin-4-yl]-(7-chloro-quinolin-4-yl)-amine,
4-[4-(7-chloro-quinolin-4-ylamino)-piperidin-1-ylmethyl]-2-ethoxy-phenol,
(7-chloro-quinolin-4-yl)-[1-(3-ethoxy-4-methoxy-benzyl)-piperidin-4-yl]-amine,
[1-(4-allyloxy-3-ethoxy-benzyl)-piperidin-4-yl]-(7-chloro-quinolin-4-yl)-amine,
(7-chloro-quinolin-4-yl)-[1-(3-ethoxy-4-isopropoxy-benzyl)-piperidin-4-yl]-amine,
(7-chloro-quinolin-4-yl)-[1-(3-ethoxy-4-isobutoxy-benzyl)-piperidin-4-yl]-amine,
(7-chloro-quinolin-4-yl)-{1-[3-ethoxy-4-(1-ethyl-propoxy)-benzyl]-piperidin-4-yl}-amine,
(7-chloro-quinolin-4-yl)-[1-(4-cyclopentyloxy-3-ethoxy-benzyl)-piperidin-4-yl]-amine,
[1-(4-benzyloxy-3-ethoxy-benzyl)-piperidin-4-yl]-(7-chloro-quinolin-4-yl)-amine,
(7-chloro-quinolin-4-yl)-[1-(4-difluoromethoxy-3-ethoxy-benzyl)-piperidin-4-yl]-amine,
(7-chloro-quinolin-4-yl)-[1-(4-methoxy-3-propoxy-benzyl)-piperidin-4-yl]-amine,
(7-chloro-quinolin-4-yl)-[1-(3-isopropoxy-4-methoxy-benzyl)-piperidin-4-yl]-amine,
(7-chloro-quinolin-4-yl)-{1-[3-(2-fluoro-ethoxy)-4-methoxy-benzyl]-piperidin-4-yl}-amine,
[1-(3-allyloxy-4-methoxy-benzyl)-piperidin-4-yl]-(7-chloro-quinolin-4-yl)-amine,
(7-chloro-quinolin-4-yl)-[1-(4-methoxy-3-prop-2-ynyloxy-benzyl)-piperidin-4-yl]-amine,
(7-chloro-quinolin-4-yl)-[1-(3-isobutoxy-4-methoxy-benzyl)-piperidin-4-yl]-amine,
(7-chloro-quinolin-4-yl)-[1-(3-cyclopentyloxy-4-methoxy-benzyl)-piperidin-4-yl]-amine,
2-{4-[4-(7-chloro-quinolin-4-ylamino)-piperidin-1-ylmethyl]-2-ethoxy-5-fluoro-phenoxy}-ethanol,
(7-chloro-quinolin-4-yl)-[1-(8-ethoxy-2,2-dimethyl-2H-chromen-6-ylmethyl)-piperidin-4-yl]-amine,
(7-chloro-quinolin-4-yl)-[1-(3,5-diethoxy-benzyl)-piperidin-4-yl]-amine,
(7-chloro-quinolin-4-yl)-[1-(3,5-diisopropoxy-benzyl)-piperidin-4-yl]-amine,
4-[4-(7-chloro-quinolin-4-ylamino)-piperidin-1-ylmethyl]-2,6-diethoxy-benzoic acid ethyl ester,
(7-chloro-quinolin-4-yl)-[1-(3,5-diethoxy-4-fluoro-benzyl)-piperidin-4-yl]-amine,
[1-(4-chloro-3,5-diethoxy-benzyl)-piperidin-4-yl]-(7-chloro-quinolin-4-yl)-amine,
[1-(4-bromo-3,5-diethoxy-benzyl)-piperidin-4-yl]-(7-chloro-quinolin-4-yl)-amine,
(7-chloro-quinolin-4-yl)-[1-(3,5-diethoxy-4-pyrrol-1-yl-benzyl)-piperidin-4-yl]-amine,
(7-chloro-quinolin-4-yl)-[1-(2,6-diethoxy-4'-fluoro-biphenyl-4-ylmethyl)-piperidin-4-yl]-amine,
[1-(4-chloro-3-ethoxy-benzyl)-piperidin-4-yl]-pyrimidin-5-yl-amine,
[1-(3-isobutoxy-4-methoxy-benzyl)-piperidin-4-yl]-pyrimidin-5-yl-amine,
[1-(8-ethoxy-2,2-dimethyl-2H-chromen-6-ylmethyl)-piperidin-4-yl]-pyrimidin-5-yl-amine,
[1-(3,5-diethoxy-benzyl)-piperidin-4-yl]-pyrimidin-5-yl-amine,
3-isopropoxy-5-[4-(pyrimidin-5-ylamino)-piperidin-1-ylmethyl]-phenol,
[1-(3,5-diisopropoxy-benzyl)-piperidin-4-yl]-pyrimidin-5-yl-amine,
[1-(3,5-diethoxy-4-fluoro-benzyl)-piperidin-4-yl]-pyrimidin-5-yl-amine,
[1-(4-chloro-3,5-diethoxy-benzyl)-piperidin-4-yl]-pyrimidin-5-yl-amine,
[1-(4-bromo-3,5-diethoxy-benzyl)-piperidin-4-yl]-pyrimidin-5-yl-amine,
[1-(4-amino-3,5-diethoxy-benzyl)-piperidin-4-yl]-pyrimidin-5-yl-amine,
[1-(3,5-diethoxy-4-pyrrol-1-yl-benzyl)-piperidin-4-yl]-pyrimidin-5-yl-amine,
[1-(3-ethoxy-4-methyl-benzyl)-piperidin-4-yl]-(2-phenyl-pyrimidin-5-yl)-amine,
[1-(3-ethoxy-4-fluoro-benzyl)-piperidin-4-yl]-(2-phenyl-pyrimidin-5-yl)-amine,
[1-(4-chloro-3-ethoxy-benzyl)-piperidin-4-yl]-(2-phenyl-pyrimidin-5-yl)-amine,

[1-(3-ethoxy-4-methoxy-benzyl)-piperidin-4-yl]-(2-phenyl-pyrimidin-5-yl)-amine,
[1-(4-allyloxy-3-ethoxy-benzyl)-piperidin-4-yl]-(2-phenyl-pyrimidin-5-yl)-amine,
[1-(3-ethoxy-4-isobutoxy-benzyl)-piperidin-4-yl]-(2-phenyl-pyrimidin-5-yl)-amine,
{1-[3-ethoxy-4-(1-ethyl-propoxy)-benzyl]-piperidin-4-yl}-(2-phenyl-pyrimidin-5-yl)-amine,
[1-(4-cyclopentyloxy-3-ethoxy-benzyl)-piperidin-4-yl]-(2-phenyl-pyrimidin-5-yl)-amine,
[1-(4-difluoromethoxy-3-ethoxy-benzyl)-piperidin-4-yl]-(2-phenyl-pyrimidin-5-yl)-amine,
[1-(4-methoxy-3-propoxy-benzyl)-piperidin-4-yl]-(2-phenyl-pyrimidin-5-yl)-amine,
[1-(3-isopropoxy-4-methoxy-benzyl)-piperidin-4-yl]-(2-phenyl-pyrimidin-5-yl)-amine,
[1-(3-allyloxy-4-methoxy-benzyl)-piperidin-4-yl]-(2-phenyl-pyrimidin-5-yl)-amine,
[1-(3-butoxy-4-methoxy-benzyl)-piperidin-4-yl]-(2-phenyl-pyrimidin-5-yl)-amine,
[1-(3-isobutoxy-4-methoxy-benzyl)-piperidin-4-yl]-(2-phenyl-pyrimidin-5-yl)-amine,
[1-(3-cyclopentyloxy-4-methoxy-benzyl)-piperidin-4-yl]-(2-phenyl-pyrimidin-5-yl)-amine,
[1-(8-ethoxy-2,2-dimethyl-2H-chromen-6-ylmethyl)-piperidin-4-yl]-(2-phenyl-pyrimidin-5-yl)-amine,
[1-(3,5-diethoxy-benzyl)-piperidin-4-yl]-(2-phenyl-pyrimidin-5-yl)-amine,
2,6-diethoxy-4-[4-(2-phenyl-pyrimidin-5-ylamino)-piperidin-1-ylmethyl]-benzoic acid ethyl ester,
[1-(3,5-diethoxy-4-fluoro-benzyl)-piperidin-4-yl]-(2-phenyl-pyrimidin-5-yl)-amine,
[1-(4-chloro-3,5-diethoxy-benzyl)-piperidin-4-yl]-(2-phenyl-pyrimidin-5-yl)-amine,
[1-(4-bromo-3,5-diethoxy-benzyl)-piperidin-4-yl]-(2-phenyl-pyrimidin-5-yl)-amine,
[1-(3,5-diethoxy-4-pyrrol-1-yl-benzyl)-piperidin-4-yl]-(2-phenyl-pyrimidin-5-yl)-amine,
[1-(2,6-diethoxy-4'-fluoro-biphenyl-4-ylmethyl)-piperidin-4-yl]-(2-phenyl-pyrimidin-5-yl)-amine,
[1-(4-chloro-3-ethoxy-benzyl)-piperidin-4-yl]-(2-morpholin-4-yl-pyrimidin-5-yl)-amine,
[1-(4-chloro-3,5-diethoxy-benzyl)-piperidin-4-yl]-(2-morpholin-4-yl-pyrimidin-5-yl)-amine,
[1-(2,6-diethoxy-4'-fluoro-biphenyl-4-ylmethyl)-piperidin-4-yl]-(2-morpholin-4-yl-pyrimidin-5-yl)-amine,
and pharmaceutically acceptable salts thereof.

22. The compound according to claim 1, selected from the group consisting of
[1-(4-difluoromethoxy-3-ethoxy-benzyl)-piperidin-4-yl]-pyridin-3-yl-amine,
[1-(3,5-diisopropoxy-benzyl)-piperidin-4-yl]-pyridin-3-yl-amine,
[1-(4-chloro-3,5-diethoxy-benzyl)-piperidin-4-yl]-pyridin-3-yl-amine,
[1-(4-bromo-3,5-diethoxy-benzyl)-piperidin-4-yl]-pyridin-3-yl-amine,
[1-(3,5-diethoxy-4-pyrrol-1-yl-benzyl)-piperidin-4-yl]-pyridin-3-yl-amine,
N-{5-[1-(4-chloro-3,5-diethoxy-benzyl)-piperidin-4-ylamino]-pyridin-2-yl}-acetamide,
$N^5$-[1-(2,6-diethoxy-4'-fluoro-biphenyl-4-ylmethyl)-piperidin-4-yl]-3-methyl-pyridine-2,5-diamine,
[1-(3-isopropoxy-4-methoxy-benzyl)-piperidin-4-yl]-quinolin-3-yl-amine,
2,6-diethoxy-4-[4-(quinolin-3-ylamino)-piperidin-1-ylmethyl]-benzoic acid ethyl ester,
[1-(4-chloro-3,5-diethoxy-benzyl)-piperidin-4-yl]-quinolin-3-yl-amine,
[1-(4-chloro-3,5-diethoxy-benzyl)-piperidin-4-yl]-(2-methyl-pyridin-4-yl)-amine,
[1-(4-cyclopentyloxy-3-ethoxy-benzyl)-piperidin-4-yl]-quinolin-4-yl-amine,
[1-(4-difluoromethoxy-3-ethoxy-benzyl)-piperidin-4-yl]-quinolin-4-yl-amine,
[1-(4-benzyloxy-3-ethoxy-benzyl)-piperidin-4-yl]-(7-chloro-quinolin-4-yl)-amine,
[1-(3,5-diethoxy-4-fluoro-benzyl)-piperidin-4-yl]-pyrimidin-5-yl-amine,
[1-(4-chloro-3,5-diethoxy-benzyl)-piperidin-4-yl]-pyrimidin-5-yl-amine,
[1-(4-bromo-3,5-diethoxy-benzyl)-piperidin-4-yl]-pyrimidin-5-yl-amine,
[1-(3,5-diethoxy-4-pyrrol-1-yl-benzyl)-piperidin-4-yl]-pyrimidin-5-yl-amine,
[1-(4-chloro-3-ethoxy-benzyl)-piperidin-4-yl]-(2-phenyl-pyrimidin-5-yl)-amine,
[1-(4-allyloxy-3-ethoxy-benzyl)-piperidin-4-yl]-(2-phenyl-pyrimidin-5-yl)-amine,
[1-(4-difluoromethoxy-3-ethoxy-benzyl)-piperidin-4-yl]-(2-phenyl-pyrimidin-5-yl)-amine,
[1-(4-methoxy-3-propoxy-benzyl)-piperidin-4-yl]-(2-phenyl-pyrimidin-5-yl)-amine,
[1-(3-isopropoxy-4-methoxy-benzyl)-piperidin-4-yl]-(2-phenyl-pyrimidin-5-yl)-amine,
[1-(3-isobutoxy-4-methoxy-benzyl)-piperidin-4-yl]-(2-phenyl-pyrimidin-5-yl)-amine,
[1-(3-cyclopentyloxy-4-methoxy-benzyl)-piperidin-4-yl]-(2-phenyl-pyrimidin-5-yl)-amine,
[1-(3,5-diethoxy-benzyl)-piperidin-4-yl]-(2-phenyl-pyrimidin-5-yl)-amine,
2,6-diethoxy-4-[4-(2-phenyl-pyrimidin-5-ylamino)-piperidin-1-ylmethyl]-benzoic acid ethyl ester,
[1-(3,5-diethoxy-4-fluoro-benzyl)-piperidin-4-yl]-(2-phenyl-pyrimidin-5-yl)-amine,
[1-(4-chloro-3,5-diethoxy-benzyl)-piperidin-4-yl]-(2-phenyl-pyrimidin-5-yl)-amine,
[1-(4-bromo-3,5-diethoxy-benzyl)-piperidin-4-yl]-(2-phenyl-pyrimidin-5-yl)-amine,
[1-(3,5-diethoxy-4-pyrrol-1-yl-benzyl)-piperidin-4-yl]-(2-phenyl-pyrimidin-5-yl)-amine,
[1-(2,6-diethoxy-4'-fluoro-biphenyl-4-ylmethyl)-piperidin-4-yl]-(2-phenyl-pyrimidin-5-yl)-amine,
and pharmaceutically acceptable salts thereof.

23. A process for the manufacture of a compound according to claim 1, comprising the steps of:
a) reacting a compound of the general formula

G-X      II wherein G is as defined in claim 1 and X is a leaving group, with a compound of the formula

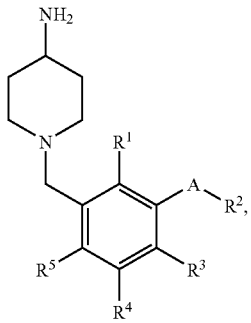

wherein A and $R^1$ to $R^5$ are as defined in claim 1,
to obtain a compound of the formula

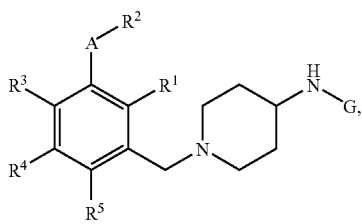

and, if desired, converting the compound of formula I into a pharmaceutically acceptable salt; or, alternatively, b) reacting a compound of the general formula

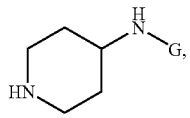

wherein G is as defined in claim 1,
with an aldehyde of the formula

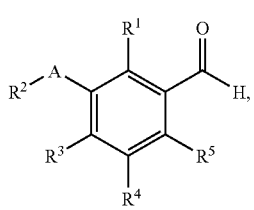

wherein A and $R^1$ to $R^5$ are as defined in claim 1, by employing a reducing agent to obtain a compound of the formula

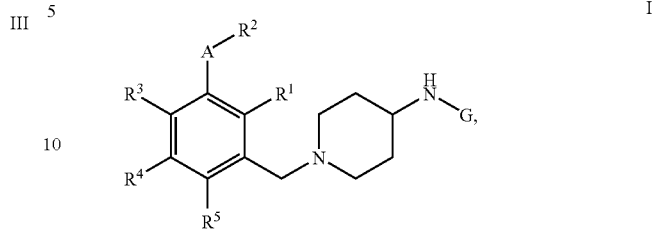

and, if desired, converting the compound of formula I into a pharmaceutically acceptable salt; or, alternatively, c) alkylating a compound of the general formula

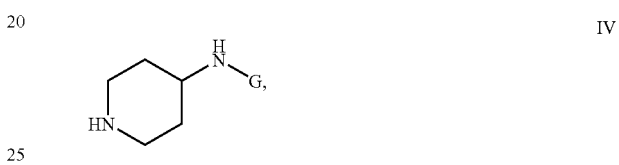

wherein G is as defined in claim 1,
with a compound of the formula

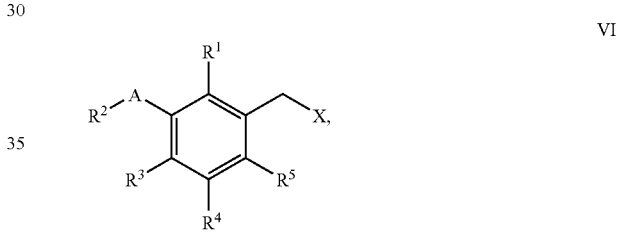

wherein A and $R^1$ to $R^5$ are as defined in claim 1 and X is a leaving group,
under basic conditions to obtain a compound or formula

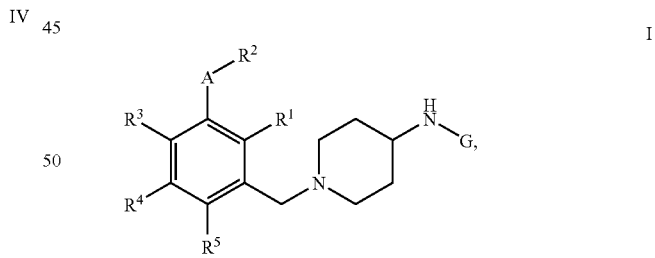

and, if desired, converting the compound of formula I into a pharmaceutically acceptable salt; or, alternatively, d) reacting a compound of the general formula

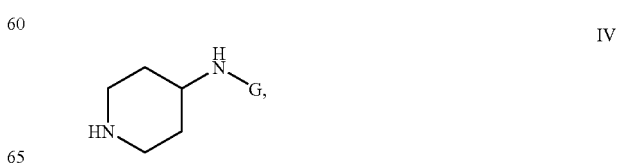

wherein G is as defined in claim 1, with a compound of the formula

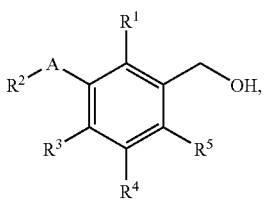

wherein A and $R^1$ to $R^5$ are as defined in claim 1, in the presence of a trialkylphosphine and a diazo-compound to obtain a compound or formula

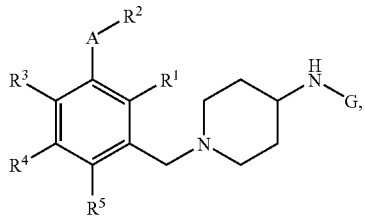

and, if desired, converting the compound of formula I into a pharmaceutically acceptable salt.

24. A pharmaceutical composition, comprising a therapeutically effective amount of a compound according to claim 1 as well as a pharmaceutically acceptable carrier and/or adjuvant.

* * * * *